United States Patent
Hentemann et al.

(10) Patent No.: US 8,859,572 B2
(45) Date of Patent: Oct. 14, 2014

(54) SULFONE SUBSTITUTED 2,3-DIHYDROIMIDAZO [1,2-C] QUINAZOLINE DERIVATIVES USEFUL FOR TREATING HYPER-PROLIFERATIVE DISORDERS AND DISEASES WITH ANGIOGENESIS

(75) Inventors: Martin F. Hentemann, Carlisle, MA (US); William Scott, Guilford, CT (US); Jill Wood, Ft. Collins, CO (US); Jeffrey Johnson, North Branford, CT (US); Aniko Redman, Durham, NC (US); Ann-Marie Bullion, King of Prussia, PA (US); Leatte Guernon, Moodus, CT (US)

(73) Assignee: Bayer Intellectual Property GmbH, Monheim (DE)

( * ) Notice: Subject to any disclaimer, the term of this patent is extended or adjusted under 35 U.S.C. 154(b) by 1036 days.

(21) Appl. No.: 12/812,911

(22) PCT Filed: Jan. 13, 2009

(86) PCT No.: PCT/US2009/000228
§ 371 (c)(1),
(2), (4) Date: Apr. 18, 2011

(87) PCT Pub. No.: WO2009/091550
PCT Pub. Date: Jul. 23, 2009

(65) Prior Publication Data
US 2011/0190281 A1    Aug. 4, 2011

Related U.S. Application Data

(60) Provisional application No. 61/021,029, filed on Jan. 14, 2008.

(51) Int. Cl.
| | |
|---|---|
| A61K 31/519 | (2006.01) |
| A61K 45/06 | (2006.01) |
| A61K 31/541 | (2006.01) |
| C07D 487/04 | (2006.01) |

(52) U.S. Cl.
CPC ............... *A61K 45/06* (2013.01); *A61K 31/541* (2013.01); *A61K 2300/00* (2013.01); *C07D 487/04* (2013.01); *A61K 31/519* (2013.01)
USPC ......................................... 514/267; 544/250

(58) Field of Classification Search
CPC . C07D 487/04; A61K 31/541; A61K 31/519; A61K 31/5377; A61K 2300/00
USPC ......................................... 514/267; 544/250
See application file for complete search history.

(56) References Cited

U.S. PATENT DOCUMENTS 7,511,041 B2 * 3/2009 Shimada et al. .............. 514/250

OTHER PUBLICATIONS

Khwaja, et al., Prenylation is Not Necessary for Endogenous Ras Activation in Non-Malignant Cells, J. or Cellular Biochem. 97:412-422 (2006).*

* cited by examiner

Primary Examiner — Erich A Leeser

(57) ABSTRACT

This invention relates to novel sulfone 2I3-dihydroimidazo[1 l2-c]quinazoline compounds, pharmaceutical compositions containing such compounds and the use of those compounds or compositions for phosphotidylinositol-3-kinase (PI3K) inhibition and treating diseases associated with phosphotidylinositol-3-kinase (PI3K) activity, in particular treating hyper-proliferative and/or angiogenesis mediated disorders, as a sole agent or in combination with other active ingredients.

16 Claims, No Drawings

SULFONE SUBSTITUTED 2,3-DIHYDROIMIDAZO [1,2-C] QUINAZOLINE DERIVATIVES USEFUL FOR TREATING HYPER-PROLIFERATIVE DISORDERS AND DISEASES WITH ANGIOGENESIS

FIELD OF THE INVENTION

This invention relates to novel sulfone substituted 2,3-dihydroimidazo[1,2-c]quinazoline compounds, pharmaceutical compositions containing such compounds and the use of those compounds or compositions for phosphotidylinositol-3-kinase (PI3K) inhibition and treating diseases associated with phosphotidylinositol-3-kinase (PI3K) activity, in particular treating hyper-proliferative and/or angiogenesis mediated disorders, as a sole agent or in combination with other active ingredients.

BACKGROUND OF THE INVENTION

In the last decade the concept of developing anti-cancer medications which target abnormally active protein kinases has led to a number of successes. In addition to the actions of protein kinases, lipid kinases also play an important role in generating critical regulatory second messengers. The PI3K family of lipid kinases generates 3'-phosphoinositides that bind to and activate a variety of cellular targets, initiating a wide range of signal transduction cascades (Vanhaesebroeck et al., 2001; Toker, 2002; Pendaries et al., 2003; Downes et al., 2005). These cascades ultimately induce changes in multiple cellular processes, including cell proliferation, cell survival, differentiation, vesicle trafficking, migration, and chemotaxis.

PI3Ks can be divided into three distinct classes based upon differences in both structure, and substrate preference. While members of the Class II family of PI3Ks have been implicated in the regulation of tumor growth (Brown and Shepard, 2001; Traer et al., 2006), the bulk of research has focused on the Class I enzymes and their role in cancer (Vivanco and Sawyers, 2002; Workman, 2004, Chen et al., 2005; Hennessey et al., 2005; Stauffer et al., 2005; Stephens et al., 2005; Cully et al., 2006).

Class I PI3Ks have traditionally been divided into two distinct sub-classes based upon differences in protein subunit composition. The Class $I_A$ PI3Ks are comprised of a catalytic p110 catalytic subunit (p110α, β or δ) heterodimerized with a member of the p85 regulatory subunit family. In contrast, the Class $I_B$ PI3K catalytic subunit (p110γ) heterodimerizes with a distinct p101 regulatory subunit (reviewed by Vanhaesebroeck and Waterfield, 1999; Funaki et al., 2000; Katso et al., 2001). The C-terminal region of these proteins contains a catalytic domain that possesses distant homology to protein kinases. The PI3Kγ structure is similar to Class $I_A$ p110s, but lacks the N-terminal p85 binding site (Domin and Waterfield, 1997). Though similar in overall structure, the homology between catalytic p110 subunits is low to moderate. The highest homology between the PI3K isoforms is in the kinase pocket of the kinase domain.

The Class $I_A$ PI3K isoforms associate with activated receptor tyrosine kinases (RTKs) (including PDGFR, EGFR, VEGFR, IGF1-R, c-KIT, CSF-R and Met), or with tyrosine phosphorylated adapter proteins (such as Grb2, Cbl, IRS-1 or Gab1), via their p85 regulatory subunits resulting in stimulation of the lipid kinase activity. Activation of the lipid kinase activity of the p110β and p110γ isoforms has been shown to occur in response to binding to activated forms of the ras Oncogene (Kodaki et al, 1994). In fact, the oncogenic activity of these isoforms may require binding to ras (Kang et al., 2006). In contrast, the p110α and p110δ isoforms exhibit oncogenic activity independent of ras binding, through constitutive activation of Akt.

Class I PI3Ks catalyze the conversion of $PI(4,5)P_2$ [$PIP_2$] to $PI(3,4,5)P_3$ [$PIP_3$]. The production of $PIP_3$ by PI3K affects multiple signaling processes that regulate and coordinate the biological end points of cell proliferation, cell survival, differentiation and cell migration. $PIP_3$ is bound by Pleckstrin-Homology (PH) domain-containing proteins, including the phosphoinositide-dependent kinase, PDK1 and the Akt proto-oncogene product, localizing these proteins in regions of active signal transduction and also contributing directly to their activation (Klippel et al., 1997; Fleming et al., 2000; Itoh and Takenawa, 2002; Lemmon, 2003). This co-localization of PDK1 with Akt facilitates the phosphorylation and activation of Akt.

Carboxy-terminal phosphorylation of Akt on $Ser^{473}$ promotes phosphorylation of $Thr^{308}$ in the Akt activation loop (Hodgekinson et al., 2002; Scheid et al., 2002; Hresko et al., 2003). Once active, Akt phosphorylates and regulates multiple regulatory kinases of pathways that directly influence cell cycle progression and cell survival.

Many of the effects of Akt activation are mediated via its negative regulation of pathways which impact cell survival and which are commonly dysregulated in cancer. Akt promotes tumor cell survival by regulating components of the apoptotic and cell cycle machinery. Akt is one of several kinases that phosphorylate and inactivate pro-apoptotic BAD proteins (del Paso et al., 1997; Pastorino et al., 1999). Akt may also promote cell survival through blocking cytochrome C-dependent caspase activation by phosphorylating Caspase 9 on $Ser^{196}$ (Cardone et al., 1998).

Akt impacts gene transcription on several levels. The Akt-mediated phosphorylation of the MDM2 E3 ubiquitin ligase on $Ser^{166}$ and $Ser^{186}$ facilitates the nuclear import of MDM2 and the formation and activation of the ubiquitin ligase complex. Nuclear MDM2 targets the p53 tumor suppressor for degradation, a process that can be blocked by LY294002 (Yap et al., 2000; Ogarawa et al., 2002). Downregulation of p53 by MDM2 negatively impacts the transcription of p53-regulated pro-apoptotic genes (e.g. Bax, Fas, PUMA and DR5), the cell cycle inhibitor, $p21^{Cip1}$, and the PTEN tumor suppressor (Momand et al., 2000; Hupp et al., 2000; Mayo et al., 2002; Su et al., 2003). Similarly, the Akt-mediated phosphorylation of the Forkhead transcription factors FKHR, FKHRL and AFX (Kops et al., 1999; Tang et al., 1999), facilitates their binding to 14-3-3 proteins and export from the cell nucleus to the cytosol (Brunet et al., 1999). This functional inactivation of Forkhead activity also impacts pro-apoptotic and pro-angiogenic gene transcription including the transcription of the Fas ligand (Ciechomska et al., 2003) Bim, a pro-apoptotic Bcl-2 family member (Dijkers et al., 2000), and the Angiopoietin-1 (Ang-1) antagonist, Ang-2 (Daly et al., 2004). Forkhead transcription factors regulate the expression of the cyclin-dependent kinase (Cdk) inhibitor $p27^{Kip1}$. Indeed, PI3K inhibitors have been demonstrated to induce $p27^{Kip1}$ expression resulting in Cdk1 inhibition, cell cycle arrest and apoptosis (Dijkers et al., 2000). Akt is also reported to phosphorylate $p21^{Cip1}$ on $Thr^{145}$ and $p27^{Kip1}$ on $Thr^{157}$ facilitating their association with 14-3-3 proteins, resulting in nuclear export and cytoplasmic retention, preventing their inhibition of nuclear Cdks (Zhou et al., 2001; Motti et al., 2004; Sekimoto et al., 2004). In addition to these effects, Akt phosphorylates IKK (Romashkova and Makarov, 1999), leading to the phosphorylation and degradation of IκB and subsequent nuclear translocation of NFκB, resulting in the expression of survival genes such as IAP and Bcl-$X_L$.

The PI3K/Akt pathway is also linked to the suppression of apoptosis through the JNK and p38$^{MAPK}$ MAP Kinases that are associated with the induction of apoptosis. Akt is postulated to suppress JNK and p38$^{MAPK}$ signaling through the phosphorylation and inhibition of two JNK/p38 regulatory kinases, Apoptosis Signal-regulating Kinase 1 (ASK1) (Kim et al., 2001: Liao and Hung, 2003; Yuan et al., 2003), and Mixed Lineage Kinase 3 (MLK3) (Lopez-Ilasaca et al., 1997; Barthwal et al., 2003; Figueroa et al., 2003). The induction of p38$^{MAPK}$ activity is observed in tumors treated with cytotoxic agents and is required for those agents to induce cell death (reviewed by Olson and Hallahan, 2004). Thus, inhibitors of the PI3K pathway may promote the activities of co-administered cytotoxic drugs.

An additional role for PI3K/Akt signaling involves the regulation of cell cycle progression through modulation of Glycogen Synthase Kinase 3 (GSK3) activity. GSK3 activity is elevated in quiescent cells, where it phosphorylates cyclin $D_1$ on Ser$^{286}$, targeting the protein for ubiquitination and degradation (Diehl et al., 1998) and blocking entry into S-phase. Akt inhibits GSK3 activity through phosphorylation on Ser$^9$ (Cross et al., 1995). This results in the elevation of Cyclin $D_1$ levels which promotes cell cycle progression. Inhibition of GSK3 activity also impacts cell proliferation through activation of the wnt/beta-catenin signaling pathway (Abbosh and Nephew, 2005; Naito et al., 2005; Wilker et al., 2005; Kim et al., 2005; Segrelles et al., 2006). Akt mediated phosphorylation of GSK3 results in stabilization and nuclear localization of the beta-catenin protein, which in turn leads to increased expression of c-myc and cyclin D1, targets of the beta-catenin/Tcf pathway.

Although PI3K signaling is utilized by many of the signal transduction networks associated with both oncogenes and tumor suppressors, PI3K and its activity have been linked directly to cancer. Overexpression of both the p110α and p110β isoforms has been observed in bladder and colon tumors and cell lines, and overexpression generally correlates with increased PI3K activity (Bénistant et al., 2000). Overexpression of p110α has also been reported in ovarian and cervical tumors and tumor cell lines, as well as in squamous cell lung carcinomas. The overexpression of p110α in cervical and ovarian tumor lines is associated with increased PI3K activity (Shayesteh et al., 1999; Ma et al., 2000). Elevated PI3K activity has been observed in colorectal carcinomas (Phillips et al., 1998) and increased expression has been observed in breast carcinomas (Gershtein et al., 1999).

Over the last few years, somatic mutations in the gene encoding p110α (PIK3CA) have been identified in numerous cancers. The data collected to date suggests that PIK3CA is mutated in approximately 32% of colorectal cancers (Samuels et al., 2004; Ikenoue et al., 2005), 18-40% of breast cancers (Bachman et al., 2004; Campbell et al., 2004; Levine et al., 2005; Saal et al., 2005; Wu et al., 2005), 27% of glioblastomas (Samuels et al., 2004; Hartmann et al., 2005, Gallia et al., 2006), 25% of gastric cancers (Byun et al., 2003; Samuels et al., 2004; Li et al., 2005), 36% of hepatocellular carcinomas (Lee et al., 2005), 4-12% of ovarian cancers (Levine et al., 2005; Wang et al., 2005), 4% of lung cancers (Samuels et al., 2004; Whyte and Holbeck, 2006), and up to 40% of endometrial cancers (Oda et al., 2005). PIK3CA mutations have been reported in oligodendroma, astrocytoma, medulloblastoma, and thyroid tumors as well (Broderick et al., 2004). Based upon the observed high frequency of mutation, PIK3CA is one of the two most frequently mutated genes associated with cancer, the other being K-ras. More than 80% of the PIK3CA mutations cluster within two regions of the protein, the helical (E545K) and catalytic (H1047R) domains. Biochemical analysis and protein expression studies have demonstrated that both mutations lead to increased constitutive p110α catalytic activity and are in fact, oncogenic (Bader et al., 2006; Kang et al., 2005; Samuels et al., 2005; Samuels and Ericson, 2006). Recently, it has been reported that PIK3CA knockout mouse embryo fibroblasts are deficient in signaling downstream from various growth factor receptors (IGF-1, Insulin, PDGF, EGF), and are resistant to transformation by a variety of oncogenic RTKs (IGFR, wild-type EGFR and somatic activating mutants of EGFR, Her2/Neu) (Zhao et al., 2006).

Functional studies of PI3K in vivo have demonstrated that siRNA-mediated downregulation of p110β inhibits both Akt phosphorylation and HeLa cell tumor growth in nude mice (Czauderna et al., 2003). In similar experiments, siRNA-mediated downregulation of p110β was also shown to inhibit the growth of malignant glioma cells in vitro and in vivo (Pu et al., 2006). Inhibition of PI3K function by dominant-negative p85 regulatory subunits can block mitogenesis and cell transformation (Huang et al., 1996; Rahimi et al., 1996). Several somatic mutations in the genes encoding the p85α and p85β regulatory subunits of PI3K that result in elevated lipid kinase activity have been identified in a number of cancer cells as well (Janssen et al., 1998; Jimenez et al., 1998; Philp et al., 2001; Jucker et al., 2002; Shekar et al., 2005). Neutralizing PI3K antibodies also block mitogenesis and can induce apoptosis in vitro (Roche et al., 1994: Roche et al., 1998; Bénistant et al., 2000). In vivo proof-of-principle studies using the PI3K inhibitors LY294002 and wortmannin, demonstrate that inhibition of PI3K signaling slows tumor growth in vivo (Powis et al., 1994; Shultz et al., 1995; Semba et al., 2002; Ihle et al., 2004).

Overexpression of Class I PI3K activity, or stimulation of their lipid kinase activities, is associated with resistance to both targeted (such as imatinib and tratsuzumab) and cytotoxic chemotherapeutic approaches, as well as radiation therapy (West et al., 2002; Gupta et al., 2003; Osaki et al., 2004; Nagata et al., 2004; Gottschalk et al., 2005; Kim et al., 2005). Activation of PI3K has also been shown to lead to expression of multidrug resistant protein-1 (MRP-1) in prostate cancer cells and the subsequent induction of resistance to chemotherapy (Lee et al., 2004).

The importance of PI3K signaling in tumorigenesis is further underscored by the findings that the PTEN tumor suppressor, a PI(3)P phosphatase, is among the most commonly inactivated genes in human cancers (Li et al., 1997, Steck et al., 1997; Ali et al., 1999; Ishii et al., 1999). PTEN dephosphorylates PI(3,4,5)$P_3$ to PI(4,5)$P_2$ thereby antagonizing PI3K-dependent signaling. Cells containing functionally inactive PTEN have elevated levels of $PIP_3$, high levels of activity of PI3K signaling (Haas-Kogan et al., 1998; Myers et al., 1998; Taylor et al., 2000), increased proliferative potential, and decreased sensitivity to pro-apoptotic stimuli (Stambolic et al., 1998). Reconstitution of a functional PTEN suppresses PI3K signaling (Taylor et al., 2000), inhibits cell growth and re-sensitizes cells to pro-apoptotic stimuli (Myers et al., 1998; Zhao et al., 2004). Similarly, restoration of PTEN function in tumors lacking functional PTEN inhibits tumor growth in vivo (Stahl et al., 2003; Su et al., 2003; Tanaka and Grossman, 2003) and sensitizes cells to cytotoxic agents (Tanaka and Grossman, 2003).

The class I family of PI3Ks clearly plays an important role in the regulation of multiple signal transduction pathways that promote cell survival and cell proliferation, and activation of their lipid kinase activity contributes significantly to the development of human malignancies. Furthermore, inhibition of PI3K may potentially circumvent the cellular mechanisms that underlie resistance to chemotherapeutic agents. A potent inhibitor of Class I PI3K activities would therefore have the potential not only to inhibit tumor growth but to also sensitize tumor cells to pro-apoptotic stimuli in vivo.

Signal transduction pathways originating from chemoattractant receptors are considered to be important targets in controlling leukocyte motility in inflammatory diseases. Leukocyte trafficking is controlled by chemoattractant factors that activate heterotrimeric GPCRs and thereby trigger a variety of downstream intracellular events. Signal transduction along one of these pathways that results in mobilization of free $Ca^{2+}$, cytoskelatal reorganization, and directional movement depends on lipid-derived second messengers produced by PI3K activity (Wymann et al., 2000; Stein and Waterfield, 2000).

PI3Kγ modulates baseline cAMP levels and controls contractility in cells. Recent research indicates that alterations in baseline cAMP levels contributes to the increased contractility in mutant mice. This research, therefore, shows that PI3Kγ inhibitors would afford potential treatments for congestive heart failure, ischemia, pulmonary hypertension, renal failure, cardiac hypertrophy, atherosclerosis, thromboembolism, and diabetes.

PI3K inhibitors would be expected to block signal transduction from GPCRs and block the activation of various immune cells, leading to a broad anti-inflammatory profile with potential for the treatment of inflammatory and immunoregulatory diseases, including asthma, atopic dermatitis, rhinitis, allergic diseases, chronic obstructive pulmonary disease (COPD), septic shock, joint diseases, autoimmune pathologies such as rheumatoid arthritis and Graves' disease, diabetes, cancer, myocardial contractility disorders, thromboembolism, and atherosclerosis.

PI3K inhibitor compounds and compositions described herein, including salts, metabolites, solvates, solvates of salts, hydrates, and stereoisomeric forms thereof, exhibit anti-proliferative activity and are thus useful to prevent or treat the disorders associated with hyper-proliferation.

DESCRIPTION OF THE INVENTION

One embodiment of this invention encompasses a compound having the formula (I):

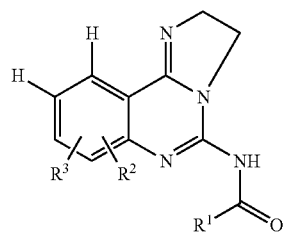

or a physiologically acceptable salt, solvate, hydrate or stereoisomer thereof,
wherein:
$R^1$ is a heteroaryl optionally substituted with 1, 2 or 3 $R^4$ groups;
$R^2$ is hydrogen, alkoxy, heterocyclylalkyl, heterocyclylalkoxy or $R^3$;

each occurrence of $R^3$ is independently

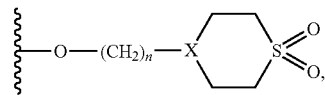

—Y—$SO_q$—Z or —Y—N($R^5$)—$SO_q$—Z;
each occurrence of X is independently —C($R^5$)— or —N—;
each occurrence of Y is independently a bond, alkoxy, alkoxyalkoxy or arylalkoxy;
each occurrence of Z is independently alkyl, —N($R^6$)($R^{6'}$), or -heterocyclylalkyl optionally substituted with 1, 2 or 3 $R^4$ groups;
each occurrence of $R^4$ may be the same or different and is independently amino, halogen, amino, alkylamino, alkyl, alkenyl, alkynyl, cycloalkyl, cycloalkylalkyl, aryl, arylalkyl, heteroaryl, heteroarylalkyl, heterocyclyl or heterocyclylalkyl;
each occurrence of $R^5$ is independently hydrogen or alkyl;
each occurrence of $R^6$ and $R^{6'}$ may be the same or different and is independently hydrogen, alkyl, alkenyl, alkynyl, cycloalkyl, cycloalkylalklyl, cycloalkenyl, aryl, arylalkyl, heteroaryl, heterocyclyl, or heterocyclylalkyl, wherein $R^6$ and $R^{6'}$ may be attached to each other to form a heterocyclic ring through a bond or through one or more O, C, N, S, $SO_q$ or carbonyl, and wherein at least one N is part of the heterocyclic ring; and
each occurrence of n is independently an integer from 1-4; and
each occurrence of p is independently an integer from 0-2.

In a preferred embodiment, the invention encompasses a compound of formula (I), wherein $R^2$ is alkoxy, more preferably methoxy.

In another preferred embodiment, the invention encompasses a compound of formula (I), wherein $R^1$ is pyridine, pyrimidine or thiazole, optionally substituted with 1, 2 or 3 $R^4$ groups; more preferably optionally substituted with 1 or 2 amino or methyl groups; most preferably pyridin-3-yl.

In still another preferred embodiment, the invention encompasses a compound of formula (I), wherein $R^2$ is N-morpholino-alkoxy.

In yet another preferred embodiment, the invention encompasses a compound of formula (I), wherein $R^3$—Y—$SO_2$—Z or —Y—NH—$SO_2$—Z, more preferably wherein Z is N-morpholino, methyl, or alkylamino.

In a distinct embodiment, the invention encompasses a compound of formula (I), wherein:
$R^1$ is a heteroaryl optionally substituted with 1 $R^4$ group;
$R^2$ is alkoxy or heterocyclylalkoxy;
$R^3$ is independently

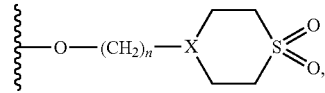

—Y—$SO_2$—Z or —Y—NH—$SO_2$—Z;
each occurrence of Y is independently alkoxy, alkoxyalkoxy, or arylalkoxy;
each occurrence of Z is independently alkyl, —N($R^6$)($R^{6'}$), or -heterocyclylalkyl;
each occurrence of $R^4$ may be the same or different and is independently amino, halogen, amino, alkylamino, alkyl, alkenyl, alkynyl, cycloalkyl, cycloalkylalkyl, aryl, arylalkyl, heteroaryl, heteroarylalkyl, heterocycloalkyl or heterocycloalkylalkyl;

each occurrence of $R^6$ and $R^{6'}$ may be the same or different and is independently hydrogen or alkyl; and each occurrence of n is independently an integer from 1-4.

In a preferred distinct embodiment, the invention encompasses a compound of formula (I), wherein:

$R^1$ is pyridine, pyrimidine or thiazole optionally substituted with one amino or methyl group;

$R^2$ is methoxy or 3-morpholin-4-ylpropoxy;

$R^3$ is independently

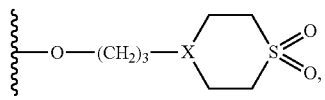

—Y—SO₂—Z or —Y—NH—SO₂—Z;

each occurrence of Y is independently alkoxy, alkoxyalkoxy, or arylalkoxy; and each occurrence of Z is independently methyl, morpholin-4-yl, or dimethylamino.

In another distinct embodiment, the invention encompasses a compound of formula (I), wherein:

N-(8-{3-[(ethylsulfonyl)amino]propoxy}-7-methoxy-2,3-dihydroimidazo[1,2-c]quinazolin-5-yl)nicotinamide;

N-[7-methoxy-8-(2-{2-[(propylsulfonyl)amino]ethoxy}ethoxy)-2,3-dihydroimidazo[1,2-c]quinazolin-5-yl]nicotinamide;

N-[7-methoxy-8-(2-{2-[(phenylsulfonyl)amino]ethoxy}ethoxy)-2,3-dihydroimidazo[1,2-c]quinazolin-5-yl]nicotinamide;

N-[7-methoxy-8-(2-{2-[(methylsulfonyl)amino]ethoxy}ethoxy)-2,3-dihydroimidazo[1,2-c]quinazolin-5-yl]nicotinamide;

N-{7-methoxy-8-[2-(2-{[(4-methylphenyl)sulfonyl]amino}ethoxy)ethoxy]-2,3-dihydroimidazo[1,2-c]quinazolin-5-yl}nicotinamide;

N-{8-[3-(morpholin-4-ylsulfonyl)propoxy]-2,3-dihydroimidazo[1,2-c]quinazolin-5-yl}nicotinamide;

N-(8-{3-[(4-methylpiperazin-1-yl)sulfonyl]propoxy}-2,3-dihydroimidazo[1,2-c]quinazolin-5-yl)nicotinamide;

N-(8-{[4-(methylsulfonyl)benzyl]oxy}-2,3-dihydroimidazo[1,2-c]quinazolin-5-yl)nicotinamide;

2,4-dimethyl-N-(8-{[4-(methylsulfonyl)benzyl]oxy}-2,3-dihydroimidazo[1,2-c]quinazolin-5-yl)-1,3-thiazole-5-carboxamide;

N-{8-[3-(morpholin-4-ylsulfonyl)propoxy]-2,3-dihydroimidazo[1,2-c]quinazolin-5-yl}pyrimidine-5-carboxamide;

2-amino-N-{8-[3-(morpholin-4-ylsulfonyl)propoxy]-2,3-dihydroimidazo[1,2-c]quinazolin-5-yl}pyrimidine-5-carboxamide;

6-amino-N-{8-[3-(morpholin-4-ylsulfonyl)propoxy]-2,3-dihydroimidazo[1,2-c]quinazolin-5-yl}nicotinamide;

N-(7-methoxy-8-{3-[(4-methylpiperazin-1-yl)sulfonyl]propoxy}-2,3-dihydroimidazo[1,2-c]quinazolin-5-yl)nicotinamide;

N-(7-methoxy-8-{[4-(methylsulfonyl)benzyl]oxy}-2,3-dihydroimidazo[1,2-c]quinazolin-5-yl)nicotinamide;

N-{7-methoxy-8-[3-(morpholin-4-ylsulfonyl)propoxy]-2,3-dihydroimidazo[1,2-c]quinazolin-5-yl}nicotinamide;

N-{8-[3-(1,1-dioxidothiomorpholin-4-yl)propoxy]-7-methoxy-2,3-dihydroimidazo[1,2-c]quinazolin-5-yl}nicotinamide;

N-(8-{3-[(diethylamino)sulfonyl]propoxy}-7-methoxy-2,3-dihydroimidazo[1,2-c]quinazolin-5-yl)nicotinamide;

N-(8-{3-[(dimethylamino)sulfonyl]propoxy}-7-methoxy-2,3-dihydroimidazo[1,2-c]quinazolin-5-yl)nicotinamide;

N-{7-[3-(morpholin-4-ylsulfonyl)propoxy]-2,3-dihydroimidazo[1,2-c]quinazolin-5-yl}nicotinamide;

N-(7-{3-[(4-methylpiperazin-1-yl)sulfonyl]propoxy}-2,3-dihydroimidazo[1,2-c]quinazolin-5-yl)nicotinamide;

N-{7-[3-(1,1-dioxidothiomorpholin-4-yl)propoxy]-2,3-dihydroimidazo[1,2-c]quinazolin-5-yl}nicotinamide;

N-(7-{3-[(4-(methylsulfonyl)benzyl]oxy}-2,3-dihydroimidazo[1,2-c]quinazolin-5-yl)nicotinamide;

N-(7-{3-[(dimethylamino)sulfonyl]propoxy}-2,3-dihydroimidazo[1,2-c]quinazolin-5-yl)nicotinamide;

N-{8-(3-morpholin-4-ylpropoxy)-7-[3-(morpholin-4-ylsulfonyl)propoxy]-2,3-dihydroimidazo[1,2-c]quinazolin-5-yl}nicotinamide;

N-[7-{3-[(4-methylpiperazin-1-yl)sulfonyl]propoxy}-8-(3-morpholin-4-ylpropoxy)-2,3-dihydroimidazo[1,2-c]quinazolin-5-yl]nicotinamide;

N-[7-{3-[(diethylamino)sulfonyl]propoxy}-8-(3-morpholin-4-ylpropoxy)-2,3-dihydroimidazo[1,2-c]quinazolin-5-yl]nicotinamide;

N-[7-{3-[(dimethylamino)sulfonyl]propoxy}-8-(3-morpholin-4-ylpropoxy)-2,3-dihydroimidazo[1,2-c]quinazolin-5-yl]nicotinamide;

2-amino-N-(7-methoxy-8-{[4-(methylsulfonyl)benzyl]oxy}-2,3-dihydroimidazo[1,2-c]quinazolin-5-yl)pyrimidine-5-carboxamide;

2-amino-N-(8-{3-[(dimethylamino)sulfonyl]propoxy}-7-methoxy-2,3-dihydroimidazo[1,2-c]quinazolin-5-yl)pyrimidine-5-carboxamide;

6-amino-N-(8-{3-[(dimethylamino)sulfonyl]propoxy}-7-methoxy-2,3-dihydroimidazo[1,2-c]quinazolin-5-yl)nicotinamide;

6-amino-N-{8-[3-(1,1-dioxidothiomorpholin-4-yl)propoxy]-7-methoxy-2,3-dihydroimidazo[1,2-c]quinazolin-5-yl}nicotinamide;

6-amino-N-(7-methoxy-8-{[4-(methylsulfonyl)benzyl]oxy}-2,3-dihydroimidazo[1,2-c]quinazolin-5-yl)nicotinamide;

2-amino-N-{8-[3-(1,1-dioxidothiomorpholin-4-yl)propoxy]-7-methoxy-2,3-dihydroimidazo[1,2-c]quinazolin-5-yl}pyrimidine-5-carboxamide;

6-amino-N-{7-methoxy-8-[3-(morpholin-4-ylsulfonyl)propoxy]-2,3-dihydroimidazo[1,2-c]quinazolin-5-yl}nicotinamide;

2-amino-N-{7-methoxy-8-[3-(morpholin-4-ylsulfonyl)propoxy]-2,3-dihydroimidazo[1,2-c]quinazolin-5-yl}pyrimidine-5-carboxamide;

N-[7-{[4-(methylsulfonyl)benzyl]oxy}-8-(3-morpholin-4-ylpropoxy)-2,3-dihydroimidazo[1,2-c]quinazolin-5-yl]nicotinamide;

8-(3-morpholin-4-ylpropoxy)-5-[(pyridin-3-ylcarbonyl)amino]-2,3-dihydroimidazo[1,2-c]quinazolin-7-yl methanesulfonate;

or a physiologically acceptable salt, solvate, hydrate or stereoisomer thereof.

In another preferred and distinct embodiment, the invention encompasses a compound of formula (I), wherein:

N-{7-methoxy-8-[3-(morpholin-4-ylsulfonyl)propoxy]-2,3-dihydroimidazo[1,2-c]quinazolin-5-yl}nicotinamide;

N-(8-[3-(1,1-dioxidothiomorpholin-4-yl)propoxy]-7-methoxy-2,3-dihydroimidazo[1,2-c]quinazolin-5-yl)nicotinamide;

N-(8-{3-[(dimethylamino)sulfonyl]propoxy}-7-methoxy-2,3-dihydroimidazo[1,2-c]quinazolin-5-yl)nicotinamide;

N-{8-(3-morpholin-4-ylpropoxy)-7-[3-(morpholin-4-ylsulfonyl)propoxy]-2,3-dihydroimidazo[1,2-c]quinazolin-5-yl}nicotinamide;

N-[7-{3-[(dimethylamino)sulfonyl]propoxy}-8-(3-morpholin-4-ylpropoxy)-2,3-dihydroimidazo[1,2-c]quinazolin-5-yl]nicotinamide;

2-amino-N-(8-{3-[(dimethylamino)sulfonyl]propoxy}-7-methoxy-2,3-dihydroimidazo[1,2-c]quinazolin-5-yl)pyrimidine-5-carboxamide;

2-amino-N-{8-[3-(1,1-dioxidothiomorpholin-4-yl)propoxy]-7-methoxy-2,3-dihydroimidazo[1,2-c]quinazolin-5-yl}pyrimidine-5-carboxamide;

N-[7-methoxy-8-(2-{2-[(methylsulfonyl)amino]ethoxy}ethoxy)-2,3-dihydroimidazo[1,2-c]quinazolin-5-yl]nicotinamide;

N-[7-{[4-(methylsulfonyl)benzyl]oxy}-8-(3-morpholin-4-ylpropoxy)-2,3-dihydroimidazo[1,2-c]quinazolin-5-yl]nicotinamide;

or a physiologically acceptable salt, solvate, hydrate or stereoisomer thereof.

Compound names were generated from drawn structures according to IUPAC nomenclature. Where there is a discrepancy between the chemical name and the chemical structure depicted, the chemical structure depicted takes precedence over the chemical name given.

Without being bound by theory or mechanism, the compounds of the present invention display surprising activity for the inhibition of phosphatidylinositol-3-kinase and chemical and structural stability over those compounds of the prior art. It is believed that this surprising activity is based on the chemical structure of the compounds.

Definitions

The term "alkyl" refers to a straight or branched hydrocarbon chain radical consisting solely of carbon and hydrogen atoms, containing no unsaturation, having from one to eight carbon atoms, and which is attached to the rest of the molecule by a single bond, such as illustratively, methyl, ethyl, n-propyl 1-methylethyl (isopropyl), n-butyl, n-pentyl, and 1,1-dimethylethyl (tert-butyl).

The term "alkenyl" refers to an aliphatic hydrocarbon group containing a carbon-carbon double bond and which may be a straight or branched or branched chain having from 2 to 10 carbon atoms, e.g., ethenyl, 1-propenyl, 2-propenyl (allyl), iso-propenyl, 2-methyl-1-propenyl, 1-butenyl, and 2-butenyl.

The term "alkynyl" refers to a straight or branched chain hydrocarbonyl radicals having at least one carbon-carbon triple bond, and having in the range of from 2 to 10 carbon atoms e.g., ethynyl, 1-propynyl, and 2-propynyl.

The term "alkoxy" denotes an alkyl group as defined herein attached via oxygen linkage to the rest of the molecule. Representative examples of those groups are methoxy, ethoxy, propoxy, and isopropoxy.

The term "alkoxyalkyl" denotes an alkoxy group as defined herein attached via oxygen linkage to an alkyl group which is then attached to the main structure at any carbon from alkyl group that results in the creation of a stable structure the rest of the molecule. Representative examples of those groups are —CH$_2$OCH$_3$, —CH$_2$OC$_2$H$_5$.

The term "cycloalkyl" denotes a non-aromatic mono or multicyclic ring system of 3 to 12 carbon atoms such as cyclopropyl, cyclobutyl, cyclopentyl, cyclohexyl and examples of multicyclic cycloalkyl groups include perhydronapthyl, adamantyl and norbornyl groups bridged cyclic group or spirobicyclic groups e.g spiro(4,4)non-2-yl.

The term "cycloalkylalkyl" refers to cyclic ring-containing radicals containing in the range of 3 to 8 carbon atoms directly attached to alkyl group which is then also attached to the main structure at any carbon from the alkyl group that results in the creation of a stable structure such as cyclopropylmethyl, cyclobutylethyl, cyclopentylethyl.

The term "aryl" refers to aromatic radicals having from 6 to 14 carbon atoms such as phenyl, naphthyl, tetrahydronapthyl, indanyl, and biphenyl.

The term "arylalkyl" refers to an aryl group as defined herein directly bonded to an alkyl group as defined herein which is then attached to the main structure at any carbon from alkyl group that results in the creation of a stable structure the rest of the molecule. e.g., —CH$_2$C$_6$H$_5$, —CH$_2$CH$_2$C$_6$H$_5$.

The term "heterocyclic ring" refers to a stable 3- to 15 membered ring radical which consists of carbon atoms and from one to five heteroatoms selected from the group consisting of nitrogen, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofuranyl, carbazolyl cinnolinyl dioxolanyl, indolizinyl, naphthyridinyl, perhydroazepinyl, phenazinyl, phenothiazinyl, phenoxazinyl, phthalazil, pyridyl, pteridinyl, purinyl, quinazolinyl, quinoxalinyl, quinolinyl, isoquinolinyl, tetrazoyl, imidazolyl tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl pyridazinyl, oxazolyl oxazolinyl oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl quinolyl, isoquinolyl, decahydroisoquinolyl, benzimidazolyl, thiadiazolyl, benzopyranyl, benzothiazolyl, benzooxazolyl, furyl, tetrahydrofuryl, tetrahydropyranyl, thienyl, benzothienyl, thiamorpholinyl, thiamorpholinyl sulfoxide, thiamorpholinyl sulfone, oxadiazolyl, chromanyl, and isochromanyl.

The term "heteroaryl" refers to heterocyclic ring radical as defined herein which are aromatic. The heteroaryl ring radical may be attached to the main structure at any heteroatom or carbon atom that results in the creation of a stable structure.

The heterocyclic ring radical may be attached to the main structure at any heteroatom or carbon atom that results in the creation of a stable structure.

The term "heteroarylalkyl" refers to heteroaryl ring radical as defined herein directly bonded to alkyl group. The heteroarylalkyl radical may be attached to the main structure at any carbon atom from alkyl group that results in the creation of a stable structure.

The term "heterocyclyl" refers to a heterocylic ring radical as defined herein. The heterocycyl ring radical may be attached to the main structure at any heteroatom or carbon atom that results in the creation of a stable structure.

The term "heterocyclylalkyl" refers to a heterocylic ring radical as defined herein directly bonded to alkyl group. The heterocyclylalkyl radical may be attached to the main structure at carbon atom in the alkyl group that results in the creation of a stable structure.

The term "carbonyl" refers to an oxygen atom bound to a carbon atom of the molecule by a double bond.

The term "halogen" refers to radicals of fluorine, chlorine, bromine and iodine.

Where the plural form of the word compounds, salts, polymorphs, hydrates, solvates and the like, is used herein, this is taken to mean also a single compound, salt, polymorph, isomer, hydrate, solvate or the like.

The compounds of this invention may contain one or more asymmetric centers, depending upon the location and nature of the various substituents desired. Asymmetric carbon atoms may be present in the (R) or (S) configuration, resulting in racemic mixtures in the case of a single asymmetric center, and diastereomeric mixtures in the case of multiple asymmetric centers. In certain instances, asymmetry may also be present due to restricted rotation about a given bond, for example, the central bond adjoining two substituted aromatic rings of the specified compounds. Substituents on a ring may also be present in either cis or trans form. It is intended that all such configurations (including enantiomers and diastereomers), are included within the scope of the present invention. Preferred compounds are those, which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The present invention also relates to useful forms of the compounds as disclosed herein, such as pharmaceutically acceptable salts, co-precipitates, metabolites, hydrates, solvates and prodrugs of all the compounds of examples. The term "pharmaceutically acceptable salt" refers to a relatively non-toxic, inorganic or organic acid addition salt of a compound of the present invention. For example, see S. M. Berge, et al. "Pharmaceutical Salts," *J. Pharm. Sci.* 1977, 66, 1-19. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, magnesium, ammonium, and chorine salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

Representative salts of the compounds of this invention include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, chloride, bromide, iodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, sulfate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups may be quaternized with such agents as lower alkyl halides such as methyl, ethyl, propyl, or butyl chlorides, bromides and iodides; dialkyl sulfates like dimethyl, diethyl, dibutyl sulfate, or diamyl sulfates, long chain halides such as decyl, lauryl, myristyl and strearyl chlorides, bromides and iodides, aralkyl halides like benzyl and phenethyl bromides and others.

A solvate for the purpose of this invention is a complex of a solvent and a compound of the invention in the solid state. Exemplary solvates would include, but are not limited to, complexes of a compound of the invention with ethanol or methanol. Hydrates are a specific form of solvate wherein the solvent is water.

Pharmaceutical Compositions of the Compounds of the Invention

This invention also relates to pharmaceutical compositions containing one or more compounds of the present invention. These compositions can be utilized to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quaternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitan monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al, "Compendium of Excipients for Parenteral Formulations" *PDA Journal of Pharmaceutical Science & Technology* 1998, 52(5), 238-311; Strickley, R. G "Parenteral Formulations of Small Molecule Therapeutics Marketed in the United States (1999)-Part-1" *PDA Journal of Pharmaceutical Science & Technology* 1999, 53(6), 324-349; and Nema, S. et al, "Excipients and Their Use in Injectable Products" *PDA Journal of Pharmaceutical Science & Technology* 1997, 51(4), 166-171.

Commonly used pharmaceutical ingredients that can be used as appropriate to formulate the composition for its intended route of administration include:
acidifying agents (examples include but are not limited to acetic acid, citric acid, fumaric acid, hydrochloric acid, nitric acid);
alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);
adsorbents (examples include but are not limited to powdered cellulose and activated charcoal);
aerosol propellants (examples include but are not limited to carbon dioxide, $CCl_2F_2$, $F_2ClC—CClF_2$ and $CClF_3$)
air displacement agents (examples include but are not limited to nitrogen and argon);
antifungal preservatives (examples include but are not limited to benzoic acid, butylparaben, ethylparaben, methylparaben, propylparaben, sodium benzoate);
antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);
antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);
binding materials (examples include but are not limited to block polymers, natural and synthetic rubber, polyacrylates, polyurethanes, silicones, polysiloxanes and styrene-butadiene copolymers);
buffering agents (examples include but are not limited to potassium metaphosphate, dipotassium phosphate, sodium acetate, sodium citrate anhydrous and sodium citrate dihydrate)
carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)
chelating agents (examples include but are not limited to edetate disodium and edetic acid)
colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);
clarifying agents (examples include but are not limited to bentonite);
emulsifying agents (examples include but are not limited to acacia, cetomacrogol, cetyl alcohol, glyceryl monostearate, lecithin, sorbitan monooleate, polyoxyethylene 50 monostearate);
encapsulating agents (examples include but are not limited to gelatin and cellulose acetate phthalate)
flavorants (examples include but are not limited to anise oil, cinnamon oil, cocoa, menthol, orange oil, peppermint oil and vanillin);
humectants (examples include but are not limited to glycerol, propylene glycol and sorbitol);
levigating agents (examples include but are not limited to mineral oil and glycerin);
oils (examples include but are not limited to arachis oil, mineral oil, olive oil, peanut oil, sesame oil and vegetable oil);
ointment bases (examples include but are not limited to lanolin, hydrophilic ointment, polyethylene glycol ointment, petrolatum, hydrophilic petrolatum, white ointment, yellow ointment, and rose water ointment);
penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)
plasticizers (examples include but are not limited to diethyl phthalate and glycerol);
solvents (examples include but are not limited to ethanol, corn oil, cottonseed oil, glycerol, isopropanol, mineral oil, oleic acid, peanut oil, purified water, water for injection, sterile water for injection and sterile water for irrigation);
stiffening agents (examples include but are not limited to cetyl alcohol, cetyl esters wax, microcrystalline wax, paraffin, stearyl alcohol, white wax and yellow wax);
suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);
suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);
sweetening agents (examples include but are not limited to aspartame, dextrose, glycerol, mannitol, propylene glycol, saccharin sodium, sorbitol and sucrose);
tablet anti-adherents (examples include but are not limited to magnesium stearate and talc);
tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);
tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);
tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);
tablet direct compression excipients (examples include but are not limited to dibasic calcium phosphate);
tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);
tablet glidants (examples include but are not limited to colloidal silica, corn starch and talc);
tablet lubricants (examples include but are not limited to calcium stearate, magnesium stearate, mineral oil, stearic acid and zinc stearate);
tablet/capsule opaquants (examples include but are not limited to titanium dioxide);
tablet polishing agents (examples include but are not limited to carnuba wax and white wax);
thickening agents (examples include but are not limited to beeswax, cetyl alcohol and paraffin);
tonicity agents (examples include but are not limited to dextrose and sodium chloride);
viscosity increasing agents (examples include but are not limited to alginic acid, bentonite, carbomers, carboxymethylcellulose sodium, methylcellulose, polyvinyl pyrrolidone, sodium alginate and tragacanth); and
wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:
Sterile IV Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.
Lyophilized powder for IV administration: A sterile preparation can be prepared with (i) 100-1000 mg of the desired compound of this invention as a lyophilized powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.
Intramuscular suspension: The following solution or suspension can be prepared, for intramuscular injection:
50 mg/mL of the desired, water-insoluble compound of this invention
5 mg/mL sodium carboxymethylcellulose
4 mg/mL TWEEN 80
9 mg/mL sodium chloride
9 mg/mL benzyl alcohol
Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.
Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.
Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.
Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant kinase activity (such as tyrosine kinase activity), including, phosphotidylinositol-3-kinase.

Effective amounts of compounds of the present invention can be used to treat disorders, including angiogenic disorders, such as cancer; inflammatory disorders (including but not limited to Chronic obstructive pulmonary disorder (COPD)), autoimmune disorders, cardiovascular disorders (including but not limited to thrombosis, pulmonary hypertension, cardiac hypertrophy, atherosclerosis or heart failure), neurodegenerative disorders, metabolic disorders, nociceptive disorders, ophthalmic disorders, pulmonary disorders, or renal disorders. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of phosphotidylinositol-3-kinase, comprising administering an effective amount of a compound of the present invention, including salts, polymorphs, metabolites, hyrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity (Aiello et al. *New Engl. J. Med.* 1994, 331, 1480; Peer et al. *Lab. Invest.* 1995, 72, 638), age-related macular degeneration (AMD; see, Lopez et al. *Invest. Opththalmol. Vis. Sci.* 1996, 37, 855), neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumor enlargement and metastasis. Moreover, the growth of new blood and lymph vessels in a tumor provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Dose and Administration

Based upon standard laboratory techniques known to evaluate compounds useful for the treatment of hyper-proliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated. The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Combination Therapies

The compounds of this invention can be administered as the sole pharmaceutical agent or in combination with one or more other pharmaceutical agents where the combination causes no unacceptable adverse effects. For example, the compounds of this invention can be combined with known anti-hyper-proliferative, antiinflammatory, analgesic, immunoregulatory, diuretic, antiarrhytmic, anti-hypercholsterolemia, anti-dyslipidemia, anti-diabetic or antiviral agents, and the like, as well as with admixtures and combinations thereof.

The additional pharmaceutical agent can be aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, argiabin, arsenic trioxide, aromasin, 5-azacytidine, azathioprine, BCG or tice BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidine, chlorambucil, cisplatin, cladribine, cladribine, clodronic acid, cyclophosphamide, cytarabine, dacarbazine, dactinomycin, DaunoXome, decadron, decadron phosphate, delestrogen, denileukin diftitox, depo-medrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin alfa, epogen, eptaplatin, ergamisol, estrace, estradiol, estramustine phosphate sodium, ethinyl estradiol, ethyol, etidronic acid, etopophos, etoposide, fadrozole, farston, filgrastim, finasteride, fligrastim, floxuridine, fluconazole, fludarabine, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, goserelin, granisetron HCl, histrelin, hycamtin, hydrocortone, eyrthro-hydroxynonyladenine, hydroxyurea, ibritumomab tiuxetan, idarubicin, ifosfamide, interferon alpha, interferon-alpha 2, interferon alfa-2A, interferon alfa-2B, interferon alfa-n1, interferon alfa-n3, interferon beta, interferon gamma-1a, interleukin-2, intron A, iressa, irinotecan, kytril, lentinan sulphate, letrozole, leucovorin, leuprolide, leuprolide acetate, levamisole, levofolinic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, Mesna, methotrexate, metvix, miltefosine, minocycline, mitomycin C, mitotane, mitoxantrone, Modrenal, Myocet, nedaplatin, neulasta, neumega, neupogen, nilutamide, nolvadex, NSC-631570, OCT-43, octreotide, ondansetron HCl, orapred, oxaliplatin, paclitaxel, pediapred, pegaspargase, Pegasys, pentostatin, picibanil, pilocarpine HCl, pirarubicin, plicamycin, porfimer sodium, prednimustine, prednisolone, prednisone, premarin, procarbazine, procrit, raltitrexed, rebif, rhenium-186 etidronate, rituximab, roferon-A, romurtide, salagen, sandostatin, sargramostim, semustine, sizofuran, sobuzoxane, solu-medrol, sparfosic acid, stem-cell therapy, streptozocin, strontium-89 chloride, synthroid, tamoxifen, tamsulosin, tasonermin, tastolactone, taxotere, teceleukin, temozolomide, teniposide, testosterone propionate, testred, thioguanine, thiotepa, thyrotropin, tiludronic acid, topotecan, toremifene, tositumomab, trastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, zofran, ABI-007, acolbifene, actimmune, affinitak, aminopterin, arzoxifene, asoprisnil, atamestane, atrasentan, sorafenib, avastin, CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon gamma, intron-PEG, ixabepilone, keyhole limpet hemocyanin, L-651582, lanreotide, lasofoxifene, libra, lonafarnib, miproxifene, minodronate, MS-209, liposomal MTP-PE, MX-6, nafarelin, nemorubicin, neovastat, nolatrexed, oblimersen, onco-TCS, osidem, paclitaxel polyglutamate, pamidronate disodium, PN-401, QS-21, quazepam, R-1549, raloxifene, ranpirnase, 13-cis-retinoic acid, satraplatin, seocalcitol, T-138067, tarceva, taxoprexin, thymosin alpha 1, tiazofurine, tipifarnib, tirapazamine, TLK-286, toremifene, TransMID-107R, valspodar, vapreotide, vatalanib, verteporfin, vinflunine, Z-100, zoledronic acid or combinations thereof.

The additional pharmaceutical agent can also be gemcitabine, paclitaxel, cisplatin, carboplatin, sodium butyrate, 5-FU, doxirubicin, tamoxifen, etoposide, trastumazab, gefitinib, intron A, rapamycin, 17-AAG, U0126, insulin, an insulin derivative, a PPAR ligand, a sulfonylurea drug, an α-glucosidase inhibitor, a biguanide, a PTP-1B inhibitor, a DPP-IV inhibitor, a 11-beta-HSD inhibitor, GLP-1, a GLP-1 derivative, GIP, a GIP derivative, PACAP, a PACAP derivative, secretin or a secretin derivative.

Optional anti-hyper-proliferative agents which can be added to the composition include but are not limited to compounds listed on the cancer chemotherapy drug regimens in the 11$^{th}$ Edition of the *Merck Index*, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use with the composition of the invention include but are not limited to those compounds acknowledged to be used in the treatment of neoplastic diseases in *Goodman and Gilman's The Pharmacological Basis of Therapeutics* (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use with the composition of the invention include but are not limited to other anti-cancer agents such as epothilone and its derivatives, irinotecan, raloxifen and topotecan.

Generally, the use of cytotoxic and/or cytostatic agents in combination with a compound or composition of the present invention will serve to:
(1) yield better efficacy in reducing the growth of a tumor or even eliminate the tumor as compared to administration of either agent alone,
(2) provide for the administration of lesser amounts of the administered chemo-therapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

EXPERIMENTAL

Abbreviations and Acronyms

A comprehensive list of the abbreviations used by organic chemists of ordinary skill in the art appears in The ACS Style Guide (third edition) or the Guidelines for Authors for the *Journal of Organic Chemistry*. The abbreviations contained in said lists, and all abbreviations utilized by organic chemists of ordinary skill in the art are hereby incorporated by reference. For purposes of this invention, the chemical elements are identified in accordance with the Periodic Table of the Elements, CAS version, Handbook of Chemistry and Physics, 67th Ed., 1986-87.

More specifically, when the following abbreviations are used throughout this disclosure, they have the following meanings:

| | |
|---|---|
| acac | acetylacetonate |
| $Ac_2O$ | acetic anhydride |
| AcO (or OAc) | acetate |
| anhyd | anhydrous |
| aq | aqueous |
| Ar | aryl |
| atm | atmosphere |
| 9-BBN | 9-borabicyclo[3.3.1]nonyl |
| BINAP | 2,2'-bis(diphenylphosphino)-1,1'-binaphthyl |
| Bn | benzyl |
| bp | boiling point |
| br s | broad singlet |
| Bz | benzoyl |
| BOC | tert-butoxycarbonyl |
| n-BuOH | n-butanol |
| t-BuOH | tert-butanol |
| t-BuOK | potassium tert-butoxide |
| C | Celsius |
| calcd | calculated |
| CAN | ceric ammonium nitrate |
| Cbz | carbobenzyloxy |
| CDI | carbonyl diimidazole |
| $CD_3OD$ | methanol-$d_4$ |
| Celite ® | diatomaceous earth filter agent, Celite ® Corp. |
| CI-MS | chemical ionization mass spectroscopy |
| $^{13}C$ NMR | carbon-13 nuclear magnetic resonance |
| m-CPBA | meta-chloroperoxybenzoic acid |
| d | doublet |
| dd | doublet of doublets |
| DABCO | 1,4-diazabicyclo[2.2.2]octane |
| DBU | 1,8-diazabicyclo[5.4.0]undec-7-ene |
| DCC | N,N'-dicyclohexylcarbodiimide |
| DCM | dichloromethane |
| DEAD | diethyl azodicarboxylate |
| dec | decomposition |
| DIA | diisopropylamine |
| DIBAL | diisobutylaluminum hydride |
| DMAP | 4-(N,N-dimethylamino)pyridine |
| DME | 1,2-dimethoxyethane |
| DMF | N,N-dimethylformamide |
| DMSO | dimethylsulfoxide |
| E | entgegen (configuration) |
| EDCI or EDCI•HCl | 1-(3-dimethylaminopropyl)-3-ethylcarbodiimide hydrochloride |
| ee | enantiomeric excess |
| EI | electron impact |
| ELSD | evaporative light scattering detector |
| equiv | equivalent |
| ES-MS | electrospray mass spectroscopy |
| EtOAc | ethyl acetate |
| EtOH | ethanol (100%) |
| EtSH | ethanethiol |
| $Et_2O$ | diethyl ether |
| $Et_3N$ | triethylamine |
| Fmoc | 9-fluorenylmethoxycarbonyl |
| GC | gas chromatography |
| GC-MS | gas chromatography-mass spectroscopy |
| h | hour, hours |
| hex | hexanes, or hexane |
| $^1H$ NMR | proton nuclear magnetic resonance |
| HMPA | hexamethylphosphoramide |
| HMPT | hexamethylphosphoric triamide |
| HOBT | hydroxybenzotriazole |
| HPLC | high performance liquid chromatography |
| insol | insoluble |
| IPA | isopropylamine |
| iPrOH | isopropylalcohol |
| IR | infrared |
| J | coupling constant (NMR spectroscopy) |
| L | liter |
| LAH | lithium aluminum hydride |
| LC | liquid chromatography |
| LC-MS | liquid chromatography-mass spectrometry |
| LDA | lithium diisopropylamide |
| M | mol $L^{-1}$ (molar) |
| m | multiplet |
| m | meta |
| MeCN | acetonitrile |
| MeOH | methanol |
| MHz | megahertz |
| min | minute, minutes |

| | |
|---|---|
| μL | microliter |
| mL | milliliter |
| μM | micromolar |
| mol | mole |
| mp | melting point |
| MS | mass spectrum, mass spectrometry |
| Ms | methanesulfonyl |
| m/z | mass-to-charge ratio |
| N | equiv $L^{-1}$ (normal) |
| NBS | N-bromosuccinimide |
| nM | nanomolar |
| NMM | 4-methylmorpholine |
| NMR | Nuclear Magnetic Resonance |
| o | ortho |
| obsd | observed |
| p | para |
| p | page |
| pp | pages |
| PdCl$_2$dppf | [1,1'-bis(diphenylphosphino)ferrocene]dichloropalladium(II) |
| Pd(OAc)$_2$ | palladium acetate |
| pH | negative logarithm of hydrogen ion concentration |
| Ph | phenyl |
| pK | negative logarithm of equilibrium constant |
| pK$_a$ | negative logarithm of equilibrium constant for association |
| PPA | poly(phosphoric acid) |
| PS-DIEA | Polystyrene-bound diisopropylethylamine |
| PyBOP | benzotriazole-1-yl-oxy-tris-pyrrolidino-phosphonium hexafluorophosphate |
| q | quartet |
| rac | racemic |
| R | rectus (configurational) |
| R$_f$ | retardation factor (TLC) |
| RT | retention time (HPLC) |
| rt | room temperature |
| s | singlet |
| S | sinister (configurational) |
| t | triplet |
| TBDMS, TBP | tert-butyldimethylsilyl |
| TBDPS, TPS | tert-butyldiphenylsilyl |
| TEA | triethylamine |
| THF | tetrahydrofuran |
| Tf | trifluoromethanesulfonyl (triflyl) |
| TFA | trifluoroacetic acid |
| TFFH | Fluoro-N,N,N',N'-tetramethylformamidinium hexafluorophosphate |
| TLC | thin layer chromatography |
| TMAD | N,N,N',N'-tetramethylethylenediamine |
| TMSCl | trimethylsilyl chloride |
| Ts | p-toluenesulfonyl |
| v/v | volume to volume ratio |
| w/v | weight to volume ratio |
| w/w | weight to weight ratio |
| Z | zusammen (configuration) |

The percentage yields reported in the following examples are based on the starting component that was used in the lowest molar amount. Air and moisture sensitive liquids and solutions were transferred via syringe or cannula, and introduced into reaction vessels through rubber septa. Commercial grade reagents and solvents were used without further purification. The term "concentrated under reduced pressure" refers to use of a Buchi rotary evaporator at approximately 15 mm of Hg. All temperatures are reported uncorrected in degrees Celsius (° C.). Thin layer chromatography (TLC) was performed on pre-coated glass-backed silica gel 60 A F-254 250 μm plates.

The structures of compounds of this invention were confirmed using one or more of the following procedures.

NMR

NMR spectra were acquired for each compound and were consistent with the structures shown.

Routine one-dimensional NMR spectroscopy was performed on either 300 or 400 MHz Varian® Mercury-plus spectrometers. The samples were dissolved in deuterated solvents. Chemical shifts were recorded on the ppm scale and were referenced to the appropriate solvent signals, such as 2.49 ppm for DMSO-d6, 1.93 ppm for CD3CN, 3.30 ppm for CD3OD, 5.32 ppm for CD2Cl2 and 7.26 ppm for CDCl3 for $^1$H NMR spectra.

GC/MS

Electron impact mass spectra (EI-MS) were obtained with a Hewlett Packard 5973 mass spectrometer equipped Hewlett Packard 6890 Gas Chromatograph with a J & W HP-5 column (0.25 uM coating; 30 m×0.32 mm). The ion source was maintained at 250° C. and spectra were scanned from 50-550 amu at 0.34 sec per scan.

LC/MS

Unless otherwise noted, all retention times are obtained from the LC/MS and correspond to the molecular ion. High pressure liquid chromatography-electrospray mass spectra (LC/MS) were obtained using one of the following:

Method A (LCQ)

Hewlett-Packard 1100 HPLC equipped with a quaternary pump, a variable wavelength detector set at 254 nm, a Waters Sunfire C18 column (2.1×30 mm, 3.5 □m), a Gilson autosampler and a Finnigan LCQ ion trap mass spectrometer with electrospray ionization. Spectra were scanned from 120-1200 amu using a variable ion time according to the number of ions in the source. The eluents were A: 2% acetonitrile in water with 0.02% TFA, and B: 2% water in acetonitrile with 0.018% TFA. Gradient elution from 10% B to 95% B over 3.5 minutes at a flow rate of 1.0 mL/min was used with an initial hold of 0.5 minutes and a final hold at 95% B of 0.5 minutes. Total run time was 6.5 minutes.

Method B (LCQ5)

Agilent 1100 HPLC system. The Agilent 1100 HPLC system was equipped with an Agilent 1100 autosampler, quaternary pump, a variable wavelength detector set at 254 nm. The HPLC column used was a Waters Sunfire C-18 column (2.1×30 mm, 3.5 μm). The HPLC eluent was directly coupled without splitting to a Finnigan LCQ DECA ion trap mass spectrometer with electrospray ionization. Spectra were scanned from 140-1200 amu using a variable ion time according to the number of ions in the source using positive ion mode. The eluents were A: 2% acetonitrile in water with 0.02% TFA, and B: 2% water in acetonirile with 0.02% TFA. Gradient elution from 10% B to 90% B over 3.0 minutes at a flow rate of 1.0 mL/min was used with an initial hold of 1.0 minutes and a final hold at 95% B of 1.0 minutes. Total run time was 7.0 minutes.

Method C (LTQ)

Agilent 1100 HPLC system. The Agilent 1100 HPLC system was equipped with an Agilent 1100 autosampler, quaternary pump, and a diode array. The HPLC column used was a Waters Sunfire C18 column (2.1×30 mm, 3.5 μm). The HPLC eluent was directly coupled with a 1:4 split to a Finnigan LTQ ion trap mass spectrometer with electrospray ionization. Spectra were scanned from 50-800 amu using a variable ion time according to the number of ions in the source using positive or negative ion mode. The eluents were A: water with 0.1 formic acid, and B: acetonitrile with 0.1% formic acid. Gradient elution from 10% B to 90% B over 3.0 minutes at a flowrate of 1.0 mL/min was used with an initial hold of 2.0 minutes and a final hold at 95% B of 1.0 minutes. Total run time was 8.0 minutes.

Method D

Gilson HPLC system equipped with a variable wavelength detector set at 254 nm; a YMC pro C-18 column (2×23 mm, 120A), and a Finnigan LCQ ion trap mass spectrometer with electrospray ionization. Spectra were scanned from 120-1200 amu using a variable ion time according to the number of ions in the source. The eluants were A: 2% acetonitrile in water with 0.02% TFA and B: 2% water in acetonitrile with 0.018% TFA. Gradient elution from 10% B to 95% over 3.5 minutes at a flow rate of 1.0 mL/min was used with an initial hold of 0.5 minutes and a final hold at 95% B of 0.5 minutes. Total run time was 6.5 minutes.

Method E

Agilent 1100 HPLC system. The Agilent 1100 HPLC system was equipped with an Agilent 1100 autosampler, quaternary pump, and a diode array. The HPLC column used was a Waters Sunfire (2.1×30 mm, 3.5 μm). The HPLC eluent was directly coupled with a 1:4 split to a Finnigan LTQ ion trap mass spectrometer with electrospray ionization. Spectra were scanned from 50-1000 amu using a variable ion time according to the number of ions in the source in either positive or negative ion mode. The eluents were A: water with 0.1 formic acid, and B: acetonitrile with 0.1% formic acid. Gradient elution from 10% B to 90% B over 3.0 minutes at a flow rate of 1.0 mL/min was used with an initial hold of 2.0 minutes and a final hold at 95% B of 1.0 minutes. Total run time was 8.0 minutes.

Preparative HPLC:

Preparative HPLC was carried out in reversed phase mode, typically using a Gilson HPLC system equipped with two Gilson 322 pumps, a Gilson 215 Autosampler, a Gilson diode array detector, and a C-18 column (e.g. YMC Pro 20×150 mm, 120 A). Gradient elution was used with solvent A as water with 0.1% TFA, and solvent B as acetonitrile with 0.1% TFA. Following injection onto the column as a solution, the compound was typically eluted with a mixed solvent gradient, such as 10-90% Solvent B in Solvent A over 15 minutes with flow rate of 25 mL/min. The fraction(s) containing the desired product were collected by UV monitoring at 254 or 220 nm.

Preparative MPLC:

Preparative medium pressure liquid chromatography (MPLC) was carried out by standard silica gel "flash chromatography" techniques (e.g., Still, W. C. et al. *J. Org. Chem.* 1978, 43, 2923-5), or by using silica gel cartridges and devices such as the Biotage Flash systems. A variety of eluting solvents were used, as described in the experimental protocols.

General Preparative Methods

The particular process to be utilized in the preparation of the compounds used in this embodiment of the invention depends upon the specific compound desired. Such factors as the selection of the specific substituents play a role in the path to be followed in the preparation of the specific compounds of this invention. Those factors are readily recognized by one of ordinary skill in the art.

The compounds of the invention may be prepared by use of known chemical reactions and procedures. Nevertheless, the following general preparative methods are presented to aid the reader in synthesizing the compounds of the present invention, with more detailed particular examples being presented below in the experimental section describing the working examples.

The compounds of the invention can be made according to conventional chemical methods, and/or as disclosed below, from starting materials which are either commercially available or producible according to routine, conventional chemical methods. General methods for the preparation of the compounds are given below, and the preparation of representative compounds is specifically illustrated in examples.

Synthetic transformations that may be employed in the synthesis of compounds of this invention and in the synthesis of intermediates involved in the synthesis of compounds of this invention are known by or accessible to one skilled in the art. Collections of synthetic transformations may be found in compilations, such as:

J. March. *Advanced Organic Chemistry,* 4th ed.; John Wiley: New York (1992) R. C. Larock. *Comprehensive Organic Transformations,* 2nd ed.; Wiley-VCH: New York (1999);

F. A. Carey; R. J. Sundberg. *Advanced Organic Chemistry,* 2nd ed.; Plenum Press: New York (1984);

T. W. Greene; P. G. M. Wuts. *Protective Groups in Organic Synthesis,* 3rd ed.; John Wiley: New York (1999);

L. S. Hegedus. *Transition Metals in the Synthesis of Complex Organic Molecules,* 2nd ed.; University Science Books: Mill Valley, Calif. (1994);

L. A. Paquette, Ed. *The Encyclopedia of Reagents for Organic Synthesis*; John Wiley: New York (1994);

A. R. Katritzky; O. Meth-Cohn; C. W. Rees, Eds. *Comprehensive Organic Functional Group Transformations*; Pergamon Press: Oxford, UK (1995);

G. Wilkinson; F. G A. Stone; E. W. Abel, Eds. *Comprehensive Organometallic Chemistry*; Pergamon Press: Oxford, UK (1982);

B. M. Trost; I. Fleming. *Comprehensive Organic Synthesis*; Pergamon Press: Oxford, UK (1991);

A. R. Katritzky; C. W. Rees Eds. *Comprehensive Heterocylic Chemistry*, Pergamon Press: Oxford, UK (1984);

A. R. Katritzky; C. W. Rees; E. F. V. Scriven, Eds. *Comprehensive Heterocyclic Chemistry II*; Pergamon Press: Oxford, UK (1996); and C. Hansch; P. G. Sammes; J. B. Taylor, Eds. *Comprehensive Medicinal Chemistry*. Pergamon Press: Oxford, UK (1990), each of which are incorporated by reference.

In addition, recurring reviews of synthetic methodology and related topics include *Organic Reactions*; John Wiley: New York; *Organic Syntheses*; John Wiley: New York; *Reagents for Organic Synthesis*: John Wiley: New York; *The Total Synthesis of Natural Products*; John Wiley: New York; *The Organic Chemistry of Drug Synthesis*; John Wiley: New York; *Annual Reports in Organic Synthesis*; Academic Press: San Diego Calif.; and *Methoden der Organischen Chemie* (Houben-Weyl); Thieme: Stuttgart, Germany. Furthermore, databases of synthetic transformations include Chemical Abstracts, which may be searched using either CAS OnLine or SciFinder, *Handbuch der Organischen Chemie* (Beilstein), which may be searched using SpotFire, and REACCS.

Reaction Scheme 1

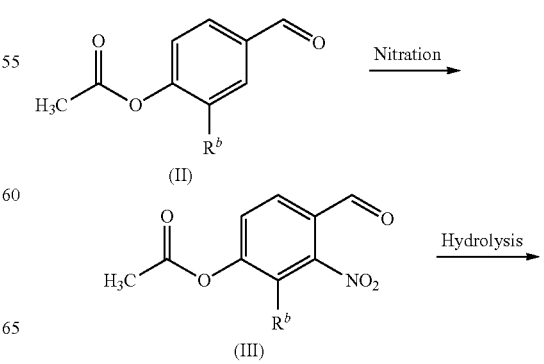

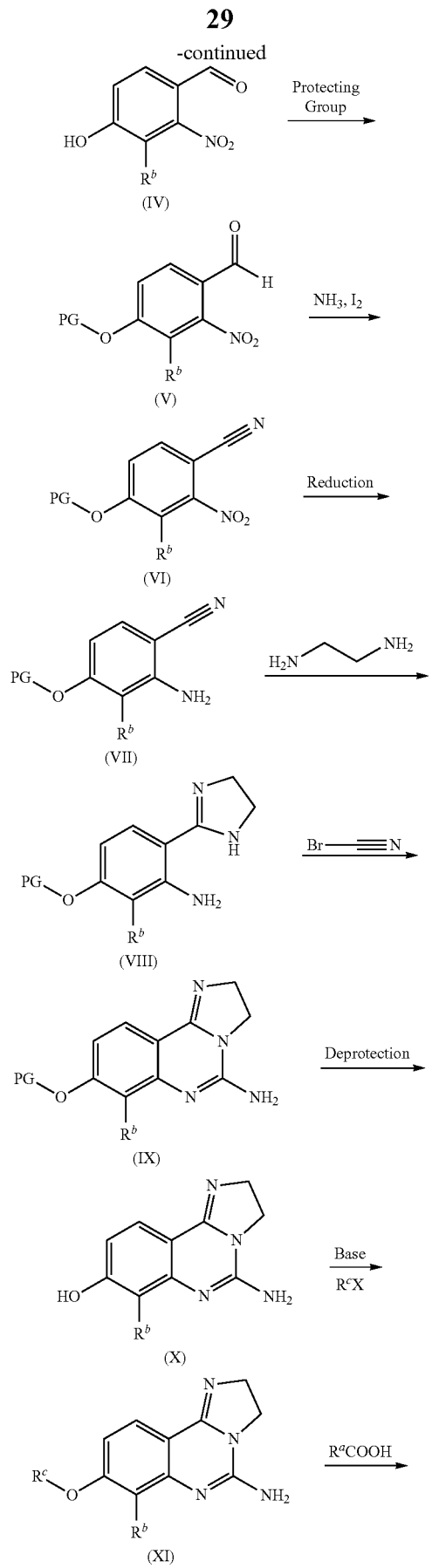

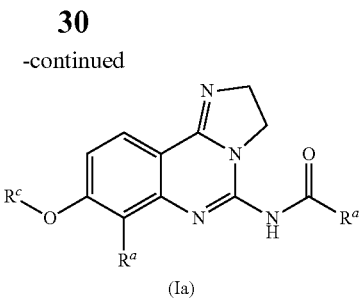

(Ia)

As shown in Reaction Scheme 1, vanillin acetate can be converted to intermediate (III) via nitration conditions such as neat fuming nitric acid. Hydrolysis of the acetate in intermediate (III) occurs in the presence of bases such as sodium hydroxide, lithium hydroxide, or potassium hydroxide in a protic solvent such as methanol. Protection of intermediate (IV) to generate compounds of Formula (V) could be accomplished by standard methods (Greene, T. W.; Wuts, P. G. M.; *Protective Groups in Organic Synthesis*; Wiley & Sons: New York, 1999). Conversion of compounds of formula (V) to those of formula (VI) can be achieved using ammonia in the presence of iodine in an aprotic solvent such as THF or dioxane. Reduction of the nitro group in formula (VI) can be accomplished using iron in acetic acid or hydrogen gas in the presence of a suitable palladium, platinum or nickel catalyst. Conversion of compounds of formula (VII) to imidazoline (VIII) is accomplished using ethylenediamine in the presence of a catalyst such as elemental sulfur with heating. The cyclization of compounds of formula (VIII) to those of formula (IX) is accomplished using cyanogen bromide in the presence of an amine base such as triethylamine, diisopropylethylamine, or pyridine in a halogenated solvent such as DCM or dichloroethane. Removal of the protecting group in formula (IX) will be dependent on the group selected and can be accomplished by standard methods (Greene, T. W.; Wuts, P. G. M.; *Protective Groups in Organic Synthesis*; Wiley & Sons: New York, 1999). Alkylation of the phenol in formula (X) can be achieved using a base such as cesium carbonate, sodium hydride, or potassium tert-butoxide in a polar aprotic solvent such as DMF or DMSO with introduction of a side chain bearing an appropriate leaving group such as a halide, or a sulfonate group. Lastly, amides of formula (Ia) can be formed using activated esters such as acid chlorides and anhydrides or alternatively formed using carboxylic acids and appropriate coupling agents such as PYBOP, DCC, or EDCI in polar aprotic solvents.

Reaction Scheme 2

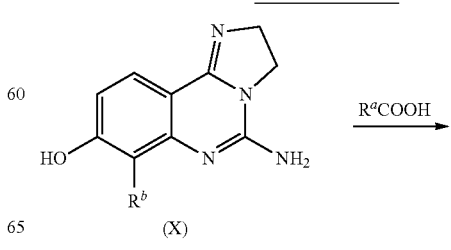

(X)

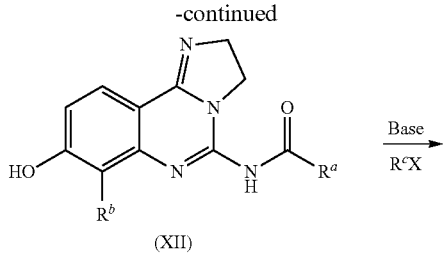

(XII)

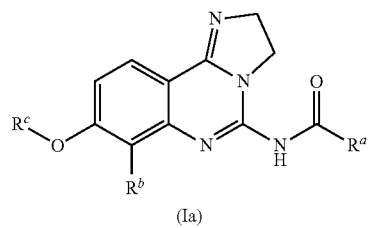

(Ia)

As shown in Reaction Scheme 2, a compound of formula (X), prepared as described above, can be converted to amide (XII) using activated esters such as acid chlorides and anhydrides or alternatively formed using carboxylic acids and appropriate coupling agents such as PYBOP, DCC, or EDCI in polar aprotic solvents. This could then be converted to compounds of formula (Ia) using a base such as cesium carbonate, sodium hydride, or potassium tert-butoxide in a polar aprotic solvent such as DMF or DMSO with introduction of a side chain bearing an appropriate leaving group such as a halide, or a sulfonate group.

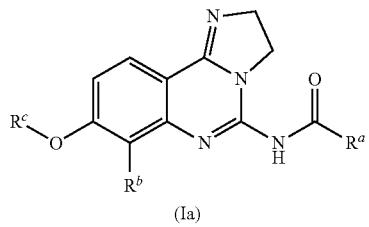

(Ia)

As shown in Reaction Scheme 3, a compound of formula (IX), prepared as described above, can be converted to amide (XIII) using activated esters such as acid chlorides and anhydrides or alternatively formed using carboxylic acids and appropriate coupling agents such as PYBOP, DCC, or EDCI in polar aprotic solvents. Removal of the protecting group in formula (XIII) will be dependent on the group selected and can be accomplished by standard methods (Greene, T. W.; Wuts, P. G. M.; *Protective Groups in Organic Synthesis*; Wiley & Sons: New York, 1999). Alkylation of the phenol in formula (XIV) to prepare compounds of formula (Ia) can be achieved using a base such as cesium carbonate, sodium hydride, or potassium tert-butoxide in a polar aprotic solvent such as DMF or DMSO with introduction of a side chain bearing an appropriate leaving group such as a halide, or a sulfonate group.

Reaction Scheme 3

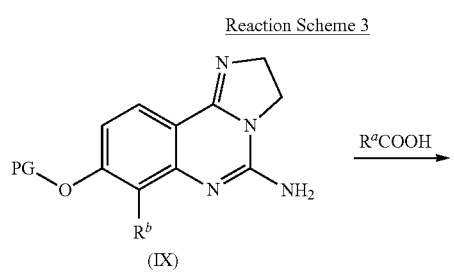

(IX)

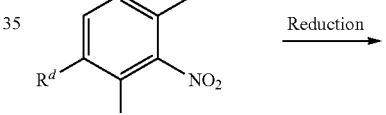

Reaction Scheme 4

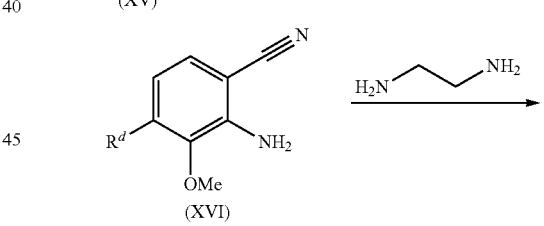

(XV)

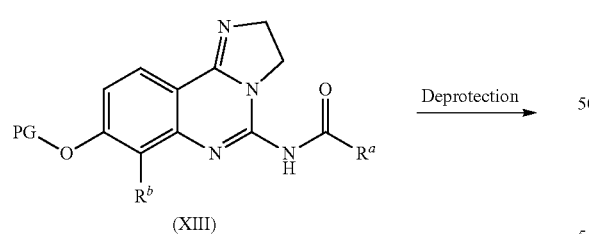

(XIII)

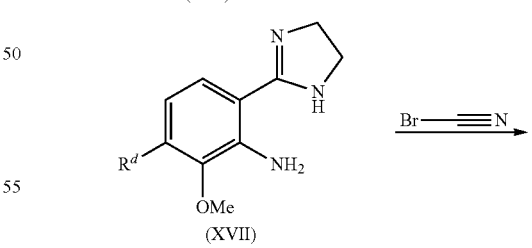

(XVI)

(XVII)

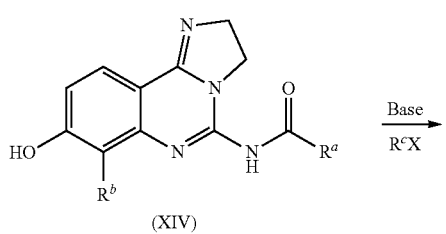

(XIV)

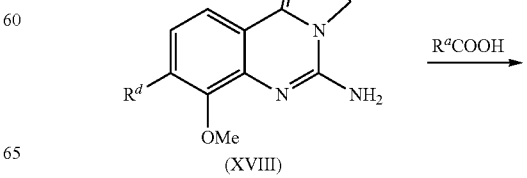

(XVIII)

33

-continued

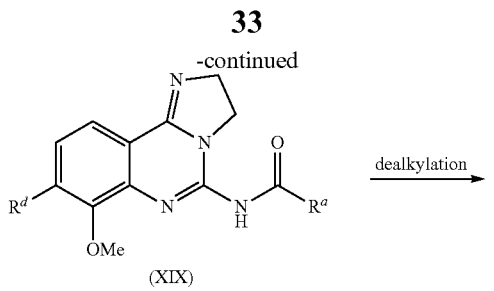

(XIX)

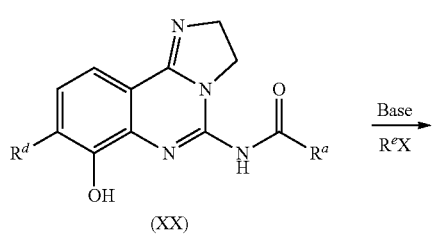

(XX)

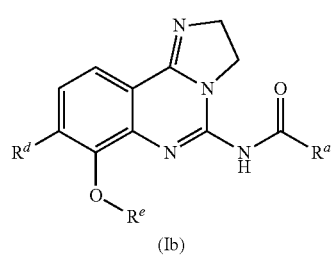

(Ib)

As shown in Reaction Scheme 4, a compound of formula (XV) can be converted to a structure of formula (XIX) using analogous steps as described above. Phenolic compounds of formula (XX) can be formed by demethylation using sodium sulfide in polar aprotic solvents such as NMP or DMSO. Alkylation of the phenol in formula (XX) to prepare compounds of formula (Ib) can be achieved using a base such as cesium carbonate, sodium hydride, or potassium tert-butoxide in a polar aprotic solvent such as DMF or DMSO with introduction of a side chain bearing an appropriate leaving group such as a halide, or a sulfonate group.

INTERMEDIATES

Intermediate A: Preparation of 5-amino-7-methoxy-2,3-dihydroimidazo[1,2-c]quinazolin-8-ol bis(trifluoroacetate)

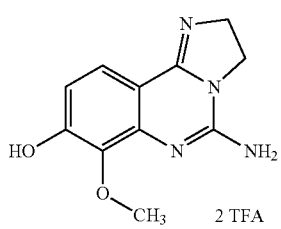 [SMILES: COc1c(O)ccc2c1N=C(N)N1CCN=C21]

34

Step 1: Preparation of 4-formyl-2-methoxy-3-nitrophenyl acetate

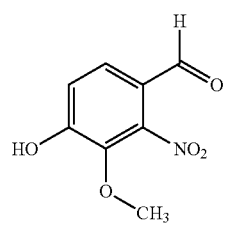

Fuming nitric acid (2200 mL) under nitrogen was cooled to 0° C. at which time vanillin acetate (528 g, 2.7 mol) was added portionwise, keeping the internal temperature below 10° C. After 2 h the resulting mixture was poured over ice with stirring. The slurry was filtered and the resulting solids were washed with water (3×100 mL) and air-dried. After 2 days the solids were heated in DCM (3000 mL) until complete dissolution. The solution was allowed to cool to room temperature while hexanes (3000 mL) was added dropwise. The solids were filtered, washed with hexanes (500 mL) and air dried to give the desired product (269 g, 41%): $^1$H NMR, (DMSO-$d_6$) δ: 9.90 (s, 1H), 7.94 (d, 1H), 7.75 (d, 1H), 3.87 (s, 3H), 2.40 (s, 3H).

Step 2: Preparation of 4-hydroxy-3-methoxy-2-nitrobenzaldehyde

A mixture of 4-formyl-2-methoxy-3-nitrophenyl acetate (Step 1, 438 g, 1.8 mol) and potassium carbonate (506 g, 3.7 mol) in MeOH (4000 mL) was stirred at room temperature for 16 h. The reaction mixture was concentrated under reduced pressure to afford a viscous oil. This was dissolved in water, acidified using a solution of HCl (2 N) and extracted with EtOAc. The organic layer was washed with brine, dried (MgSO$_4$) and filtered. The solvent was concentrated under reduced pressure to ⅓ volume and the resulting solids were filtered and air-dried to give the title compound (317 g, 88%): ¹H NMR (DMSO-d₆) δ: 9.69 (1H, s), 7.68 (1H, d), 7.19 (1H, d), 3.82 (3H, s).

Step 3: Preparation of
4-(benzyloxy)-3-methoxy-2-nitrobenzaldehyde

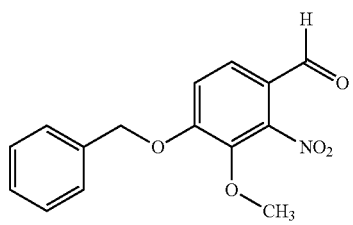 [SMILES: COc1c(OCc2ccccc2)ccc(C=O)c1[N+](=O)[O-]]

4-Hydroxy-3-methoxy-2-nitrobenzaldehyde (Step 2, 155 g, 786 mmol) was dissolved in DMF (1500 mL) and the stirred solution was treated with potassium carbonate (217 g, 1.57 mol) followed by benzyl bromide (161 g, 0.94 mol). After stirring for 16 h the reaction mixture was concentrated under reduced pressure and separated between water (2 L) and EtOAc (2 L). The organic layer was washed with brine (3×2 L), dried (sodium sulfate) and concentrated under reduced pressure. The resulting solids were triturated with Et₂O (1 L) to give the title compound (220 g, 97%): ¹H NMR (DMSO-d₆) δ: 9.77 (1H, s), 7.87 (1H, d), 7.58 (1H, d), 7.51 (1H, m), 7.49 (1H, m), 7.39 (3H, m), 5.36 (2H, s), 3.05 (3H, s).

Step 4: Preparation of
4-(benzyloxy)-3-methoxy-2-nitrobenzonitrile

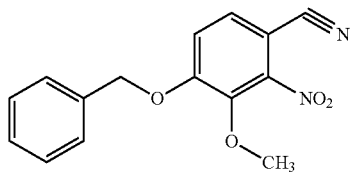

Iodine (272 g, 1.1 mmol) was added to a mixture of 4-(benzyloxy)-3-methoxy-2-nitrobenzaldehyde (Step 3, 220 g, 766 mmol) and ammonium hydroxide (28% solution, 3 L) dissolved in THF (5 L). After 16 h the reaction mixture was treated with sodium sulfite (49 g, 383 mmol) and concentrated under reduced pressure to afford a thick slurry. The slurry was filtered, washed with water (250 mL) and dried to afford the title compound as a solid (206 g, 95%): ¹H NMR (DMSO-d₆) δ: 7.89 (1H, d), 7.59 (1H, d), 7.49 (2H, m), 7.40 (3H, m), 5.35 (2H, s), 3.91 (3H, s).

Step 5: Preparation of
2-amino-4-(benzyloxy)-3-methoxybenzonitrile

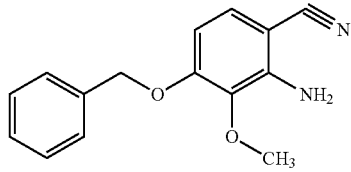 [SMILES: COc1c(OCc2ccccc2)ccc(C#N)c1[N+](=O)[O-]]

A degassed solution of 4-(benzyloxy)-3-methoxy-2-nitrobenzonitrile (Step 4, 185 g, 651 mmol) in glacial acetic acid (3500 mL) and water (10 mL) was cooled to 5° C. and treated with iron powder (182 g, 3.25 mol). After 3 days the reaction mixture was filtered through Celite, and the filtrate concentrated under reduced pressure. The oil, thus obtained, was treated with brine, neutralized with a sodium bicarbonate solution and extracted into DCM. The resulting emulsion was filtered through Celite after which the organic layer was separated, washed with brine, dried (sodium sulfate) and concentrated under reduced pressure to afford the title compound as a solid (145 g, 88%): ¹H NMR (DMSO-d₆) δ: 7.32-7.44 (5H, m), 7.15 (1H, d), 6.47 (1H, d), 5.69 (2H, s), 5.15 (2H, s), 3.68 (3H, s).

Step 6: Preparation of 3-(benzyloxy)-6-(4,5-dihydro-1H-imidazol-2-yl)-2-methoxyaniline

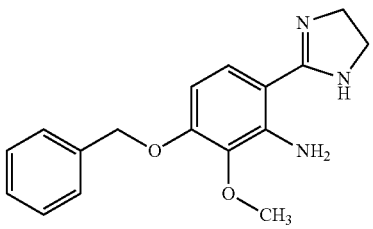 [SMILES: COc1c(OCc2ccccc2)ccc(C2=NCCN2)c1N]

A mixture of 2-amino-4-(benzyloxy)-3-methoxybenzonitrile (Step 5, 144 g, 566 mmol) and sulfur (55 g, 1.7 mol) in ethylenediamine (800 mL) was degassed for 30 minutes then heated to 100° C. After 16 h the reaction mixture was cooled to room temperature and then filtered. The filtrate was concentrated under reduced pressure, diluted with a saturated sodium bicarbonate solution and extracted with EtOAc. The organic layer was washed with brine, dried (sodium sulfate), filtered and concentrated under reduced pressure. The resulting solids were recrystallized from EtOAc and hexanes to afford the title compound (145 g, 86%): ¹H NMR (DMSO-d₆)

δ: 7.27-7.48 (5H, m), 7.14 (1H, d), 6.92 (2H, m), 6.64 (1H, m), 6.32 (1H, d), 5.11 (2H, s), 3.67 (3H, s), 3.33 (2H, s).

Step 7: Preparation of 8-(benzyloxy)-7-methoxy-2,3-dihydroimidazo[1,2-c]quinazolin-5-amine

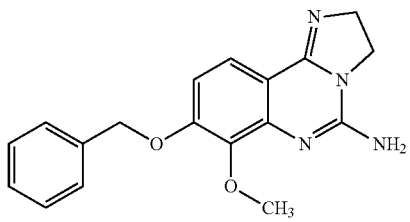 [SMILES: COc1c(OCc2ccccc2)ccc2c1N=C(N)N1CCN=C21]

A mixture of 3-(benzyloxy)-6-(4,5-dihydro-1H-imidazol-2-yl)-2-methoxyaniline (Step 6, 100 g, 336 mmol) and triethylamine (188 mL) in DCM (3 L) was cooled to 0° C. and treated with cyanogen bromide (78.4 g, 740 mmol). The reaction mixture was stirred and allowed to warm to room temperature gradually. After 16 h the reaction mixture was diluted with a solution of saturated sodium bicarbonate and extracted with DCM. The organic layer was washed three times with saturated bicarbonate solution followed by multiple washes with brine. The organic layer was dried (sodium sulfate) and concentrated under reduced pressure to give a semi solid (130 g with triethylamine salt contamination): $^1$H NMR (DMSO-$d_6$) δ: 7.30-7.48 (7H, m), 5.31 (2H, s), 4.32 (2H, m), 4.13 (2H, m), 3.81 (3H, s).

Step 8: Preparation of 5-amino-7-methoxy-2,3-dihydroimidazo[1,2-c]quinazolin-8-ol bis(trifluoroacetate)

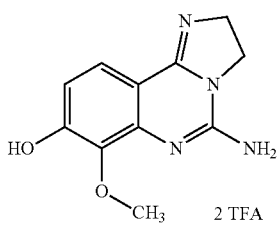

3-(Benzyloxy)-6-(4,5-dihydro-1H-imidazol-2-yl)-2-methoxyaniline (Step 7, 30 g, 93 mmol) was added portionwise over 1 h to a round bottom flask containing TFA (400 mL) precooled with an ice bath. The reaction mixture was heated to 60° C. and allowed to stir at this temperature for 17 h at which time it was cooled to rt and the reaction mixture concentrated under reduced pressure. The resulting residue was taken up in DCM and hexanes and concentrated under reduced pressure. The material thus obtained was dissolved in MeOH and DCM (250 mL, 1:1) and concentrated under reduced pressure. The resulting solid was dried overnight under vacuum with low heat to give the title compound (100%): $^1$H NMR (DMSO-$d_6$) δ: 7.61 (1H, m), 6.87 (1H, m), 4.15 (2H, br t), 4.00 (2H, m), 3.64 (3H, s).

Intermediate B: Preparation of N-(8-hydroxy-7-methoxy-2,3-dihydroimidazo[1,2-c]quinazolin-5-yl) nicotinamide

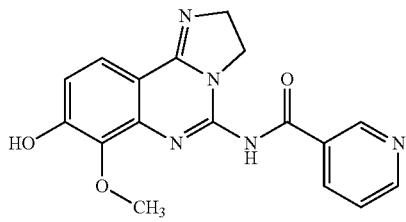

Step 1: Preparation of N-[8-(benzyloxy)-7-methoxy-2,3-dihydroimidazo[1,2-c]quinazolin-5-yl]nicotinamide

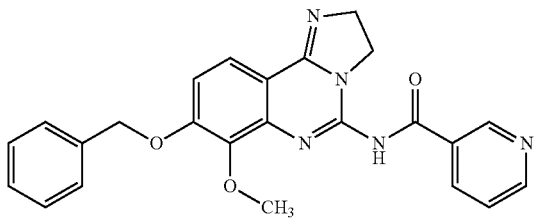 [SMILES: COc1c(OCc2ccccc2)ccc2c1N=C(NC(=O)c1cccnc1)N1CCN=C21]

8-(Benzyloxy)-7-methoxy-2,3-dihydroimidazo[1,2-c]quinazolin-5-amine (Intermediate A, Step 7, 21 g, 65 mmol) and nicotinic acid (12 g, 97.7 mmol) were suspended in DMF (240 mL). Diisopropylethylamine (33.7 g, 260.4 mmol) and then PyBOP (51 g, 97.7 mmol) were added and the resulting mixture stirred with overhead stirring for 3 days at ambient temperature. At this time, the resultant precipitate was isolated by vacuum filtration. After repeated washing with EtOAc, the material was dried under vacuum with slight heating to yield the title compound (27.3 g, 98%): HPLC MS RT=1.09 min, MH$^+$=481.2; $^1$H NMR (DMSO-$d_6$+2 drops TFA-d) δ: 9.32 (1H, s), 8.89 (1H, br m), 8.84 (1H, d), 7.89 (1H, br m), 7.82 (1H, d), 7.37 (1H, d), 7.27 (1H, d), 7.16 (6H, m), 5.18 (2H, s), 4.36 (2H, t), 4.04 (2H, t), 3.78 (3H, s).

Step 2: Preparation of N-(8-hydroxy-7-methoxy-2,3-dihydroimidazo[1,2-c]quinazolin-5-yl)nicotinamide

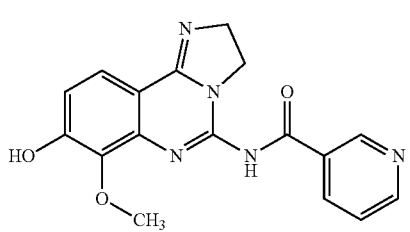 [SMILES: COc1c(O)ccc2c1N=C(NC(=O)c1cccnc1)N1CCN=C21]

N-[8-(Benzyloxy)-7-methoxy-2,3-dihydroimidazo[1,2-c]quinazolin-5-yl]nicotinamide (Step 1, 20 g, 45.1 mmol) was added portionwise over 1 h to a round bottom flask containing TFA (400 mL) precooled with an ice bath. The reaction mixture was heated to 60° C. and allowed to stir at this temperature for 17 h at which time it was cooled to ambient. The reaction mixture was then concentrated under reduced pressure. The resulting residue was taken up in DCM and hexane and concentrated under reduced pressure. The material thus obtained was dissolved in MeOH and DCM (250 mL, 1:1) and concentrated under reduced pressure. The resulting solids were dried overnight under vacuum with low heat to give the title compound (17.3 g, 66%): HPLC MS RT=1.09 min, MH+=481.2; $^1$H NMR (DMSO-d$_6$+2 drops TFA-d) δ: 13.41 (1H, s), 12.21 (1H, br s), 9.38 (1H, s), 8.78 (1H, d), 8.53 (1H, d), 7.85 (1H, d), 7.59 (1H, m), 7.17 (1H, d), 4.54 (2H, m), 4.21 (2H, m), 3.98 (3H, s).

Intermediate C: Preparation of N-(7-hydroxy-2,3-dihydroimidazo[1,2-c]quinazolin-5-yl)nicotinamide

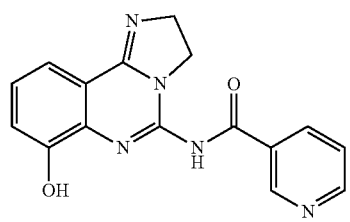 [SMILES: O=C(NC1=Nc2c(O)cccc2C2=NCCN12)c1cccnc1]

Step 1: Preparation of 3-methoxy-2-nitrobenzonitrile

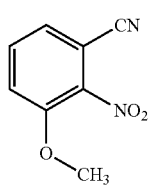

3-Methoxy-2-nitrobenzaldehyde (50.2 g, 277 mmol) was dissolved in THF (300 mL) and 28% aqueous ammonium hydroxide (1000 mL) and iodine (100.7 g, 396 mmol) were slowly added. The mixture was stirred 2 h at rt, then Na$_2$SO$_3$ (21 g, 166 mmol) was added and the mixture stirred vigorously for 20 min. The brown-colored mixture became colorless and a precipitate formed. The solid was collected by vacuum filtration, washed well with water and dried briefly under suction to give the title compound (43 g, 87%): $^1$H NMR (DMSO-d$_6$) δ: 3.94 (3H, s), 7.64 (1H, dd), 7.75-7.78 (2H, m).

Step 2: Preparation of 2-amino-3-methoxybenzonitrile

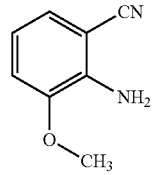

3-Methoxy-2-nitrobenzonitrile (Step 1, 43.3 g, 243 mmol) was suspended in AcOH (1000 mL) and degassed thoroughly. To this was added iron powder (40.7 g, 729 mmol) slowly. After 30 min an exotherm was observed and moderated by the use of an ice bath. After 2 h Celite was added and the entire mixture filtered through a pad of Celite. The Celite was washed well with AcOH, and the combined filtrates concentrated under reduced pressure to approximate volume of 100 mL AcOH. The residue was diluted with EtOAc (1000 mL), solid K$_2$CO$_3$ added and the mixture stirred overnight. The mixture was then filtered through Celite again and washed well with EtOAc. The solvent was removed under reduced pressure until a volume of approximately 500 mL EtOAc. This solution was washed with a saturated NaHCO$_3$ solution (500 mL) and brine (300 mL) then the solvent removed under reduced pressure. The resulting solid was purified via silica gel chromatography (0-30% EtOAc/Hexanes). Fractions containing product were combined, the solvent removed under reduced pressure to give the title compound (26.6 g, 74%): HPLC MS RT=2.19 min, MH+=149.0; $^1$H NMR (DMSO-d$_6$) δ: 3.77 (3H, s), 5.61 (2H, bs), 6.57 (1H, t), 6.96 (1H, dd), 7.00 (1H, dd).

Step 3: Preparation of 2-(4,5-dihydro-1H-imidazol-2-yl)-6-methoxyaniline

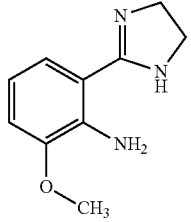

2-Amino-3-methoxybenzonitrile (Step 2, 26.6 g, 179 mmol) was suspended in ethylenediamine (250 mL) and degassed thoroughly. To this was added sulfur powder (8 g, 251 mmol) slowly, then the reaction was heated to 60° C. and stirred 5 h. The reaction was then cooled, concentrated under reduced pressure, then treated with water (300 mL). The resulting suspension was collected by vacuum filtration and washed with water. The solid was purified via silica gel chromatography (50-100% EtOAc/hexanes). Fractions containing product were combined, the solvent removed under reduced pressure to give the title compound (17.3 g, 50%):

HPLC MS RT=1.05 min, MH⁺=192.1; ¹H NMR (DMSO-d₆) δ: 3.81 (3H, s), 3.90 (4H, s), 6.65 (1H, t), 6.86 (1H, dd), 7.03 (1H, dd).

Step 4: Preparation of 7-methoxy-2,3-dihydroimidazo[1,2-c]quinazolin-5-amine

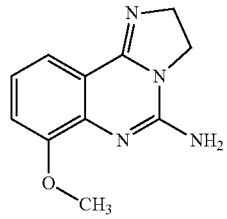

2-(4,5-Dihydro-1H-imidazol-2-yl)-6-methoxyaniline (Step 3, 22.0 g, 115 mmol) and Et₃N (48.1 mL, 345 mmol) were dissolved in CH₂Cl₂ (200 mL), cooled to 10° C. in an ice bath and cyanogen bromide (24.4 g, 230 mmol) was added portionwise. A slight exotherm was noted, and the reaction was stirred overnight. The reaction was concentrated under reduced pressure, then treated with EtOAc (150 mL) and concentrated under reduced pressure again. Finally, the residue was treated with Heptane and concentrated under reduced pressure to give the title compound as a mixture with Et₃N.HBr (62 g, 99%): HPLC MS RT=1.08 min, MH⁺=217.1; ¹H NMR (DMSO-d₆+2 drops TFA-d) δ: 3.85 (3H, s), 4.09-4.16 (2H, m), 4.31-4.38 (2H, m), 7.23 (1H, t), 7.31 (1H, d), 7.57 (1H, dd).

Step 5: Preparation of N-(7-methoxy-2,3-dihydroimidazo[1,2-c]quinazolin-5-yl)nicotinamide

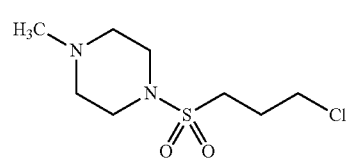

7-Methoxy-2,3-dihydroimidazo[1,2-c]quinazolin-5-amine (Step 4, 31.2 g, 57.7 mmol), nicotinic acid (10.7 g, 86 mmol) and diisopropylethylamine (30.1 mL, 173 mmol) were suspended in DMF (250 mL), and PyBOP (45 g, 86 mmol) was added portionwise. The reaction soon became much thicker with a new solid. After stirring overnight, the solid was collected by filtration then washed with EtOAc (150 mL). The solid was dissolved in CH₂Cl₂ (1000 mL), washed with water (600 mL) and the organic layer dried over Na₂SO₄. The solvent was removed under reduced pressure to give the title compound (12.6 g, 68%): HPLC MS RT=1.18 min, MH⁺=322.1; ¹H NMR (DMSO-d₆+2 drops TFA-d) δ: 4.12 (3H, s), 4.28-4.35 (2H, m), 4.60-4.66 (2H, m), 7.63 (1H, t), 7.72-7.86 (3H, m), 8.76 (1H, d), 8.93 (1H, dd), 9.48 (1H, d).

Step 6: Preparation of N-(7-hydroxy-2,3-dihydroimidazo[1,2-c]quinazolin-5-yl)nicotinamide

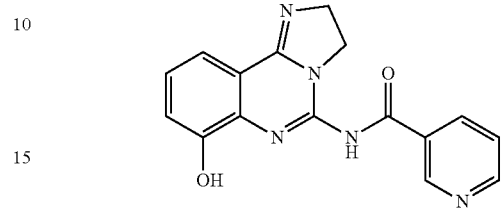

N-(7-Methoxy-2,3-dihydroimidazo[1,2-c]quinazolin-5-yl)nicotinamide (Step 5, 8.7 g, 27 mmol) in NMP (90 mL) was heated to 150° C. and Na₂S (10.6 g, 135 mmol) was added portionwise. The reaction color briefly became blue-green, then changed back to yellow-brown. After stirring at this temperature for 1.5 h, the reaction was cooled to rt whereupon a yellow solid precipitated. The mixture was diluted with EtOAc (200 mL) and the solid collected by vacuum filtration. The solid was suspended in water (200 mL), the pH adjusted to ~7 by the slow addition of aqueous 2N HCl and the mixture was stirred 2 h. The solid was collected via vacuum filtration and washed with water (50 mL) and finally with acetone (50 mL). High vacuum drying overnight gave the title compound (7.8 g, 93%): HPLC MS RT=0.34 min, MH⁺=308.2; ¹H NMR (DMSO-d₆+2 drops TFA-d) δ: 4.25-4.31 (2H, m), 4.57-4.64 (2H, m), 7.45-7.49 (2H, m), 7.69-7.72 (1H, m), 7.92 (1H, dd), 8.78 (1H, dt), 8.97 (1H, dd), 9.49 (1H, d).

Intermediate D: Preparation of 1-[(3-chloropropyl)sulfonyl]-4-methylpiperazine 3-Chloropropanesulfonyl chloride (1.0 g, 5.6 mmol) dissolved in CH₂Cl₂ (20 mL) and cooled to ~0° C. was treated dropwise with a solution of 1-methylpiperazine (566 mg, 5.6 mmol) and Et₃N (572 mg, 5.6 mmol) in CH₂Cl₂ (10 mL). Following complete addition, the mixture was allowed to warm to rt and stir an additional 2 h. The solvent was evaporated under reduced pressure, the residue triturated with EtOAc (30 mL), vacuum filtered and the solid washed well with EtOAc. The filtrate was concentrated under reduced pressure and the oil residue dried under high vacuum to give the title compound (1.27 g, 93%): ¹H NMR (CDCl₃) δ: 2.17-

2.26 (2H, m), 2.49 (3H, s), 2.75-2.77 (4H, m), 3.02-3.07 (2H, m), 3.46-3.49 (4H, m), 3.60 (2H, t).

Intermediate E: Preparation of 4-[(3-chloropropyl)sulfonyl]morpholine

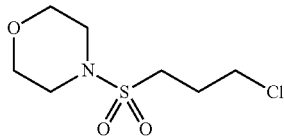 [SMILES: O=S(=O)(CCCCl)N1CCOCC1]

The procedure used for the preparation of Intermediate D was used to prepare the title compound from 3-chloropropanesulfonyl chloride and morpholine. High vacuum drying gave the title compound (1.3 g, 104%): $^1$H NMR (CDCl$_3$) δ: 2.20-2.29 (2H, m), 3.02 (2H, dd), 3.20-3.23 (4H, m), 3.64 (2H, t), 3.68-3.72 (4H, m).

Intermediate F: Preparation of 3-chloro-N,N-dimethylpropane-1-sulfonamide

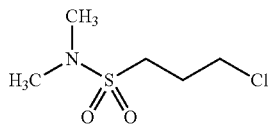

The procedure used for the preparation of Intermediate D was used to prepare the title compound from 3-chloropropanesulfonyl chloride and dimethylamine. High vacuum drying gave the title compound (2.1 g, 100%): $^1$H NMR (DMSO-d$_6$) δ: 2.06-2.11 (2H, m), 2.75 (6H, s), 3.10-3.15 (2H, m), 3.72 (2H, t).

Intermediate G: Preparation of 3-chloro-N,N-diethylpropane-1-sulfonamide

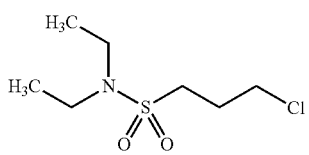

The procedure used for the preparation of Intermediate D was used to prepare the title compound from 3-chloropropanesulfonyl chloride and diethylamine. High vacuum drying gave the title compound (570 mg, 95%) which was used without characterization in the next step.

Intermediate H: Preparation of N-[7-hydroxy-8-(3-morpholin-4-ylpropoxy)-2,3-dihydroimidazo[1,2-c]quinazolin-5-yl]nicotinamide

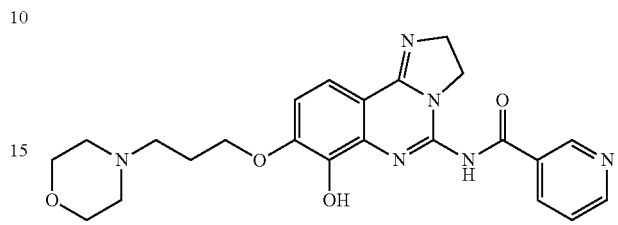

Step 1: Preparation of 4-hydroxy-3-methoxy-2-nitrobenzonitrile

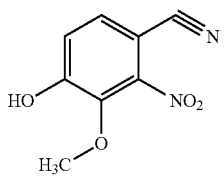

4-Hydroxy-3-methoxy-2-nitrobenzaldehyde (200 g, 1.01 mol) was dissolved in THF (2.5 L) and then ammonium hydroxide (2.5 L) was added followed by iodine (464 g, 1.8 mol). The resulting mixture was allowed to stir for 2 days at which time it was concentrated under reduced pressure. The residue was acidified with HCl (2 N) and extracted into diethyl ether. The organic layer was washed with brine and dried (sodium sulfate) and concentrated under reduced pressure. The residue was washed with diethyl ether and dried under vacuum to provide the title compound (166 g, 84%): $^1$H NMR (DMSO-d$_6$) δ: 11.91 (1H, s), 7.67 (1H, d), 7.20 (1H, d), 3.88 (3H, s)

Step 2: Preparation of 3-methoxy-4-(3-morpholin-4-ylpropoxy)-2-nitrobenzonitrile

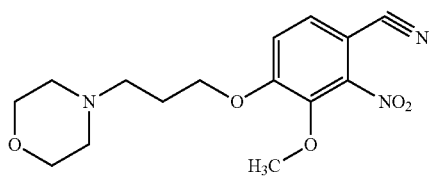 [SMILES: COc1c(OCCCN2CCOCC2)ccc(C#N)c1[N+](=O)[O-]]

To a solution of 4-hydroxy-3-methoxy-2-nitrobenzonitrile (Step 1, 3.9 g, 20.1 mmol) in DMF (150 mL) was added cesium carbonate (19.6 g, 60.3 mmol) and Intermediate C (5.0 g, 24.8 mmol). The reaction mixture was heated at 75° C. overnight then cooled to room temperature and filtered through a pad of silica gel and concentrated under reduced pressure. The material thus obtained was used without further purification

Step 3: Preparation of 2-amino-3-methoxy-4-(3-morpholin-4-ylpropoxy)benzonitrile

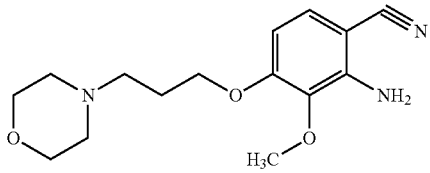

3-Methoxy-4-(3-morpholin-4-ylpropoxy)-2-nitrobenzonitrile (Step 2, 7.7 g, 24.1 mmol) was suspended in acetic acid (170 mL) and cooled to 0° C. Water (0.4 mL) was added, followed by iron powder (6.7 g, 120 mmol) and the resulting mixture was stirred at room temperature for 4 h at which time the reaction mixture was filtered through a pad of Celite and washed with acetic acid (400 mL). The filtrate was concentrated under reduced pressure to 100 mL and diluted with EtOAc (200 mL) at which time potassium carbonate was added slowly. The resulting slurry was filtered through a pad of Celite washing with EtOAc and water. The layers were separated and the organic layer was washed with saturated sodium bicarbonate solution. The organic layer was separated and passed through a pad of silica gel. The resultant solution was concentrated under reduced pressure to provide the title compound (6.5 g, 92%): $^1$H NMR (DMSO-$d_6$) δ: 7.13 (1H, d), 6.38 (1H, d), 5.63 (2H, br s), 4.04 (2H, t), 3.65 (3H, s), 3.55 (4H, m), 2.41 (2H, t), 2.38 (4H, m), 1.88 (2H, m).

Step 4: Preparation of 6-(4,5-dihydro-1H-imidazol-2-yl)-2-methoxy-3-(3-morpholin-4-ylpropoxy)aniline

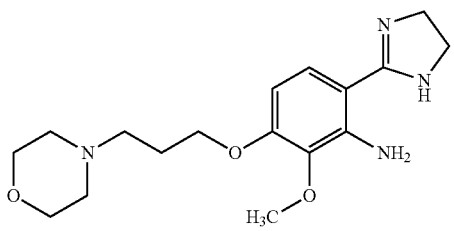 [SMILES: COc1c(OCCCN2CCOCC2)ccc(C2=NCCN2)c1N]

To a degassed mixture of 2-amino-3-methoxy-4-(3-morpholin-4-ylpropoxy)benzonitrile (Step 3, 6.5 g, 22.2 mmol) and ethylene diamine (40 mL) was added sulfur (1.8 g, 55.4 mmol). The mixture was stirred at 100° C. for 3 h at which time water was added to the reaction mixture. The precipitate that was formed was collected and washed with water and then dried overnight under vacuum to provide the title compound (3.2 g, 43%): HPLC MS RT=1.25 min, MW=335.2; $^1$H NMR (DMSO-$d_6$) δ: 7.15 (1H, d), 6.86 (2H, br s), 6.25 (1H, d), 4.02 (2H, t), 3.66 (3H, s), 3.57 (8H, m), 2.46 (2H, t), 2.44 (4H, m), 1.89 (2H, m).

Step 5: Preparation of 7-methoxy-8-(3-morpholin-4-ylpropoxy)-2,3-dihydroimidazo[1,2-c]quinazolin-5-amine

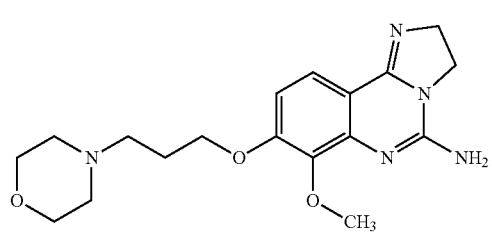 [SMILES: COc1c(OCCCN2CCOCC2)ccc2c1N=C(N)N1CCN=C21]

Cyanogen bromide (10.9 g, 102.9 mmol) was added to a mixture of 6-(4,5-dihydro-1H-imidazol-2-yl)-2-methoxy-3-(3-morpholin-4-ylpropoxy)aniline (Step 4, 17.2 g, 51.4 mmol) and TEA (15.6 g, 154.3 mmol) in DCM (200 mL) precooled to 0° C. After 1 h the reaction mixture was concentrated under reduced pressure and the resulting residue stirred with EtOAc (300 mL) overnight at rt. The resulting slurry was filtered to generate the title compound contaminated with triethylamine hydrobromide (26.2 g, 71%): HPLC MS RT=0.17 min, MH$^+$=360.2.

Step 6: Preparation of N-[7-methoxy-8-(3-morpholin-4-ylpropoxy)-2,3-dihydroimidazo[1,2-c]quinazolin-5-yl]nicotinamide

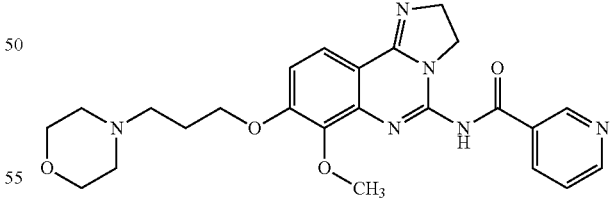

7-Methoxy-8-(3-morpholin-4-ylpropoxy)-2,3-dihydroimidazo[1,2-c]quinazolin-5-amine (Step 5, 1.0 g, 2.2 mmol) was dissolved in DMF (15 mL), and nicotinic acid (0.44 g, 3.3 mmol) was added. PyBOP (1.73 g, 3.3 mmol) and diisopropylethylamine (1.6 mL, 8.9 mmol) were subsequently added, and the mixture was stirred at rt overnight. EtOAc was added, and the solids were isolated by vacuum filtration to give the title compound (0.43 g, 40%): HPLC MS RT=1.15 min, MH$^+$=463.1; $^1$H NMR (DMSO-$d_6$+2 drops TFA-d) δ: 9.01 (2H, s), 8.04 (1H, d), 7.43 (1H, d), 4.54 (2H, m), 4.34 (2H, br t), 4.23 (2H, m), 4.04 (2H, m), 4.00 (3H, s), 3.65 (2H, br t), 3.52 (2H, m), 3.31 (2H, m), 3.18 (2H, m), 2.25 (2H, m).

Step 7: Preparation of N-[7-hydroxy-8-(3-morpholin-4-ylpropoxy)-2,3-dihydroimidazo[1,2-c]quinazolin-5-yl]nicotinamide

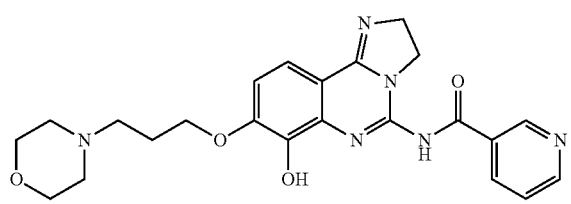 [SMILES: O=C(NC1=Nc2c(ccc(OCCCN3CCOCC3)c2O)C2=NCCN12)c1cccnc1]

N-[7-Methoxy-8-(3-morpholin-4-ylpropoxy)-2,3-dihydroimidazo[1,2-c]quinazolin-5-yl]nicotinamide (Step 6, 1.0 g, 2.15 mmol) in NMP (20 mL) was heated to 100° C. and Na$_2$S (0.84 g, 10.76 mmol) was added portionwise. The reaction was heated to 160° C. for 10 min and cooled to rt and concentrated under reduced pressure. The resulting slurry was diluted with water (100 mL) and the pH adjusted to 7 by the slow addition of aqueous 1N HCl and the mixture was stirred 2 h. The solid was collected via vacuum filtration and washed with water (50 mL) and finally triturated with CH$_2$Cl$_2$/heptane (10 mL). High vacuum drying overnight gave the title compound (0.49 g, 51%): HPLC MS RT=0.21 min, MH$^+$=451; $^1$H NMR (DMSO-d$_6$+2 drops TFA-d) δ: 2.14-2.26 (2H, m), 3.03-3.17 (2H, m), 3.32-3.54 (4H, m), 3.60-3.72 (2H, m), 3.95-4.05 (2H, m), 4.18-4.35 (4H, m), 4.51-4.64 (2H, m), 7.38 (1H, d), 7.68 (1H, dd), 7.82 (1H, d), 8.63 (1H), 8.84 (1H, dd), 9.42 (1H, s), 13.39 (1H, s).

Intermediate I: Preparation of 5-amino-2,3-dihydroimidazo[1,2-c]quinazolin-8-ol

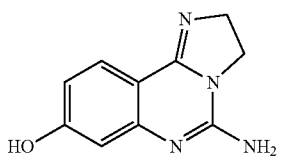

Step 1: Preparation of 2-amino-4-methoxybenzonitrile

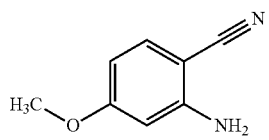

The procedure used for the preparation of Intermediate C, Step 2 was used to prepare the title compound from 4-methoxy-2-nitrobenzonitrile. High vacuum drying gave the title compound (37 g, 88%). TLC (CH$_2$Cl$_2$): R$_f$=0.32; HPLC MS RT=2.10 min, MH$^+$=149.

Step 2: Preparation of 2-(4,5-dihydro-1H-imidazol-2-yl)-5-methoxyaniline

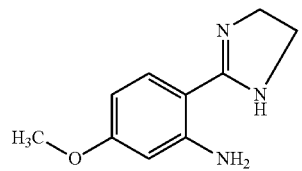

The procedure used for the preparation of Intermediate C, Step 3 was used to prepare the title compound from 2-amino-4-methoxybenzonitrile (Step 1) and ethylene diamine. High vacuum drying gave the title compound (44 g, 92%). HPLC MS RT=1.04 min, MH$^+$=192.

Step 3: Preparation of 8-methoxy-2,3-dihydroimidazo[1,2-c]quinazolin-5-amine hydrobromide

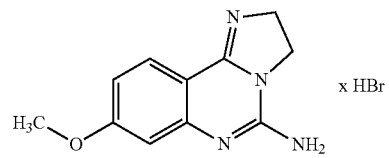 [SMILES: COc1ccc2c(c1)N=C(N)N1CCN=C21]

The procedure used for the preparation of Intermediate C, Step 4 was used to prepare the title compound from 2-(4,5-dihydro-1H-imidazol-2-yl)-5-methoxyaniline (Step 2) and cyanogen bromide as a yellow solid (7.1 g, 56%). HPLC MS RT=1.07 min, [M-HBr+H]$^+$=217.2

Step 4: Preparation of 5-amino-2,3-dihydroimidazo[1,2-c]quinazolin-8-ol

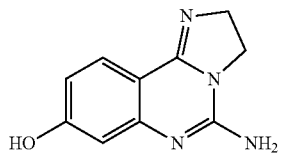 [SMILES: NC1=Nc2cc(O)ccc2C2=NCCN12]

8-Methoxy-2,3-dihydroimidazo[1,2-c]quinazolin-5-amine (Step 3, 1.00 g, 0.002 mol) was dissolved in 1-methyl-2-pyrrolidinone (20 ml) and treated with sodium sulfide (0.76 g, 0.010 mol) and heated to 160° C. for 5 h. It was cooled, filtered from reaction rinsing with EtOAc. The solid was dissolved in a minimal amount of water and brought to pH=1 with 2N HCl, then back to pH=7 with 1N NaOH and filtered.

The title compounds was isolated as a white solid (396 mg, 99%). HPLC MS RT=0.41 min, MH+=203.0

EXAMPLES

Example 1

Preparation of N-(7-methoxy-8-{3-[(4-methylpiperazin-1-yl)sulfonyl]propoxy}-2,3-dihydroimidazo[1,2-c]quinazolin-5-yl)nicotinamide

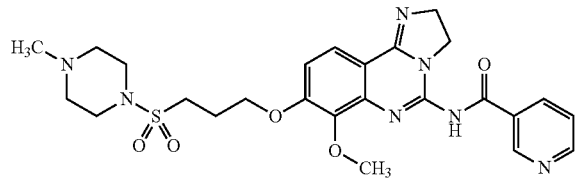 [SMILES: COc1c(OCCCS(=O)(=O)N2CCN(C)CC2)ccc2c1N=C(NC(=O)c1cccnc1)N1CCN=C21]

5-Amino-7-methoxy-2,3-dihydroimidazo[1,2-c]quinazolin-8-ol bistrifluoroacetate salt (Intermediate B, 2.0 g, 3.5 mmol) and 1-[(3-chloropropyl)sulfonyl]-4-methylpiperazine (Intermediate D, 3.4 g, 14 mmol) was suspended in DMF (35 mL) and $Cs_2CO_3$ (4.6 g, 14 mmol) was added in one portion. The mixture was warmed to 60° C. and stirred overnight. The DMF was evaporated under reduced pressure and the residue triturated with a mixture of ~10% MeOH in $CH_2Cl_2$ (40 mL). The mixture was vacuum filtered and the solids were washed well with $CH_2Cl_2$. The filtrate was concentrated under reduced pressure, and the residue purified via silica gel chromatography (0-6% MeOH/$CH_2Cl_2$). The fractions were combined, and the solvent was evaporated under reduced pressure. Drying under high vacuum at 50° C. gave the title compound (1.46 g, 76%): HPLC MS RT=1.31 min, MH+=542.2; $^1$H NMR (DMSO-$d_6$+2 drops TFA-d) δ: 2.21-2.26 (2H, m), 2.84 (3H, s), 3.09-3.17 (4H, m), 3.34-3.39 (2H, m), 3.49-3.42 (2H, m), 3.77-3.80 (2H, m), 4.01 (3H, s), 4.22-4.28 (2H, m), 4.37 (2H, t), 4.54-4.60 (2H, m), 7.49 (1H, d), 7.87 (1H, dd), 8.06 (1H, d), 8.83 (1H, d), 8.95 (1H, dd), 9.48 (1H, d).

Example 2

Preparation of N-(7-methoxy-8-{[4-(methylsulfonyl)benzyl]oxy}-2,3-dihydroimidazo[1,2-c]quinazolin-5-yl)nicotinamide

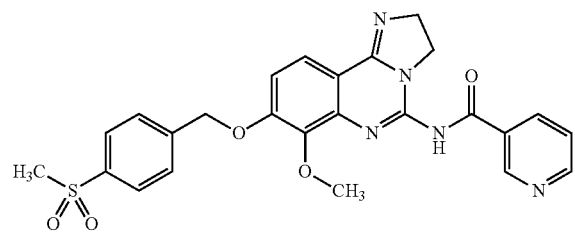 [SMILES: COc1c(OCc2ccc(S(C)(=O)=O)cc2)ccc2c1N=C(NC(=O)c1cccnc1)N1CCN=C21]

The procedure used for the preparation of Example 1 was used to prepare the title compound from 5-amino-7-methoxy-2,3-dihydroimidazo[1,2-c]quinazolin-8-ol bistrifluoroacetate salt (Intermediate B) and 1-(chloromethyl)-4-(methylsulfonyl)benzene. High vacuum drying at 60° C. gave the title compound (111 mg, 83%): HPLC MS RT=2.05 min, MH+=506.1; $^1$H NMR (DMSO-$d_6$+2 drops TFA-d) δ: 3.18 (3H, s), 3.99 (3H, s), 3.22-3.25 (2H, m), 4.50-4.54 (2H, m), 5.51 (2H, s), 7.55 (1H, d), 7.74 (2H, d), 7.89-8.04 (4H, m), 8.90 (1H, d), 8.95 (1H, d), 9.47 (1H, d).

Example 3

Preparation of N-{7-methoxy-8-[3-(morpholin-4-ylsulfonyl)propoxy]-2,3-dihydroimidazo[1,2-c]quinazolin-5-yl}nicotinamide

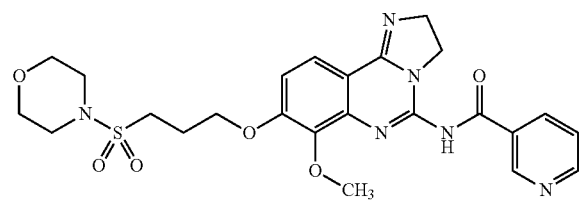 [SMILES: COc1c(OCCCS(=O)(=O)N2CCOCC2)ccc2c1N=C(NC(=O)c1cccnc1)N1CCN=C21]

The procedure used for the preparation of Example 1 was used to prepare the title compound from 5-amino-7-methoxy-2,3-dihydroimidazo[1,2-c]quinazolin-8-ol bistrifluoroacetate salt (Intermediate B) and 4-[(3-chloropropyl)sulfonyl]morpholine (Intermediate E). High vacuum drying at 60° C. gave the title compound (200 mg, 85%): HPLC MS RT=1.80 min, MH+=529.2; $^1$H NMR (DMSO-$d_6$+2 drops TFA-d) δ: 2.22-2.27 (2H, m), 3.15-3.19 (4H, m), 3.25-3.30 (2H, m), 3.62-3.65 (4H, m), 4.02 (3H, s), 4.23-4.30 (2H, m), 4.39 (2H, t), 4.55-4.62 (2H, m), 7.51 (1H, d), 7.95 (1H, dd), 8.07 (1H, d), 8.96 (1H, d), 9.01 (1H, dd), 9.53 (1H, d).

Example 4

Preparation of N-{8-[3-(1,1-dioxidothiomorpholin-4-yl)propoxy]-7-methoxy-2,3-dihydroimidazo[1,2-c]quinazolin-5-yl}nicotinamide

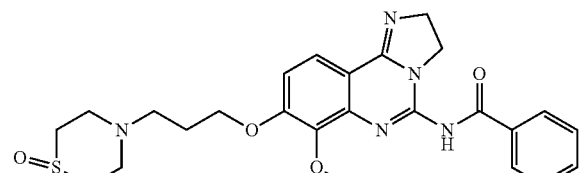

3-(1,1-Dioxidothiomorpholin-4-yl)propan-1-ol (1.07 g, 5.6 mmol) and $Et_3N$ (564 mg, 5.6 mmol) in DMF (15 mL) at rt were treated dropwise with methanesulfonyl chloride (608 mg, 5.3 mmol). A solid precipitated, and the reaction was stirred 2 h. This solution was then added in one portion to a suspension of 5-amino-7-methoxy-2,3-dihydroimidazo[1,2-c]quinazolin-8-ol bistrifluoroacetate salt (Intermediate B, 1.5 g, 2.6 mmol) and $Cs_2CO_3$ (3.4 g, 10.6 mmol) in DMF (25 mL) at rt. The reaction was warmed to 60° C. and stirred overnight. The reaction was cooled and the DMF evaporated under reduced pressure. The residue triturated with a mixture of ~10% MeOH in $CH_2Cl_2$ (50 mL). The mixture was vacuum filtered and the solids were washed well with the same MeOH/$CH_2Cl_2$ mixture (50 mL). The filtrate was concentrated under reduced pressure, and the residue purified via silica gel chromatography (0-4% MeOH/$CH_2Cl_2$). The fractions were combined and the solvent evaporated under reduced pressure. The isolated material was hot triturated in EtOH (50 mL), cooled and collected by filtration. The solid was washed with EtOH (2×25 mL). High vacuum drying at 60° C. gave the title compound (1.17 g, 86%): HPLC MS RT=1.67 min, MH$^+$=513.1; $^1$H NMR (DMSO-d$_6$+2 drops TFA-d) δ: 2.25-2.30 (2H, m), 3.44-3.49 (2H, m), 3.61-3.63 (4H, m), 3.83 (4H, bs), 4.02 (3H, s), 4.23-4.27 (2H, m), 4.34 (2H, t), 4.55-4.62 (2H, m), 7.48 (1H, d), 7.99 (1H, dd), 8.07 (1H, d), 8.99 (1H, d), 9.01 (1H, dd), 9.53 (1H, d).

Example 5

Preparation of N-(8-{3-[(dimethylamino)sulfonyl]propoxy}-7-methoxy-2,3-dihydroimidazo[1,2-c]quinazolin-5-yl)nicotinamide

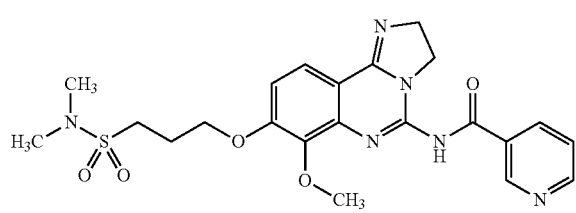 [SMILES: COc1c(OCCCS(=O)(=O)N(C)C)ccc2c1N=C(NC(=O)c1cccnc1)N1CCN=C21]

The procedure used for the preparation of Example 1 was used to prepare the title compound from 5-amino-7-methoxy-2,3-dihydroimidazo[1,2-c]quinazolin-8-ol bistrifluoroacetate salt (Intermediate B) and 3-chloro-N,N-dimethylpropane-1-sulfonamide (Intermediate F). High vacuum drying at 60° C. gave the title compound (1.12 g, 86%): HPLC MS RT=2.10 min, NH$^+$=515.2; $^1$H NMR (DMSO-d$_6$+2 drops TFA-d) δ: 2.20-2.25 (2H, m), 2.78 (6H, s), 3.20-3.25 (2H, m), 4.02 (3H, s), 4.23-4.29 (2H, m), 4.38 (2H, t), 4.55-4.61 (2H, m), 7.50 (1H, d), 8.02 (1H, dd), 8.06 (1H, d), 9.01-9.04 (2H, m), 9.54 (1H, d).

Example 6

Preparation of N-(8-{3-[(diethylamino)sulfonyl]propoxy}-7-methoxy-2,3-dihydroimidazo[1,2-c]quinazolin-5-yl)nicotinamide

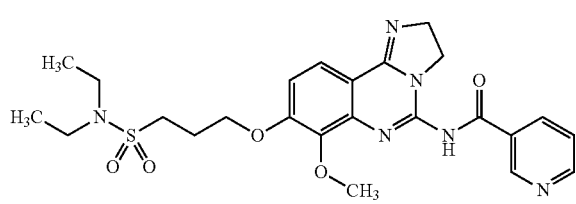 [SMILES: CCN(CC)S(=O)(=O)CCCOc1ccc2c(c1OC)N=C(NC(=O)c1cccnc1)N1CCN=C21]

The procedure used for the preparation of Example 1 was used to prepare the title compound from 5-amino-7-methoxy-2,3-dihydroimidazo[1,2-c]quinazolin-8-ol bistrifluoroacetate salt (Intermediate B) and 3-chloro-N,N-diethylpropane-1-sulfonamide (Intermediate G). High vacuum drying at 60° C. gave the title compound (50 mg, 36%): HPLC MS RT=2.10 min, MH$^+$=515.2; $^1$H NMR (DMSO-d$_6$+2 drops TFA-d) δ: 1.10-1.12 (6H, t), 2.17-2.21 (2H, m), 3.17-3.25 (6H, m), 4.00 (3H, s), 4.22-4.29 (2H, m), 4.37 (2H, t), 4.54-4.60 (2H, m), 7.49 (1H, d), 7.95 (1H, dd), 8.05 (1H, d), 8.92 (1H, d), 8.98 (1H, dd), 9.51 (1H, d).

Example 7

Preparation of N-{7-[3-(morpholin-4-ylsulfonyl)propoxy]-2,3-dihydroimidazo[1,2-c]quinazolin-5-yl}nicotinamide

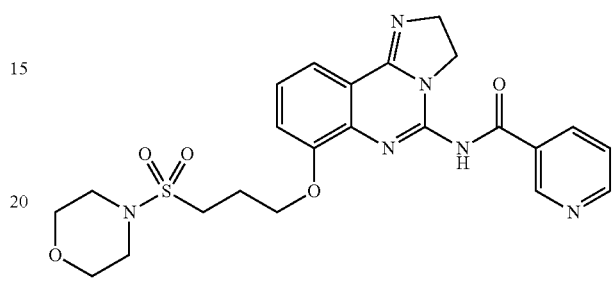

The procedure used for the preparation of Example 1 was used to prepare the title compound from N-(7-hydroxy-2,3-dihydroimidazo[1,2-c]quinazolin-5-yl)nicotinamide (Intermediate C) and 4-[(3-chloropropyl)sulfonyl]morpholine (Intermediate E). High vacuum drying at 60° C. gave the title compound (42 mg, 34%): HPLC MS RT=1.82 min, MH$^+$=499.2; $^1$H NMR (DMSO-d$_6$+2 drops TFA-d) δ: 2.26-2.31 (2H, m), 3.13-3.24 (4H, m), 3.37-3.43 (2H, m), 3.60-3.63 (4H, m), 4.27-4.34 (2H, m), 4.43 (2H, t), 4.58-4.65 (2H, m), 7.58 (1H, t), 7.73 (1H, d), 7.84 (1H, d), 7.94 (1H, dd), 8.86 (1H, d), 8.98 (1H, dd), 9.46 (1H, d).

Example 8

Preparation of N-(7-{3-[(4-methylpiperazin-1-yl)sulfonyl]propoxy}-2,3-dihydroimidazo[1,2-c]quinazolin-5-yl)nicotinamide

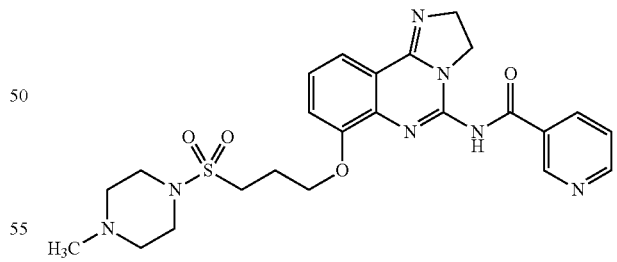

The procedure used for the preparation of Example 1 was used to prepare the title compound from N-(7-hydroxy-2,3-dihydroimidazo[1,2-c]quinazolin-5-yl)nicotinamide (Intermediate C) and 1-[(3-chloropropyl)sulfonyl]-4-methylpiperazine (Intermediate D). High vacuum drying at 60° C. gave the title compound (72 mg, 57%): HPLC MS RT=1.22 min, MH$^+$=512.2; $^1$H NMR (DMSO-d$_6$+2 drops TFA-d) δ: 2.26-2.31 (2H, m), 2.82 (3H, s), 3.11-3.21 (4H, m), 3.45-3.50 (4H, m), 3.83-3.87 (2H, m), 4.27-4.34 (2H, m), 4.42 (2H, t), 4.58-

4.65 (2H, m), 7.60 (1H, t), 7.73 (1H, d), 7.85 (1H, d), 7.94 (1H, dd), 8.86 (1H, d), 9.00 (1H, dd), 9.48 (1H, d).

Example 9

Preparation of N-{7-[3-(1,1-dioxidothiomorpholin-4-yl)propoxy]-2,3 dihydroimidazo[1,2-c]quinazolin-5-yl}nicotinamide

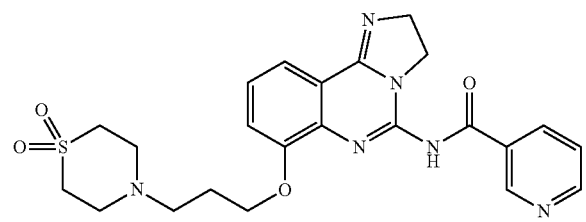 [SMILES: O=C(NC1=Nc2c(OCCCN3CCS(=O)(=O)CC3)cccc2C2=NCCN12)c1cccnc1]

The procedure used for the preparation of Example 4 was used to prepare the title compound from N-(7-hydroxy-2,3-dihydroimidazo[1,2-c]quinazolin-5-yl)nicotinamide (Intermediate C) and 3-(1,1-dioxidothiomorpholin-4-yl)propan-1-ol. High vacuum drying at 60° C. gave the title compound (105 mg, 45%): HPLC MS RT=1.16 min, MH+=483.2; $^1$H NMR (DMSO-d$_6$+2 drops TFA-d) δ: 2.32-2.33 (2H, m), 3.53-3.58 (2H, m), 3.66 (4H, bs), 3.87 (4H, bs), 4.27-4.40 (2H, m), 4.58-4.65 (2H, m), 7.60 (1H, t), 7.70 (1H, d), 7.93 (1H, dd), 8.89 (1H, d), 8.99 (1H, dd), 9.50 (1H, s).

Example 10

Preparation of N-(7-{[4-(methylsulfonyl)benzyl]oxy}-2,3-dihydroimidazo[1,2-c]quinazolin-5-yl)nicotinamide

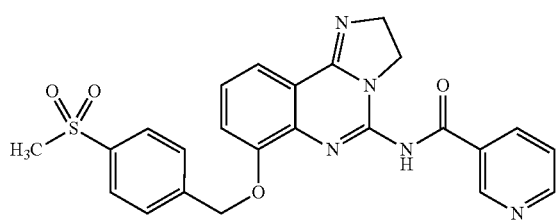 [SMILES: CS(=O)(=O)c1ccc(COc2cccc3c2N=C(NC(=O)c2cccnc2)N2CCN=C32)cc1]

The procedure used for the preparation of Example 1 was used to prepare the title compound from N-(7-hydroxy-2,3-dihydroimidazo[1,2-c]quinazolin-5-yl)nicotinamide (Intermediate C) and 1-(chloromethyl)-4-(methylsulfonyl)benzene. High vacuum drying at 60° C. gave the title compound (50 mg, 43%): HPLC MS RT=2.05 min, MH+=476.1; $^1$H NMR (DMSO-d$_6$+2 drops TFA-d) δ: 3.24 (3H, s), 4.28-4.34 (2H, m), 4.59-4.66 (2H, m), 5.62 (2H, s), 7.61 (1H, t), 7.79-7.88 (4H, m), 7.98-8.05 (3H, m), 8.98-9.02 (2H, m), 9.53 (1H, s).

Example 11

Preparation of N-(7-{3-[(dimethylamino)sulfonyl]propoxy}-2,3-dihydroimidazo[1,2-c]quinazolin-5-yl)nicotinamide

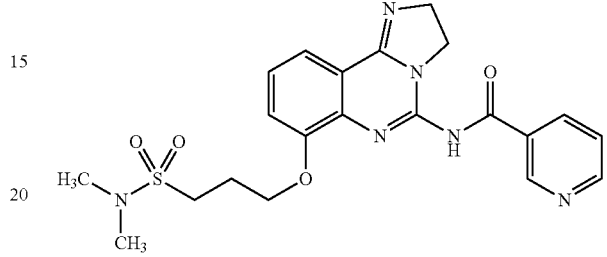

The procedure used for the preparation of Example 1 was used to prepare the title compound from N-(7-hydroxy-2,3-dihydroimidazo[1,2-c]quinazolin-5-yl)nicotinamide (Intermediate C) and 3-chloro-N,N-dimethylpropane-1-sulfonamide (Intermediate F). High vacuum drying at 60° C. gave the title compound (44 mg, 39%): HPLC MS RT=0.68 min, MH+=457.3; $^1$H NMR (DMSO-d$_6$+2 drops TFA-d) δ: 2.27 (2H, bs), 2.84 (6H, s), 3.36-3.37 (2H, m), 4.31 (2H, bs), 4.43 (2H, bs), 4.62 (2H, bs), 7.59-7.61 (1H, m), 7.71 (1H, bs), 7.83-7.86 (1H, m), 7.97-7.98 (1H, m), 8.89 (1H, bs), 9.00 (1H, m), 9.47 (1H, bs).

Example 12

Preparation of N-{8-(3-morpholin-4-ylpropoxy)-7-[3-(morpholin-4-yl)sulfonyl)propoxy]-2,3-dihydroimidazo[1,2-c]quinazolin-5-yl}nicotinamide

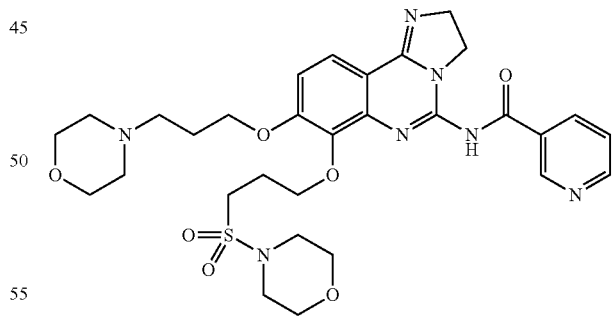

The procedure used for the preparation of Example 1 was used to prepare the title compound from N-[7-hydroxy-8-(3-morpholin-4-ylpropoxy)-2,3-dihydroimidazo[1,2-c]quinazolin-5-yl]nicotinamide (Intermediate H) and 4-[(3-chloropropyl)sulfonyl]morpholine (Intermediate E). High vacuum drying gave the title compound (24 mg, 26%): HPLC MS RT=0.24 min, MH+=642.5; $^1$H NMR (DMSO-d$_6$+2 drops TFA-d) δ: 2.22-2.27 (4H, m), 3.13-3.14 (2H, m), 3.17-3.19 (4H, m), 3.28-3.32 (2H, m), 3.36-3.40 (2H, m), 3.49-3.52 (2H, m), 3.59-3.61 (4H, m), 3.64-3.69 (2H, m), 3.99-

4.02 (2H, m), 4.24-4.29 (2H, m), 4.32-4.36 (4H, m), 4.56-4.61 (2H, m), 7.49 (1H, d), 7.99 (1H, dd), 8.09 (1H, d), 8.96 (1H, d), 9.03 (1H, dd), 9.51 (1H, d).

Example 13

Preparation of N-[7-{3-[(4-methylpiperazin-1-yl)sulfonyl]propoxy}-8-(3-morpholin-4-ylpropoxy)-2,3-dihydroimidazo[1,2-c]quinazolin-5-yl]nicotinamide

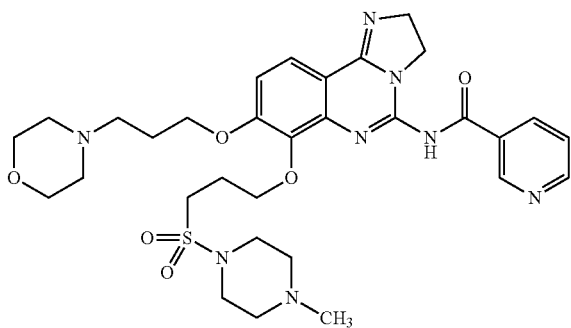 [SMILES: CN1CCN(S(=O)(=O)CCCOc2c(OCCCN3CCOCC3)ccc3c2N=C(NC(=O)c2cccnc2)N2CCN=C32)CC1]

The procedure used for the preparation of Example 1 was used to prepare the title compound from N-[7-hydroxy-8-(3-morpholin-4-ylpropoxy)-2,3-dihydroimidazo[1,2-c]quinazolin-5-yl]nicotinamide (Intermediate H) and 1-[(3-chloropropyl)sulfonyl]-4-methylpiperazine (Intermediate D). High vacuum drying gave the title compound (29 mg, 27%): HPLC MS RT=0.23 min, MH$^+$=655.6; $^1$H NMR (DMSO-d$_6$+2 drops TFA-d) δ: 2.22-2.27 (4H, m), 2.82 (3H, s), 3.09-3.18 (6H, m), 3.29-3.32 (2H, m), 3.45-3.52 (6H, m), 3.64-3.70 (2H, m), 3.77-3.80 (2H, m), 3.99-4.01 (2H, m), 4.24-4.29 (2H, m), 4.32-4.36 (4H, m), 4.55-4.60 (2H, m), 7.49 (1H, d), 7.90 (1H, dd), 8.09 (1H, d), 8.83 (1H, d), 8.98 (1H, dd), 9.47 (1H, d).

Example 14

Preparation of N-[7-{3-[(Diethylamino)sulfonyl]propoxy}-8-(3-morpholin-4-ylpropoxy)-2,3-dihydroimidazo[1,2-c]quinazolin-5-yl]nicotinamide

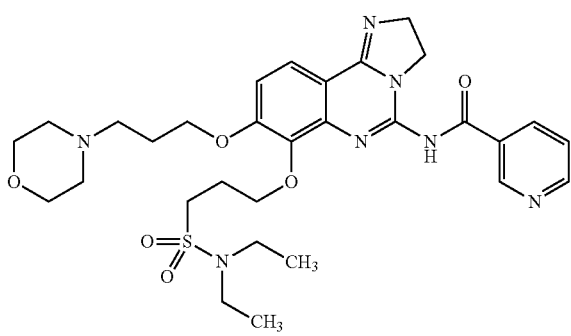 [SMILES: CCN(CC)S(=O)(=O)CCCOc1c(OCCCN2CCOCC2)ccc2c1N=C(NC(=O)c1cccnc1)N1CCN=C21]

The procedure used for the preparation of Example 1 was used to prepare the title compound from N-[7-hydroxy-8-(3-morpholin-4-ylpropoxy)-2,3-dihydroimidazo[1,2-c]quinazolin-5-yl]nicotinamide (Intermediate H) and -chloro-N,N-diethylpropane-1-sulfonamide (Intermediate G). High vacuum drying gave the title compound (36 mg, 34%): HPLC MS RT=0.23 min, MH$^+$=628.5; $^1$H NMR (DMSO-d$_6$+2 drops TFA-d) δ: 1.07 (6H, t), 2.18-2.27 (4H, m), 3.13-3.18 (2H, m), 3.20-3.24 (4H, q), 3.28-3.33 (4H, m), 3.49-3.52 (2H, m), 3.64-3.70 (2H, m), 3.98-4.02 (2H, m), 4.24-4.29 (2H, m), 4.32-4.36 (4H, m), 4.56-4.61 (2H, m), 7.49 (1H, d), 7.98 (1H, dd), 8.08 (1H, d), 8.91 (1H, d), 9.02 (1H, dd), 9.49 (1H, d).

Example 15

Synthesis of N-[7-{3-[(dimethylamino)sulfonyl]propoxy}-8-(3-morpholin-4-ylpropoxy)-2,3-dihydroimidazo[1,2-c]quinazolin-5-yl]nicotinamide

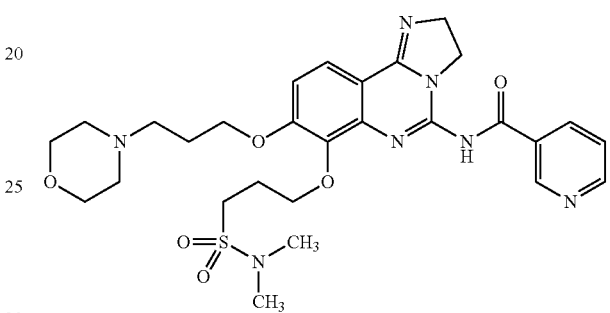

The procedure used for the preparation of Example 1 was used to prepare the title compound from N-[7-hydroxy-8-(3-morpholin-4-ylpropoxy)-2,3-dihydroimidazo[1,2-c]quinazolin-5-yl]nicotinamide (Intermediate H) and 3-chloro-N,N-dimethylpropane-1-sulfonamide (Intermediate F). High vacuum drying gave the title compound (15 mg, 15%): HPLC MS RT=0.24 min, MH$^+$=600.4; $^1$H NMR (DMSO-d$_6$+2 drops TFA-d) δ: 1.07 (6H, t), 2.18-2.27 (4H, m), 3.04-3.13 (2H, m), 3.27-3.36 (4H, q), 3.51 (2H, d), 3.66 (2H, t), 3.98-4.02 (2H, m), 4.21-4.36 (6H, m), 4.56-4.59 (2H, m), 7.49 (1H, d), 8.02 (1H, dd), 8.08 (1H, d), 8.96 (1H, d), 9.04 (1H, dd), 9.50 (1H, d).

Example 16

Preparation of 2-amino-N-(7-methoxy-8-{[4-(methylsulfonyl)benzyl]oxy}-2,3-dihydroimidazo[1,2-c]quinazolin-5-yl)pyrimidine-5-carboxamide

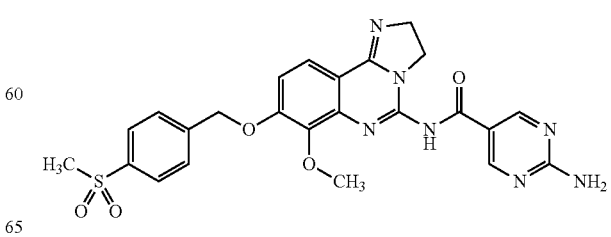

Step 1: Synthesis of 7-methoxy-8-{[4-(methylsulfonyl)benzyl]oxy}-2,3-dihydroimidazo[1,2-c]quinazolin-5-amine

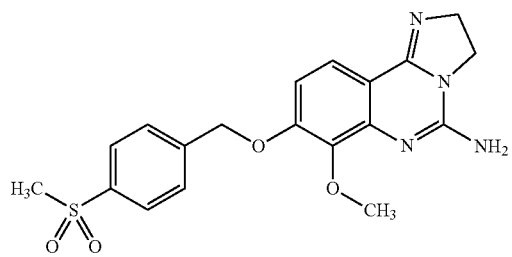 [SMILES: COc1c(OCc2ccc(S(C)(=O)=O)cc2)ccc2c1N=C(N)N1CCN=C21]

The procedure used for the preparation of Example 1 was used to prepare the title compound from 5-amino-7-methoxy-2,3-dihydroimidazo[1,2-c]quinazolin-8-ol bistrifluoroacetate salt (Intermediate A) and 1-(chloromethyl)-4-(methylsulfonyl)benzene. High vacuum drying gave the title compound (970 mg, 56%): HPLC MS RT=1.59 min, MH$^+$=401.1; $^1$H NMR (DMSO-d$_6$+2 drops TFA-d) δ: 3.21 (3H, s), 3.85 (3H, s), 4.16-4.19 (2H, m), 4.32-4.35 (2H, m), 5.47 (2H, s), 7.36 (1H, d), 7.74 (2H, d), 7.88 (1H, d), 7.97 (2H, d).

Step 2: Preparation of 2-amino-N-(7-methoxy-8-{[4-(methylsulfonyl)benzyl]oxy}-2,3-dihydroimidazo[1,2-c]quinazolin-5-yl)pyrimidine-5-carboxamide

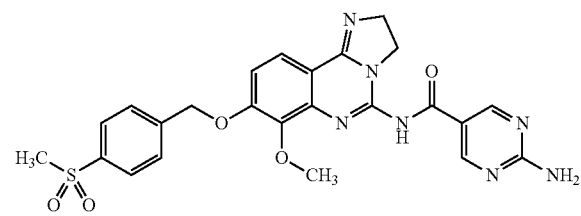 [SMILES: COc1c(OCc2ccc(S(C)(=O)=O)cc2)ccc2c1N=C(NC(=O)c1cnc(N)nc1)N1CCN=C21]

7-Methoxy-8-{[4-(methylsulfonyl)benzyl]oxy}-2,3-dihydroimidazo[1,2-c]quinazolin-5-amine (Step 1, 76 mg, 0.19 mmol) was dissolved in DMF (5 mL), and 2-aminopyrimidine-5-carboxylic acid (40 mg, 0.29 mmol) was added. PyBOP (152 mg, 0.29 mmol) and diisopropylethylamine (0.15 mL, 0.85 mmol) were subsequently added. The mixture was stirred at it overnight, during which a tan solid precipitated. The DMF was removed under reduced pressure and the residue purified via silica gel chromatography (0-3% MeOH/CH$_2$Cl$_2$+0.1% Et$_3$N). The solvent was evaporated under reduced pressure, the residue triturated in water (5 mL), collected by vacuum filtration, then washed with acetone. High vacuum drying gave the title compound (12 mg, 12%): HPLC MS RT=2.06 min, MH$^+$=522.1; $^1$H NMR (DMSO-d$_6$+2 drops TFA-d) δ: 3.22 (3H, s), 4.00 (3H, s), 4.19-4.25 (2H, m), 4.48-4.55 (2H, m), 5.53 (2H, s), 7.53 (1H, d), 7.77 (2H, d), 7.97-8.03 (3H, m), 9.06 (2H, s).

Example 17

Preparation of 2-amino-N-(8-{3-[(dimethylamino)sulfonyl]propoxy}-7-methoxy-2,3-dihydroimidazo[1,2-c]quinazolin-5-yl)pyrimidine-5-carboxamide

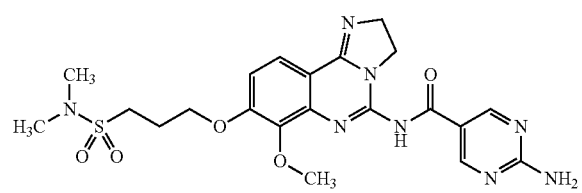

Step 1: Preparation of 3-[(5-amino-7-methoxy-2,3-dihydroimidazo[1,2-c]quinazolin-8-yl)oxy]-N,N-dimethylpropane-1-sulfonamide

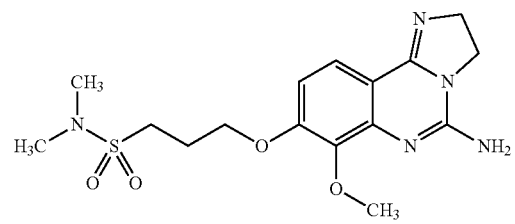 [SMILES: COc1c(OCCCS(=O)(=O)N(C)C)ccc2c1N=C(N)N1CCN=C21]

The procedure used for the preparation of Example 1 was used to prepare the title compound from 5-amino-7-methoxy-2,3-dihydroimidazo[1,2-c]quinazolin-8-ol bistrifluoroacetate salt (Intermediate A) and 3-chloro-N,N-dimethylpropane-1-sulfonamide (Intermediate F). High vacuum drying gave the title compound (1.12 g, 86%): HPLC MS RT=1.28 min, MH$^+$=382.2; $^1$H NMR (DMSO-d$_6$+2 drops TFA-d) δ: 2.15-2.20 (2H, m), 2.77 (6H, s), 3.18-3.23 (2H, m), 3.84 (3H, s), 4.18-4.21 (2H, m), 4.29-4.35 (4H, m), 7.30 (1H, d), 7.90 (1H, d).

Step 2: Preparation of 2-amino-N-(8-{3-[(dimethylamino)sulfonyl]propoxy}-7-methoxy-2,3-dihydroimidazo[1,2-c]quinazolin-5-yl)pyrimidine-5-carboxamide

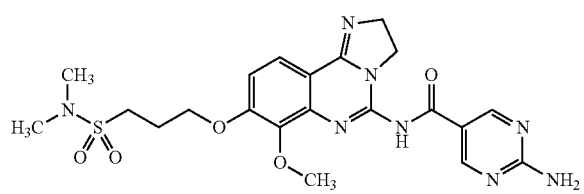 [SMILES: COc1c(OCCCS(=O)(=O)N(C)C)ccc2c1N=C(NC(=O)c1cnc(N)nc1)N1CCN=C21]

The procedure used for the preparation of Example 16, Step 2 was used to prepare the title compound from 3-[(5-amino-7-methoxy-2,3-dihydroimidazo[1,2-c]quinazolin-8-yl)oxy]-N,N-dimethylpropane-1-sulfonamide (Step 1) and 2-aminopyrimidine-5-carboxylic acid. High vacuum drying gave the title compound (261 mg, 79%): HPLC MS RT=2.09 min, MH$^+$=503.2; $^1$H NMR (DMSO-d$_6$+2 drops TFA-d) δ: 2.20-2.25 (2H, m), 2.78 (6H, s), 3.20-3.25 (2H, m), 3.99 (3H, s), 4.18-4.25 (2H, m), 4.37 (2H, t), 4.48-4.55 (2H, m), 7.44 (1H, d), 8.02 (1H, d), 9.07 (2H, s).

Example 18

Preparation of 6-amino-N-(8-{3-[(dimethylamino)sulfonyl]propoxy}-7-methoxy-2,3-dihydroimidazo[1,2-c]quinazolin-5-yl)nicotinamide

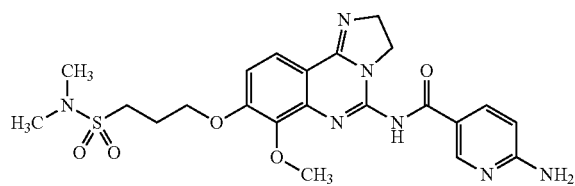 [SMILES: COc1c(OCCCS(=O)(=O)N(C)C)ccc2c1N=C(NC(=O)c1ccc(N)nc1)N1CCN=C21]

The procedure used for the preparation of Example 16, Step 2 was used to prepare the title compound from 3-[(5-amino-7-methoxy-2,3-dihydroimidazo[1,2-c]quinazolin-8-yl)oxy]-N,N-dimethylpropane-1-sulfonamide (Example 17 Step 1) and 6-aminonicotinic acid. High vacuum drying gave the title compound (117 mg, 59%): HPLC MS RT=1.60 min, MH$^+$=502.2; $^1$H NMR (DMSO-d$_6$+2 drops TFA-d) δ: 2.19-2.24 (2H, m), 2.78 (6H, s), 3.19-3.24 (2H, m), 3.99 (3H, s), 4.20-4.26 (2H, m), 4.37 (2H, t), 4.47-4.54 (2H, m), 7.04 (1H, d), 7.46 (1H, d), 8.03 (1H, d), 8.48 (1H, dd), 8.77 (1H, d).

Example 19

Preparation of 6-amino-N-{8-[3-(1,1-dioxidothiomorpholin-4-yl)propoxy]-7-methoxy-2,3-dihydroimidazo[1,2-c]quinazolin-5-yl}nicotinamide

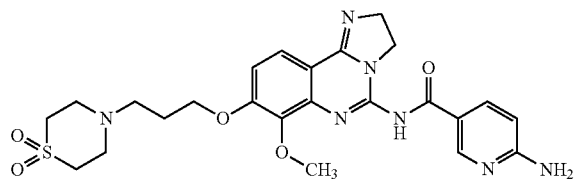 [SMILES: COc1c(OCCCN2CCS(=O)(=O)CC2)ccc2c1N=C(NC(=O)c1ccc(N)nc1)N1CCN=C21]

Step 1: Preparation of 8-[3-(1,1-dioxidothiomorpholin-4-yl)propoxy]-7-methoxy-2,3-dihydroimidazo[1,2-c]quinazolin-5-amine

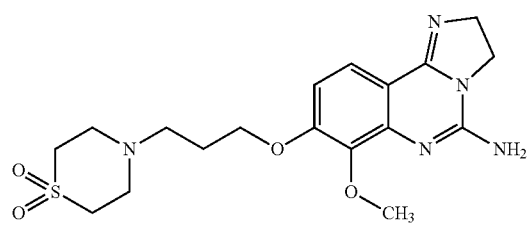 [SMILES: COc1c(OCCCN2CCS(=O)(=O)CC2)ccc2c1N=C(N)N1CCN=C21]

The procedure used for the preparation of Example 4 was used to prepare the title compound from 5-amino-7-methoxy-2,3-dihydroimidazo[1,2-c]quinazolin-8-ol bistrifluoroacetate salt (Intermediate A) and 3-(1,1-dioxidothiomorpholin-4-yl)propan-1-ol. High vacuum drying gave the title compound (1.48 g, 83%): HPLC MS RT=0.26 min, MH$^+$=408.3; $^1$H NMR (DMSO-d$_6$+2 drops TFA-d) δ: 2.23-2.25 (2H, m), 3.43-3.48 (2H, m), 3.81-3.84 (7H, m), 4.19-4.22 (2H, m), 4.27 (2H, t), 4.33-4.36 (2H, m), 7.30 (1H, d), 7.92 (1H, d).

Step 2: Preparation of 6-amino-N-{8-[3-(1,1-dioxidothiomorpholin-4-yl)propoxy]-7-methoxy-2,3-dihydroimidazo[1,2-c]quinazolin-5-yl}nicotinamide

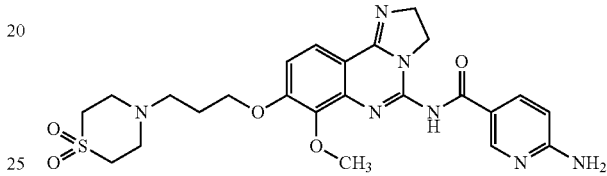

The procedure used for the preparation of Example 16, Step 2 was used to prepare the title compound from 8-[3-(1,1-dioxidothiomorpholin-4-yl)propoxy]-7-methoxy-2,3-dihydroimidazo[1,2-c]quinazolin-5-amine (Step 1) and 6-aminonicotinic acid. High vacuum drying gave the title compound (135 mg, 69%): HPLC MS RT=1.16 min, MH$^+$=528.1; $^1$H NMR (DMSO-d$_6$+2 drops TFA-d) δ: 2.24-2.29 (2H, m), 3.43-3.49 (2H, m), 3.60-3.62 (4H, m), 3.82 (4H, bs), 3.99 (3H, s), 4.23-4.27 (2H, m), 4.33 (2H, t), 4.48-4.54 (2H, m), 7.05 (1H, d), 7.44 (1H, d), 8.04 (1H, d), 8.47 (1H, dd), 8.77 (1H, d).

Example 20

Preparation of 6-amino-N-(7-methoxy-8-{[4-(methylsulfonyl)benzyl]oxy}-2,3-dihydroimidazo[1,2-c]quinazolin-5-yl)nicotinamide

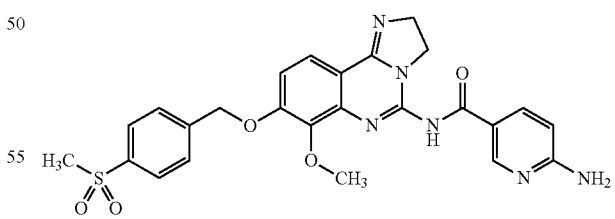

The procedure used for the preparation of Example 16, Step 2 was used to prepare the title compound from 7-methoxy-8-{[4-(methylsulfonyl)benzyl]oxy}-2,3-dihydroimidazo[1,2-c]quinazolin-5-amine (Example 16 Step 1) and 6-aminonicotinic acid. High vacuum drying gave the title compound (151 mg, 77%): HPLC MS RT=2.00 min, MH$^+$=521.1; $^1$H NMR (DMSO-d$_6$+2 drops TFA-d) δ: 3.24 (3H, s), 4.02 (3H, s), 4.23-4.28 (2H, m), 4.50-4.55 (2H, m), 5.56 (2H, s), 7.06 (1H, d), 7.58 (1H, d), 7.79 (2H, d), 8.01 (1H, d), 8.05 (1H, d), 8.50 (1H, dd), 8.79 (1H, d).

Example 21

Preparation of 2-amino-N-{8-[3-(1,1-dioxidothiomorpholin-4-yl)propoxy]-7-methoxy-2,3-dihydroimidazo[1,2-c]quinazolin-5-yl}pyrimidine-5-carboxamide

The procedure used for the preparation of Example 16, Step 2 was used to prepare the title compound from 8-[3-(1,1-dioxidothiomorpholin-4-yl)propoxy]-7-methoxy-2,3-dihydroimidazo[1,2-c]quinazolin-5-amine (Example 19, Step 1) and 2-aminopyrimidine-5-carboxylic acid. High vacuum drying at 60° C. gave the title compound (272 mg, 79%): HPLC MS RT=1.45 min, MH$^+$=529.2; $^1$H NMR (DMSO-d$_6$+2 drops TFA-d) δ: 2.25-2.30 (2H, m), 3.44-3.49 (2H, m), 3.61-3.63 (4H, m), 3.83 (4H, bs), 3.99 (3H, s), 4.18-4.25 (2H, m), 4.33 (2H, t), 4.48-4.55 (2H, m), 7.43 (1H, d), 8.02 (1H, d), 9.04 (2H, s).

Example 22

Preparation of 6-amino-N-{7-methoxy-8-[3-(morpholin-4-ylsulfonyl)propoxy]-2,3-dihydroimidazo[1,2-c]quinazolin-5-yl}nicotinamide

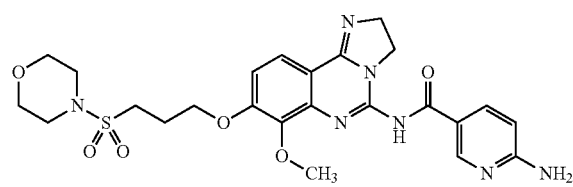 [SMILES: COc1c(OCCCS(=O)(=O)N2CCOCC2)ccc2c1N=C(NC(=O)c1ccc(N)nc1)N1CCN=C21]

Step 1: Preparation of 7-methoxy-8-[3-(morpholin-4-ylsulfonyl)propoxy]-2,3-dihydroimidazo[1,2-c]quinazolin-5-amine

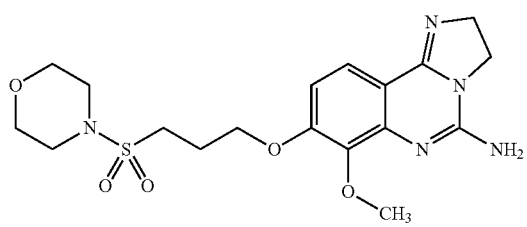 [SMILES: COc1c(OCCCS(=O)(=O)N2CCOCC2)ccc2c1N=C(N)N1CCN=C21]

The procedure used for the preparation of Example 1 was used to prepare the title compound from 5-amino-7-methoxy-2,3-dihydroimidazo[1,2-c]quinazolin-8-ol bistrifluoroacetate salt (Intermediate A) and 4-[(3-chloropropyl)sulfonyl]morpholine (Intermediate E). High vacuum drying gave the title compound (100%): $^1$H NMR (DMSO-d$_6$+2 drops TFA-d) δ: 2.17-2.22 (2H, m), 3.14-3.17 (4H, m), 3.22-3.27 (2H, m), 3.61-64 (4H, m), 3.83 (3H, s), 4.16-4.20 (2H, m), 4.28-4.35 (4H, m), 7.30 (1H, d), 7.89 (1H, d).

Step 2: Preparation of 6-amino-N-{7-methoxy-8-[3-(morpholin-4-ylsulfonyl)propoxy]-2,3-dihydroimidazo[1,2-c]quinazolin-5-yl}nicotinamide

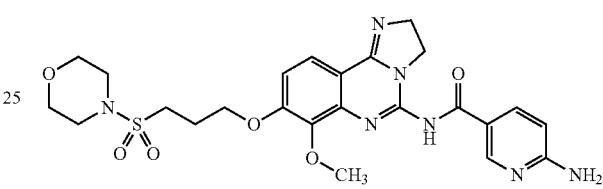

The procedure used for the preparation of Example 16, Step 2 was used to prepare the title compound from 7-methoxy-8-[3-(morpholin-4-ylsulfonyl)propoxy]-2,3-dihydroimidazo[1,2-c]quinazolin-5-amine (Step 1) and 6-aminonicotinic acid. High vacuum drying gave the title compound (122 mg, 63%): HPLC MS RT=1.96 min, MH$^+$=544.2; $^1$H NMR (DMSO-d$_6$+2 drops TFA-d) δ: 2.22-2.27 (2H, m), 3.15-3.18 (4H, m), 3.24-3.29 (2H, m), 3.61-3.65 (4H, m), 3.99 (3H, s), 4.24-4.27 (2H, m), 4.38 (2H, t), 4.48-4.52 (2H, m), 7.05 (1H, d), 7.47 (1H, d), 8.04 (1H, d), 8.49 (1H, dd), 8.78 (1H, d).

Example 23

Preparation of 2-amino-N-{7-methoxy-8-[3-(morpholin-4-ylsulfonyl)propoxy]-2,3-dihydroimidazo[1,2-c]quinazolin-5-yl}pyrimidine-5-carboxamide

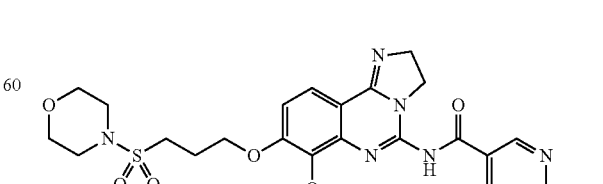

Step 1: Preparation of tert-butyl[5-({7-methoxy-8-[3-(morpholin-4-ylsulfonyl)propoxy]-2,3-dihydroimidazo[1,2-c]quinazolin-5-yl}carbamoyl)pyrimidin-2-yl]carbamate

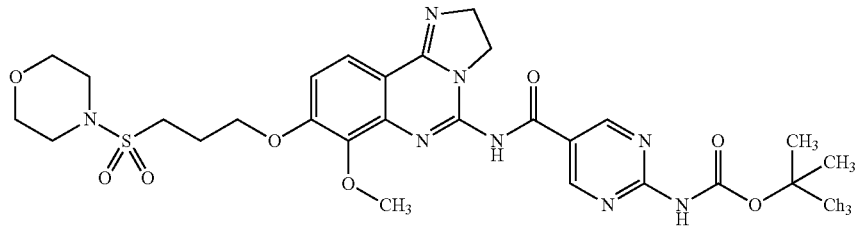

The procedure used for the preparation of Example 16, Step 2 was used to prepare the title compound from 7-methoxy-8-[3-(morpholin-4-ylsulfonyl)propoxy]-2,3-dihydroimidazo[1,2-c]quinazolin-5-amine (Example 22, Step 1) and 2-[(tert-butoxycarbonyl)amino]pyrimidine-5-carboxylic acid. High vacuum drying gave the title compound (227 mg, 74%): HPLC MS RT=2.57 min, MH$^+$=645.1; $^1$H NMR (DMSO-d$_6$+2 drops TFA-d) δ: 1.46 (9H, s), 2.22-2.27 (2H, m), 3.15-3.18 (4H, m), 3.24-3.29 (2H, m), 3.62-3.65 (4H, m), 4.00 (3H, s), 4.20-4.27 (2H, m), 4.38 (2H, t), 4.52-4.58 (2H, m), 7.47 (1H, d), 8.03 (1H, d), 9.26 (2H, s).

Step 2: Preparation of 2-amino-N-{7-methoxy-8-[3-(morpholin-4-ylsulfonyl)propoxy]-2,3-dihydroimidazo[1,2-c]quinazolin-5-yl}pyrimidine-5-carboxamide

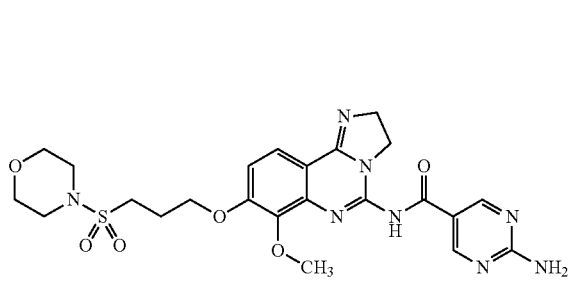 [SMILES: COc1c(OCCCS(=O)(=O)N2CCOCC2)ccc2c1N=C(NC(=O)c1cnc(N)nc1)N1CCN=C21]

tert-Butyl[5-({7-methoxy-8-[3-(morpholin-4-ylsulfonyl)propoxy]-2,3-dihydroimidazo[1,2-c]quinazolin-5-yl}carbamoyl)pyrimidin-2-yl]carbamate (Step 1, 150 mg 0.26 mmol) was dissolved in CH$_2$Cl$_2$ (15 mL) and TFA (0.16 mL, 2.1 mmol) was added dropwise. The mixture was stirred at rt over 2 d, after which 5 drops of Et$_3$N were added causing a solid to precipitate. The mixture was stirred overnight, then the solvents removed under reduced pressure. The resulting residue was triturated in EtOAc (15 mL), collected by vacuum filtration and washed further with EtOAc (10 mL). This solid was then triturated in water (5 mL) collected by vacuum filtration and washed further with water (10 mL). High vacuum drying gave the title compound (172 mg, 92%): HPLC MS RT=0.87 min, MH$^+$=545.2; $^1$H NMR (DMSO-d$_6$+2 drops TFA-d) δ: 2.21-2.26 (2H, m), 3.15-3.18 (4H, m), 3.24-3.29 (2H, m), 3.61-3.65 (4H, m), 3.99 (3H, s), 4.18-4.25 (2H, m), 4.37 (2H, t), 4.48-4.55 (2H, m), 7.44 (1H, d), 8.02 (1H, d), 9.06 (2H, s).

Example 24

Preparation of N-{8-[3-(morpholin-4-ylsulfonyl)propoxy]-2,3-dihydroimidazo[1,2-c]quinazolin-5-yl}nicotinamide

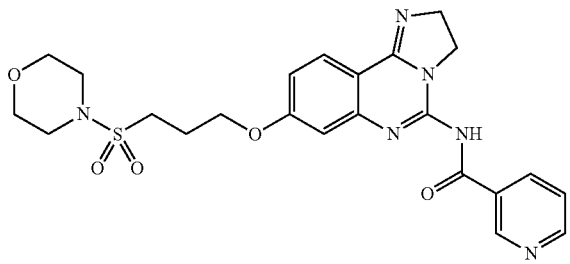 [SMILES: O=C(NC1=Nc2cc(OCCCS(=O)(=O)N3CCOCC3)ccc2C2=NCCN12)c1cccnc1]

To N-(8-hydroxy-2,3-dihydroimidazo[1,2-c]quinazolin-5-yl)nicotinamide (Example 2-5 in WO2004029055, 250 mg, 0.001 mol) and K$_2$CO$_3$ (1.1 g, 0.008 mol) in DMF (5 ml) was added 4-[(3-chloropropyl)sulfonyl]morpholine (Intermediate E, 204.0 mg, 0.001 mol) to a sealed tube and heated to 120° C. for 3 h. The reaction was poured into water and extracted with CH$_2$Cl$_2$. Organic layers dried with MgSO$_4$, filtered and concentrated. The residue was purified using silica gel flash chromatography (100% EtOAc, then 0-20% MeOH/CH$_2$Cl$_2$) to provide the title compound (130 mg, 33%). TLC: R$_f$=0.21 in 10% MeOH/CH$_2$Cl$_2$, HPLC MS RT=1.81 min., MW=499.1; $^1$H NMR (DMSO-d$_6$+2 drops TFA-d) δ: 2.22 (2H, m), 3.17 (4H, m), 3.26 (2H, m), 3.64 (4H, m), 4.18-4.29 (4H, m), 4.56 (2H, m), 7.22 (1H, d), 7.74 (1H, s), 7.89 (1H, m), 8.12 (1H, d), 8.81 (1H, m), 8.95 (1H, dd), 9.44 (1H, s).

Example 25

Preparation of N-(8-{3-[(4-methylpiperazin-1-yl)sulfonyl]propoxy}-2,3-dihydroimidazo[1,2-c]quinazolin-5-yl)nicotinamide

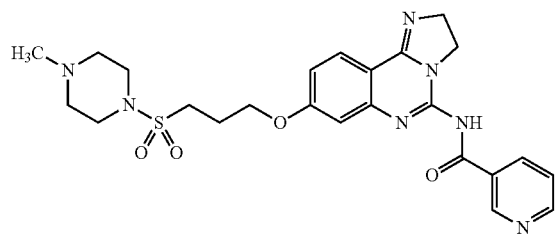 [SMILES: CN1CCN(S(=O)(=O)CCCOc2ccc3c(c2)N=C(NC(=O)c2cccnc2)N2CCN=C32)CC1]

The procedure used for the preparation of Example 24 was used to prepare the title compound from N-(8-hydroxy-2,3-dihydroimidazo[1,2-c]quinazolin-5-yl)nicotinamide (Example 2-5 in WO2004029055) and 1-[(3-chloropropyl)sulfonyl]-4-methylpiperazine (Intermediate D) (70 mg, 16%). TLC: $R_f$=0.08 in 10% MeOH/CH$_2$Cl$_2$, HPLC MS RT=1.06 min, MH$^+$=512.1; $^1$H NMR (DMSO-d$_6$) δ: 2.12-2.37 (2H, m), 2.37 (3H, s), 3.15-3.23 (6H, m), 3.30-3.33 (4H, m), 4.00-4.20 (6H, m), 6.84 (1H, d), 7.29 (1H, s), 7.51 (1H, dd), 7.75 (1H, d), 8.41 (1H, d), 8.70 (1H, m), 9.28 (1H, s), 12.29 (1H, s).

Example 26

Preparation of N-(8-{[4-(methylsulfonyl)benzyl]oxy}-2,3-dihydroimidazo[1,2-c]quinazolin-5-yl)nicotinamide

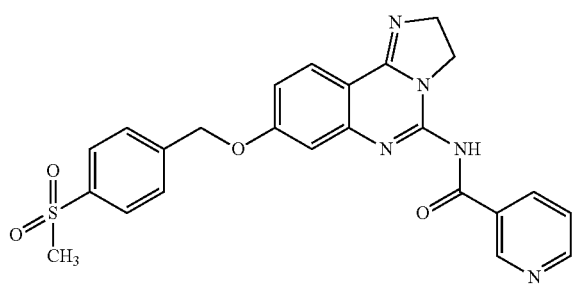 [SMILES: CS(=O)(=O)c1ccc(COc2ccc3c(c2)N=C(NC(=O)c2cccnc2)N2CCN=C32)cc1]

The procedure used for the preparation of Example 24 was used to prepare the title compound from N-(8-hydroxy-2,3-dihydroimidazo[1,2-c]quinazolin-5-yl)nicotinamide (Example 2-5 in WO2004029055) and 1-(chloromethyl)-4-(methylsulfonyl)benzene (20 mg, 4%). TLC: $R_f$=0.91 in 10% MeOH/CH$_2$Cl$_2$, HPLC MS RT=1.91 min, MH$^+$=476.2; $^1$H NMR (DMSO-d$_6$) δ: 3.22 (3H, s), 4.00-4.15 (4H, m), 5.33 (2H, s), 6.93 (1H, d), 7.39 (1H, s), 7.51 (1H, dd), 7.71 (2H, d), 7.78 (1H, d), 7.95 (2H, d), 8.42 (1H, d), 8.70 (1H, m), 9.29 (1H, s), 12.31 (1H, s).

Example 27

Preparation of 2,4-dimethyl-N-(8-{[4-(methylsulfonyl)benzyl]oxy}-2,3-dihydroimidazo[1,2-c]quinazolin-5-yl)-1,3-thiazole-5-carboxamide

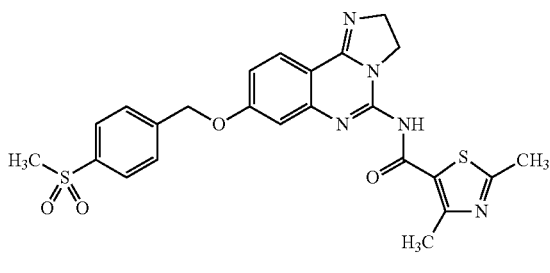

Step 1: Preparation of N-(8-methoxy-2,3-dihydroimidazo[1,2-c]quinazolin-5-yl)-2,4-dimethyl-1,3-thiazole-5-carboxamide

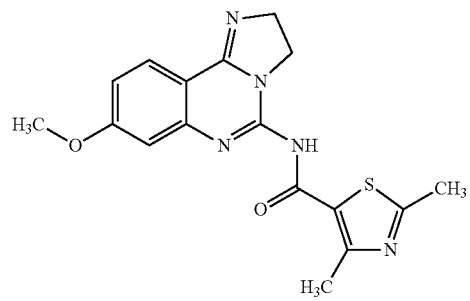

The procedure used for the preparation of Example 16, Step 2 was used to prepare the title compound from 8-methoxy-2,3-dihydroimidazo[1,2-c]quinazolin-5-amine hydrobromide (Intermediate I, Step 3) and 2,4-dimethyl-1,3-thiazole-5-carboxylic acid as white solid (4.26 g, 77%): HPLC MS RT=2.05 min, MH$^+$=356.1;

Step 2: Preparation of N-(8-hydroxy-2,3-dihydroimidazo[1,2-c]quinazolin-5-yl)-2,4-dimethyl-1,3-thiazole-5-carboxamide

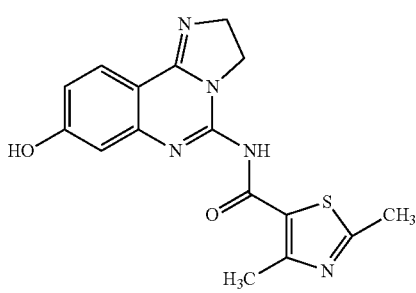 [SMILES: Cc1nc(C)c(C(=O)NC2=Nc3cc(O)ccc3C3=NCCN23)s1]

Step 3: Preparation of 2,4-dimethyl-N-(8-{[4-(methylsulfonyl)benzyl]oxy}-2,3-dihydroimidazo[1,2-c]quinazolin-5-yl)-1,3-thiazole-5-carboxamide

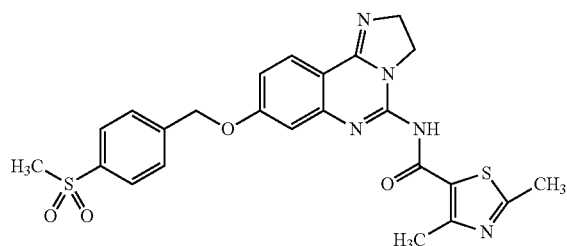

The procedure used for the preparation of Example 24, Step 2 was used to prepare the title compound from N-(8-hydroxy-2,3-dihydroimidazo[1,2-c]quinazolin-5-yl)-2,4-dimethyl-1,3-thiazole-5-carboxamide (Step 1) and 1-(chloromethyl)-4-(methylsulfonyl)benzene (15 mg, 51%). TLC: R$_f$ 0.93 in 10% MeOH/CH$_2$Cl$_2$, HPLC MS RT=2.27 min, MH$^+$=510.1; $^1$H NMR (DMSO-d$_6$) δ: 2.80 (3H, s), 2.86 (3H, s), 3.39 (3H, s), 4.30-4.35 (2H, m), 4.50-4.54 (2H, m), 5.56 (2H, s), 7.39 (1H, d), 7.87 (2H, d), 7.95 (1H, s), 8.11 (2H, d), 8.50 (1H, d).

Example 28

Preparation of N-{8-[3-(morpholin-4-ylsulfonyl)propoxy]-2,3-dihydroimidazo[1,2-c]quinazolin-5-yl}pyrimidine-5-carboxamide

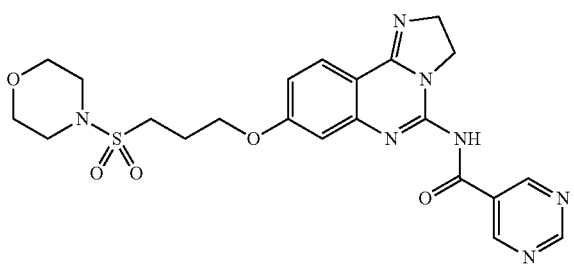 [SMILES: O=C(NC1=Nc2cc(OCCCS(=O)(=O)N3CCOCC3)ccc2C2=NCCN12)c1cncnc1]

Step 1: Preparation of 8-[3-(morpholin-4-ylsulfonyl)propoxy]-2,3-dihydroimidazo[1,2-c]quinazolin-5-amine

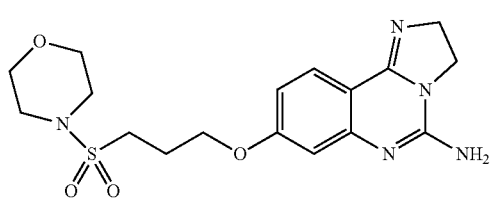 [SMILES: NC1=Nc2cc(OCCCS(=O)(=O)N3CCOCC3)ccc2C2=NCCN12]

The procedure used for the preparation of Example 24, Step 2 was used to prepare the title compound from 5-amino-2,3-dihydroimidazo[1,2-c]quinazolin-8-ol (Intermediate I) and 4-[(3-chloropropyl)sulfonyl]morpholine (Intermediate E). Yield 190 mg (61%). R$_f$=0.68 in 10% MeOH/CH$_2$Cl$_2$, HPLC MS RT=1.13 min, MH$^+$=394.4.

Step 2: Preparation of N-{8-[3-(morpholin-4-ylsulfonyl)propoxy]-2,3-dihydroimidazo[1,2-c]quinazolin-5-yl}pyrimidine-5-carboxamide

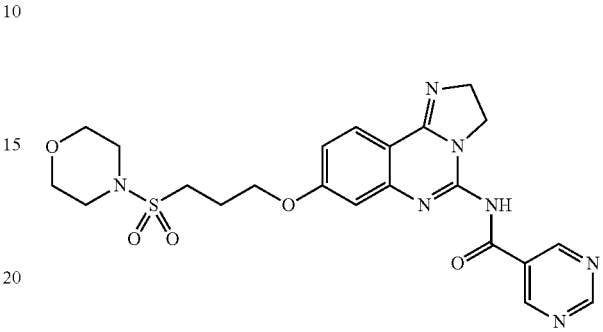

To pyrimidine-5-carboxylic acid (95.0 mg, 0.77 mmol) in DMF (1 ml) was added HATU (342 mg, 0.9 mmol) and 4-methylmorpholine (91 mg, 0.9 mmol). The mixture was stirred for 5 min then 8-[3-(morpholin-4-ylsulfonyl)propoxy]-2,3-dihydroimidazo[1,2-c]quinazolin-5-amine (Step 1, 250 mg, 0.64 mmol) in DMF (2 mL) was added. The resulting solution was allowed to stir at rt for 16 h. It was diluted with EtOAc and filtered rinsing with EtOAc and MeOH to give the title compound (195 mg, 61%). TLC R$_f$=0.68 in 10% MeOH/CH$_2$Cl$_2$, HPLC MS RT=1.13 min, MH$^+$=500.4; $^1$H NMR (DMSO-d$_6$) δ: 2.25 (2H, m), 3.21 (4H, m), 3.30 (2H, m), 3.67 (4H, m), 4.23 (2H, t), 4.31 (2H, t), 4.60 (2H, t), 7.25 (1H, d), 7.78 (1H, s), 8.16 (1H, d), 9.44 (1H, s), 9.50 (2H, s).

Example 29

Preparation of 2-amino-N-{8-[3-(morpholin-4-ylsulfonyl)propoxy]-2,3-dihydroimidazo[1,2-c]quinazolin-5-yl}pyrimidine-5-carboxamide

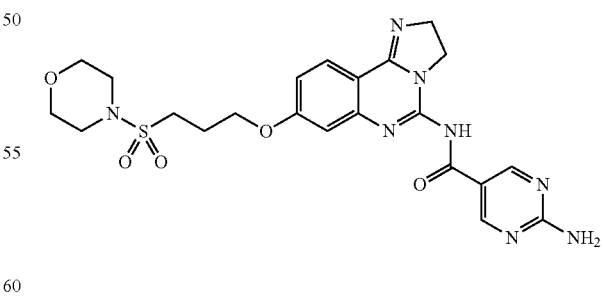

The procedure used for the preparation of Example 28, Step 2 was used to prepare the title compound from 8-[3-(morpholin-4-ylsulfonyl)propoxy]-2,3-dihydroimidazo[1,2-c]quinazolin-5-amine (Example 28, Step 1) and 2-aminopyrimidine-5-carboxylic acid. Yield 150 mg (45%). TLC R$_f$=0.47 in 10% MeOH/CH$_2$Cl$_2$, HPLC MS RT=0.76 min, MH$^+$=515.4; $^1$H NMR (DMSO-d$_6$) δ: 2.24 (2H, m), 3.21 (4H, m), 3.29 (2H, m), 3.67 (4H, m), 4.20 (2H, t), 4.30 (2H, t), 4.53 (2H, t), 7.20 (1H, d), 7.70 (1H, br s), 7.97 (1H, s), 8.13 (1H, d), 9.02 (2H, s).

Example 30

Preparation of 6-amino-N-{8-[3-(morpholin-4-ylsulfonyl)propoxy]-2,3-dihydroimidazo[1,2-c]quinazolin-5-yl}nicotinamide

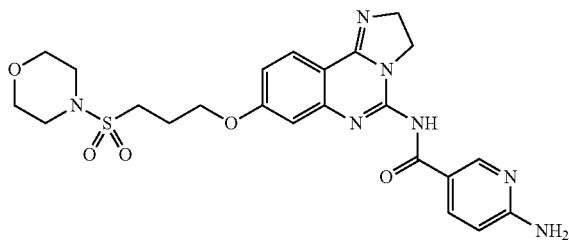 [SMILES: Nc1ccc(C(=O)NC2=Nc3cc(OCCCS(=O)(=O)N4CCOCC4)ccc3C3=NCCN23)cn1]

The procedure used for the preparation of Example 28, Step 2 was used to prepare the title compound from 8-[3-(morpholin-4-ylsulfonyl)propoxy]-2,3-dihydroimidazo[1,2-c]quinazolin-5-amine (Example 28, Step 1) and 6-aminonicotinic acid. Yield 50.0 mg (14%). TLC $R_f$=0.52 in 10% MeOH/CH$_2$Cl$_2$, HPLC MS RT=0.23 min, MH$^+$=514.4; $^1$H NMR (MeOD) δ: 2.35 (2H, m), 3.20-3.33 (6H, m), 3.72 (4H, m), 4.26 (2H, t), 4.35 (2H, t), 4.63 (2H, t), 7.06 (1H, d), 7.19 (1H, dd), 7.36 (1H, s), 8.04 (1H, d), 8.56 (1H, dd), 8.74 (1H, s).

Example 31

Preparation of N-[7-methoxy-8-(2-{2-[(methylsulfonyl)amino]ethoxy}ethoxy)-2,3-dihydroimidazo[1,2-c]quinazolin-5-yl]nicotinamide

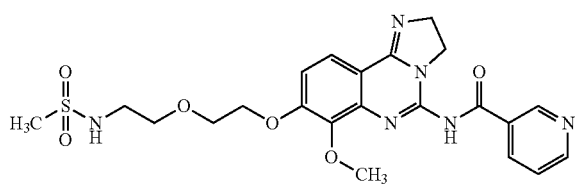 [SMILES: COc1c(OCCOCCNS(C)(=O)=O)ccc2c1N=C(NC(=O)c1cccnc1)N1CCN=C21]

Step 1: Preparation of tert-butyl[2-(2-hydroxyethoxy)ethyl]carbamate

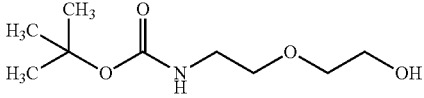

Di-tert-butyl dicarbonate (10.3 g, 47 mmol) was diluted in chloroform (200 mL) and carefully added to a solution of 2-(2-amino-ethoxy)-ethanol (5.00 g, 47 mmol) in chloroform (200 mL). After stirring at rt for 1.5 h, water was added and the organic layer was separated. The aqueous layer was extracted with dichloromethane, and the combined organics were dried over sodium sulfate and concentrated in vacuo to give the desired compound as a clear colorless oil (9.3 g, 96%). The material was used in the subsequent step without further purification. $^1$H NMR (CDCl$_3$) δ: 1.45 (9H, s), 3.33 (2H, t), 3.57 (4H, m), 3.74 (2H, t).

Step 2: Preparation of 2-{2-[(tert-butoxycarbonyl)amino]ethoxy}ethyl methanesulfonate

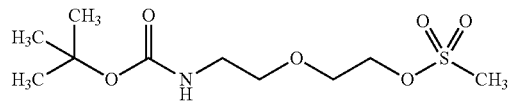 [SMILES: CC(C)(C)OC(=O)NCCOCCOS(C)(=O)=O]

tert-Butyl[2-(2-hydroxyethoxy)ethyl]carbamate (Step 1, 3.73 g, 18 mmol) was diluted in dichloromethane (75 mL) and cooled to 0° C. Triethylamine (3.0 mL, 22 mmol) was added, followed by methanesulfonyl chloride (1.7 mL, 22 mmol). After stirring at rt for 1 h, water was added. The aqueous layer was separated and extracted with dichloromethane. The combined organics were dried and concentrated in vacuo to afford the title compound as an oil. $^1$H NMR (CDCl$_3$) δ: 1.44 (9H, s), 3.06 (3H, s), 3.32 (2H, m), 3.56 (2H, t), 3.72 (2H, m), 4.36 (2H, m).

Step 3: Preparation of tert-butyl {2-[2-({7-methoxy-5-[(pyridin-3-ylcarbonyl)amino]-2,3-dihydroimidazo[1,2-c]quinazolin-8-yl}oxy)ethoxy]ethyl}carbamate

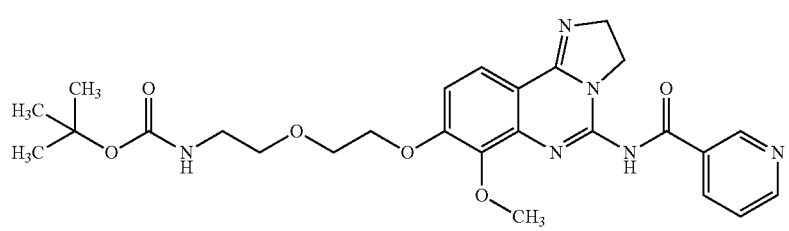 [SMILES: COc1c(OCCOCCNC(=O)OC(C)(C)C)ccc2c1N=C(NC(=O)c1cccnc1)N1CCN=C21]

N-(8-Hydroxy-7-methoxy-2,3-dihydroimidazo[1,2-c]quinazolin-5-yl)pyrimidine-5-carboxamide (Intermediate B, 4.2 g, 7.4 mmol) was diluted in dimethylformamide (75 mL). Cesium carbonate (12.1 g, 37.1 mmol) was added, followed by 2-{2-[(tert-butoxycarbonyl)amino]ethoxy}ethyl methanesulfonate (Step 2, 5.26 g, 18.6 mmol). The mixture was stirred at 50° C. overnight. After cooling to rt, water was added and the mixture was cooled to 0° C. for 30 min. The product was isolated by vacuum filtration, washing with water, and dried in the vacuum oven. The title compound was obtained as an orange solid (3.55 g, 91%). HPLC MS RT=2.23 min, MH$^+$=525.1. $^1$H NMR (DMSO-d$_6$+2 drops TFA-d) δ: 1.35 (9H, s), 3.07 (2H, t), 3.46 (2H, t), 3.81 (2H, m), 4.02 (3H, s), 4.25 (2H, m), 4.40 (2H, m), 4.57 (2H, m), 7.49 (1H, d), 7.85 (1H, m), 8.03 (1H, d), 8.82 (1H, m), 8.93 (1H, m), 9.48 (1H, m).

Step 4: Preparation of N-{8-[2-(2-aminoethoxy)-ethoxy]-7-methoxy-2,3-dihydro-imidazo[1,2-c]quinazolin-5-yl}-nicotinamide

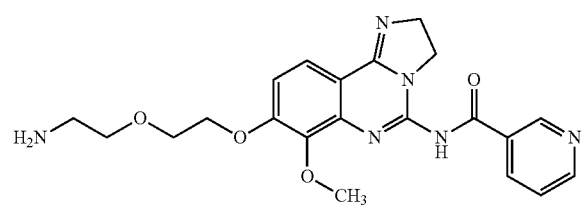 [SMILES: COc1c(OCCOCCN)ccc2c1N=C(NC(=O)c1cccnc1)N1CCN=C21]

tert-Butyl {2-[2-({7-methoxy-5-[(pyridin-3-ylcarbonyl)amino]-2,3-dihydroimidazo[1,2-c]quinazolin-8-yl}oxy)ethoxy]ethyl}carbamate (Step 3, 3.6 g, 6.8 mmol) was diluted in a mixture of trifluoroacetic acid (18 mL) and dichloromethane (70 mL). The mixture was stirred at rt overnight, then was concentrated in vacuo. The resultant orange oil was redissolved in dichloromethane and treated with an excess of triethylamine. After stirring at rt for 0.5 h, the solvent was evaporated under reduced pressure and the residue triturated with ethyl acetate. The title compound was isolated by vacuum filtration and dried in the vacuum oven. This material was contaminated with a small amount of triethylamine, but was suitable for use in the next step as is. HPLC MS RT=1.09 min, MH$^+$=425.2. $^1$H NMR (DMSO-d$_6$+2 drops TFA-d) δ: 3.01 (2H, m), 3.69 (2H, t), 3.89 (2H, m), 4.02 (3H, s), 4.26 (2H, m), 4.44 (2H, m), 4.57 (2H, m), 7.49 (1H, d), 7.76 (1H, m), 8.05 (1H, d), 8.72 (1H, m), 8.89 (1H, m), 9.44 (1H, m).

Step 5: Preparation of N-[7-methoxy-8-(2-{2-[(methylsulfonyl)amino]ethoxy}ethoxy)-2,3-dihydroimidazo[1,2-c]quinazolin-5-yl]nicotinamide

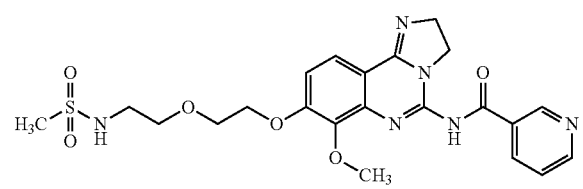 [SMILES: COc1c(OCCOCCNS(C)(=O)=O)ccc2c1N=C(NC(=O)c1cccnc1)N1CCN=C21]

N-{8-[2-(2-Aminoethoxy)-ethoxy]-7-methoxy-2,3-dihydro-imidazo[1,2-c]quinazolin-5-yl}-nicotinamide (Step 4, 75 mg, 0.18 mmol) was dissolved in dimethylformamide (2 mL). N,N-diisopropylethylamine (0.03 mL) was added, followed by methanesulfonyl chloride (0.01 mL, 0.14 mmol). The mixture was stirred at rt for 3 h, then was quenched by the addition of water. Saturated aqueous sodium bicarbonate was added, and the mixture was extracted several times with dichloromethane. The combined organic extracts were dried and concentrated to afford a residue, which was purified by preparative HPLC (gradient elution of 10-70% acetonitrile in water, 0.1% TFA). The product fractions were free based with saturated aqueous sodium bicarbonate, and the desired was isolated by extraction with dichloromethane. The organic layer was dried over sodium sulfate, and concentrated to give the title compound (8.7 mg, 12%). HPLC MS RT=1.79 min, MH$^+$=503.2. $^1$H NMR (DMSO-d$_6$+2 drops TFA-d) δ: 2.89 (3H, s), 3.11 (2H, t), 3.56 (2H, t), 3.85 (2H, m), 4.03 (3H, s), 4.26 (2H, m), 4.43 (2H, m), 4.57 (2H, m), 7.50 (1H, d), 7.86 (1H, m), 8.02 (1H, d), 8.83 (1H, m), 8.94 (1H, m), 9.47 (1H, m).

Example 32

Preparation of N-[7-methoxy-8-(2-{2-[(propylsulfonyl)amino]ethoxy}ethoxy)-2,3-dihydroimidazo[1,2-c]quinazolin-5-yl]nicotinamide

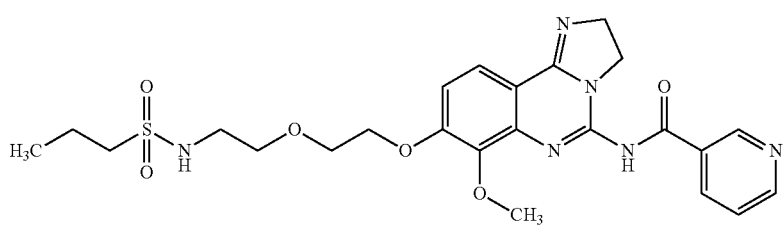 [SMILES: CCCS(=O)(=O)NCCOCCOc1ccc2c(c1OC)N=C(NC(=O)c1cccnc1)N1CCN=C21]

The procedure used for the preparation of Example 31, Step 5 was used to prepare the title compound from N-{8-[2-(2-aminoethoxy)-ethoxy]-7-methoxy-2,3-dihydro-imidazo[1,2-c]quinazolin-5-yl}-nicotinamide (Example 31, Step 4) and propanesulfonyl chloride. HPLC MS RT=1.99 min, MH$^+$=531.3.

Example 33

Preparation of N-[7-methoxy-8-(2-{2-[(phenylsulfonyl)amino]ethoxy}ethoxy)-2,3-dihydroimidazo[1,2-c]quinazolin-5-yl]nicotinamide

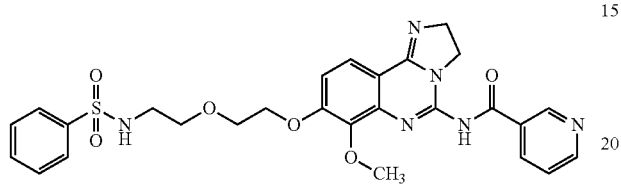

The procedure used for the preparation of Example 31, Step 5 was used to prepare the title compound from N-{8-[2-(2-aminoethoxy)-ethoxy]-7-methoxy-2,3-dihydro-imidazo[1,2-c]quinazolin-5-yl}-nicotinamide (Example 31, Step 4) and phenylsulfonyl chloride. HPLC MS RT=2.25 min, MH$^+$=565.3.

Example 34

Preparation of N-{7-methoxy-8-[2-(2-{[(4-methylphenyl)sulfonyl]amino}ethoxy)ethoxy]-2,3-dihydroimidazo[1,2-c]quinazolin-5-yl}nicotinamide

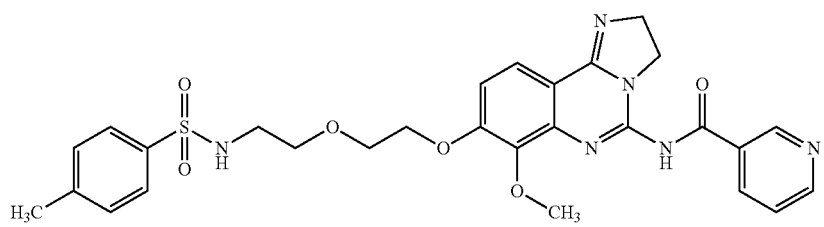 [SMILES: COc1c(OCCOCCNS(=O)(=O)c2ccc(C)cc2)ccc2c1N=C(NC(=O)c1cccnc1)N1CCN=C21]

The procedure used for the preparation of Example 31, Step 5 was used to prepare the title compound from N-{8-[2-(2-aminoethoxy)-ethoxy]-7-methoxy-2,3-dihydro-imidazo[1,2-c]quinazolin-5-yl}-nicotinamide (Example 31, Step 4) and (4-methylphenyl)sulfonyl chloride. HPLC MS RT=2.35 min, MH$^+$=579.5.

Example 35

Preparation of N-(8-[3-[(ethylsulfonyl)amino]propoxy]-7-methoxy-2,3-dihydroimidazo[1,2-c]quinazolin-5-yl)nicotinamide

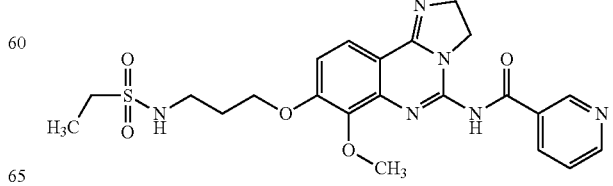

Step 1: Synthesis of tert-butyl[3-({7-methoxy-5-[(pyridin-3-ylcarbonyl)amino]-2,3-dihydroimidazo[1,2-c]quinazolin-8-yl}oxy)propyl]carbamate

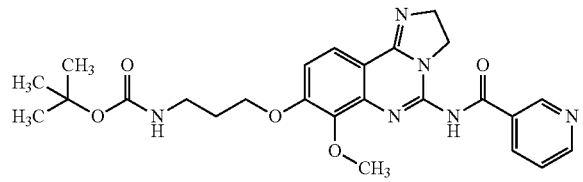 [SMILES: COc1c(OCCCNC(=O)OC(C)(C)C)ccc2c1N=C(NC(=O)c1cccnc1)N1CCN=C21]

N-(8-Hydroxy-7-methoxy-2,3-dihydroimidazo[1,2-c]quinazolin-5-yl)pyrimidine-5-carboxamide (Intermediate B, 1.5 g, 4.4 mmol) was diluted in dimethylformamide (50 mL) containing a few drops of water. Cesium carbonate (7.24 g, 22.2 mmol) and sodium iodide (0.80 g, 5.3 mmol) were added, followed by tert-butyl (3-bromopropyl)carbamate (3.18 g, 13.3 mmol). The mixture was stirred at 100° C. overnight. After cooling to rt, the solvent was removed in vacuo. The residue was diluted in 10% methanol in dichloromethane, and solids were removed by filtration. The filtrate was concentrated and purified by silica gel flash column chromatography, eluting with 0-10% methanol in dichloromethane, to afford the title compound (1.13 g, 51%). $^1$H NMR (DMSO-$d_6$+2 drops TFA-d) δ: 1.37 (9H, s), 1.94 (2H, m), 3.15 (2H, t), 4.03 (3H, s), 4.26 (4H, m), 4.57 (2H, m), 6.96 (1H, br t), 7.47 (1H, d), 7.82 (1H, m), 8.03 (1H, d), 8.79 (1H, m), 8.91 (1H, m), 9.46 (1H, m).

Step 2: Preparation of N-[8-(3-amino-propyloxy)-7-methoxy-2,3-dihydro-imidazo[1,2-c]quinazolin-5-yl]-nicotinamide hydrotrifluoroacetate

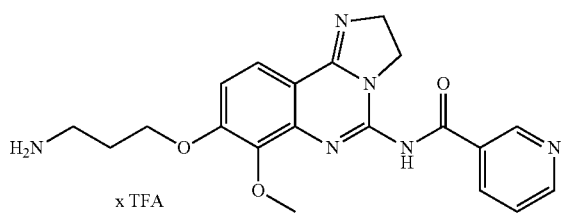 [SMILES: COc1c(OCCCN)ccc2c1N=C(NC(=O)c1cccnc1)N1CCN=C21]

tert-Butyl[3-({7-methoxy-5-[(pyridin-3-ylcarbonyl)amino]-2,3-dihydroimidazo[1,2-c]quinazolin-8-yl}oxy)propyl]carbamate (Step 1, 1.2 g, 2.3 mmol) was diluted in a mixture of trifluoroacetic acid (6 mL) and dichloromethane (24 mL). The mixture was stirred at rt overnight, then was concentrated in vacuo to afford a viscous yellow oil. Acetonitrile was added to the mixture, and the desired was isolated by vacuum filtration as a white solid (0.55 g, 60%). $^1$H NMR (DMSO-$d_6$+2 drops TFA-d) δ: 2.13 (2H, m), 3.02 (2H, m), 4.01 (3H, s), 4.25 (2H, m), 4.35 (2H, t), 4.57 (2H, m), 7.45 (1H, d), 7.73 (1H, m), 7.92 (2H, br m), 8.06 (1H, d), 8.69 (1H, m), 8.87 (1H, m), 9.43 (1H, m).

Step 3: Synthesis of N-(8-[3-[(ethylsulfonyl)amino]propoxy]-7-methoxy-2,3-dihydroimidazo[1,2-c]quinazolin-5-yl)nicotinamide

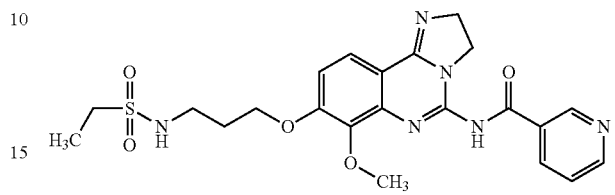

Ethanesulfonyl chloride (18 mg, 0.14 mmol) was diluted in dichloromethane (5 ml) and cooled to 0° C. A solution of N-[8-(3-amino-propyloxy)-7-methoxy-2,3-dihydro-imidazo[1,2-c]quinazolin-5-yl]-nicotinamide hydrotrifluoroacetate (Step 2, 50 mg, 0.13 mmol) in dimethylformamide (5 mL) was added dropwise, and the mixture was stirred at −10° C. for 30 min. Triethylamine (0.07 mL) was added dropwise, and stirring was continued at −10° C. for another 30 min. The reaction mixture was stirred at rt overnight. Another equivalent of ethanesulfonyl chloride was added, and the mixture was stirred at rt for 12 h. The reaction mixture was quenched by the addition of water, and was extracted with dichloromethane. The combined organic extracts were concentrated to afford a white solid, which was triturated with ethyl acetate to remove residual dimethylformamide. After filtration the solid was carefully washed with water and dried in a vacuum oven. The title compound was obtained as a white solid (4.2 mg, 6.8%). HPLC MS RT=1.63 min, MH$^+$=487.3. $^1$H NMR (DMSO-$d_6$+2 drops TFA-d) δ: 1.18 (3H, t), 2.00 (2H, m), 2.99 (2H, quartet), 3.14 (2H, t), 4.01 (3H, s), 4.23-4.34 (4H, m), 4.57 (2H, m), 7.49 (1H, d), 7.91 (1H, m), 8.04 (1H, d), 8.95 (1H, m), 8.96 (1H, m), 9.49 (1H, m).

Example 36

Preparation of N-[7-{[4-(methylsulfonyl)benzyl]oxy}-8-(3-morpholin-4-ylpropoxy)-2,3-dihydroimidazo[1,2-c]quinazolin-5-yl]nicotinamide

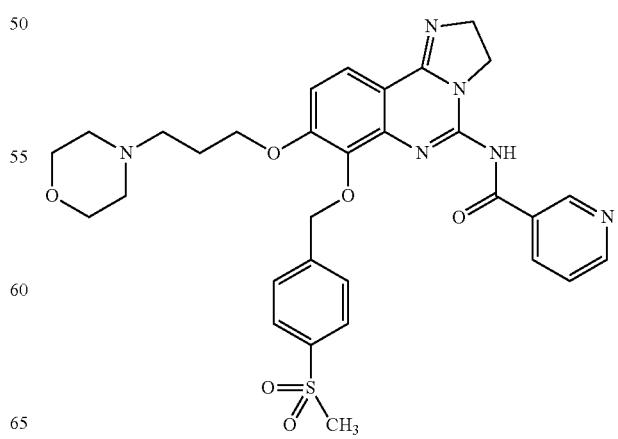

N-[7-Hydroxy-8-(3-morpholin-4-ylpropoxy)-2,3-dihydroimidazo[1,2-c]quinazolin-5-yl]nicotinamide (Intermediate H, 0.09 g, 0.20 mmol) was suspended in DMF (2.0 mL) and NaH (0.02 g, 0.30 mmol, 60%) were added. After 20 min at rt 1-(chloromethyl)-4-(methylsulfonyl)benzene (0.06 g, 0.30 mmol) was added and the mixture was stirred at it for 16 h. The DMF was evaporated under reduced pressure and the residue triturated with a mixture of ~10% MeOH in $CH_2Cl_2$ (4 mL). The mixture was vacuum filtered and the solids were washed well with $CH_2Cl_2$. The filtrate was concentrated under reduced pressure, and the residue purified via silica gel chromatography (0-6% MeOH/$CH_2Cl_2$). The fractions were combined, and the solvent was evaporated under reduced pressure. Drying under high vacuum gave the title compound (0.087 g, 70%): TLC (5% MeOH/$CH_2Cl_2$): $R_f$=0.47; HPLC MS RT=0.55 min, $[M+Na]^+$=641; $^1$H NMR (DMSO-$d_6$+2 drops TFA-d) δ: 2.21-2.35 (2H, m), 3.05-3.17 (2H, m), 3.22 (3H, s), 3.31 (2H, m), 3.42-3.52 (2H, m), 3.60-3.72 (2H, m), 3.94-4.04 (2H, m), 4.29 (2H, m), 4.39 (2H, t), 4.56 (2H, m), 5.37 (2H, s), 7.52 (1H, d), 7.72 (1H, dd), 7.85 (2H, d), 8.01 (2H, d), 8.10 (1H, d), 8.66 (1H, d), 8.89 (1H, dd), 9.43 (1H, s).

Example 37

Preparation of 8-(3-morpholin-4-ylpropoxy)-5-[(pyridin-3-ylcarbonyl)amino]-2,3-dihydroimidazo[1,2-c]quinazolin-7-yl methanesulfonate

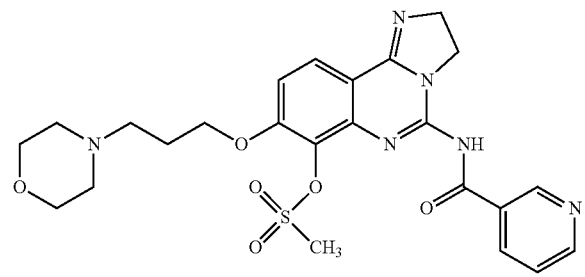 [SMILES: CS(=O)(=O)Oc1c(OCCCN2CCOCC2)ccc2c1N=C(NC(=O)c1cccnc1)N1CCN=C21]

The procedure used for the preparation of Example 36 was used to prepare the title compound from N-[7-hydroxy-8-(3-morpholin-4-ylpropoxy)-2,3-dihydroimidazo[1,2-c]quinazolin-5-yl]nicotinamide (Intermediate H) and methanesulfonyl chloride (58 mg, 49%). TLC: $R_f$=0.38 in 10% MeOH/$CH_2Cl_2$, HPLC MS RT=2.05 min, $[M+Na]^+$=551; $^1$H NMR (DMSO-$d_6$+2 drops TFA-d) δ: 2.18-2.30 (2H, m), 3.03-3.17 (2H, m), 3.28-3.37 (2H, m), 3.44-3.54 (2H, m), 3.60-3.75 (5H, m), 3.95-4.05 (2H, m), 4.19-4.29 (2H, m), 4.40 (2H, t), 4.56-4.66 (2H, m), 7.63 (1H, d), 7.82 (1H, dd), 8.29 (1H, d), 8.64 (1H, d), 8.93 (1H, dd), 9.35 (1H, s).

Biological Evaluation

The utility of the compounds of the present invention can be illustrated, for example, by their activity in vitro in the in vitro tumor cell proliferation assay described below. The link between activity in tumor cell proliferation assays in vitro and anti-tumor activity in the clinical setting has been very well established in the art. For example, the therapeutic utility of taxol (Silvestrini et al. *Stem Cells* 1993, 11(6), 528-35), taxotere (Bissery et al. *Anti Cancer Drugs* 1995, 6(3), 339), and topoisomerase inhibitors (Edelman et al. *Cancer Chemother. Pharmacol.* 1996, 37(5), 385-93) were demonstrated with the use of in vitro tumor proliferation assays. Demonstration of the activity of the compounds of the present invention may be accomplished through in vitro, ex vivo, and in vivo assays that are well known in the art. For example, to demonstrate the activity of the compounds of the present invention, the following assays may be used.

Biological Assays

The effects of the compounds of the present invention were examined by the following assays.

Determination of $IC_{50}$ values of compounds in kinase assay of PI3Kα

Chemicals and Assay Materials

Phosphatidylinositol (PtdIns) and phosphatidylserine (PtdSer) were purchased from Doosan Serdary Research Laboratories (Toronto, Canada). Recombinant truncated forms (ΔN 1-108) of the human p110α and p110α subunits of PI3K with N-terminal His$_6$-Tags were expressed in *S. frugiperda* 9 insect cells. Recombinant human PI3Kγ (full length human PI3K p110γ fused with a His$_6$-tag at the C-terminus expressed in *S. frugiperda* 9 insect cells) was obtained from Alexis Biochemicals (#201-055-0010; San Diego, Calif.). [γ$^{33}$P]ATP and unlabeled ATP were purchased from Amersham Pharmacia Biotech (Buckinghamshire, UK) and Roche Diagnostics (Mannheim, Germany), respectively. Scintillation cocktails and MicroScint PS™ were purchased from Packard (Meriden, Conn.). Maxisorp™ plates were purchased from Nalge Nunc International K.K. (Tokyo, Japan). All other chemicals not further specified were from Wako Pure Chemicals (Osaka, Japan).

Solid-Phase Lipid Kinase Assay

To assess inhibition of PI3Kα by compounds, the Maxisorp™ plates were coated with 50 μL/well of a solution containing 50 μg/ml PtdIns and 50 μg/ml PtdSer dissolved in chloroform:ethanol (3:7). The plates were subsequently air-dried by incubation for at least 2 h in a fume hood. The reaction was set up by mixing 25 μL/well of assay buffer 2×(100 mM MOPSO/NaOH, 0.2 M NaCl, pH 7.0, 8 mM $MgCl_2$, 2 mg/mL BSA (fatty acid-free)), and 7.5 ng/well PI3Kα in the lipid pre-coated plate. Test compounds at different concentrations (0.0, 0.003, 0.01 0.03, 0.1, 0.3, 1.0, 3.0 and 10 μM) were added in 2% DMSO. The reaction was initiated by adding 20 μL/well of ATP mix (final 10 μM ATP; 0.05 μCi/well [γ$^{33}$P]ATP). After incubation at rt for 2 h, the reaction was terminated by adding 50 μl/well stop solution (50 mM EDTA, pH 8.0). The plate was then washed twice with Tris-buffered saline (TBS, pH 7.4). MicroScint PS™ (PACKARD) scintillation mix was added at 100 μL/well, and radioactivity was counted using a TopCount™ (PACKARD) scintillation counter.

The inhibition percent at each concentration of compound was calculated, and $IC_{50}$ values were determined from the inhibition of curve.

Isozyme Selectivity Test in PI3K

Chemicals and Assay Materials

A recombinant truncated form (ΔN1-108) of the human p110β subunit of PI3K with an N-terminal His$_6$-Tag was expressed in *S. frugiperda* 9 insect cells. Recombinant human PI3Kγ (full length human PI3K p110γ fused with a His$_6$-tag at the C-terminus expressed in *S. frugiperda* 9 insect cells) was obtained from Alexis Biochemicals (#201-055-0010; San Diego, Calif.).

Determination of $IC_{50}$ Values of Compounds in Kinase Assays of PI3Kβ and PI3Kγ

Kinase assays using recombinant truncated p110β or the full length p110γ were performed in a similar manner as described in the determination of $IC_{50}$ values of compounds in the kinase assay of PI3Kα except that these isoforms were assayed using 7.5 ng and 25.0 ng of protein/well, respectively.

Compounds that have an $IC_{50}$<0.1 µM in the PI3Kβ assay include those of Examples 1, 3, 4, 5, 6, 10, 11, 12, 13, 14, 15, 16, 17, 18, 19, 20, 21, 22, 23, 29, 31, 32, 33, 34, 35, 36, 37. Compounds that have $IC_{50}$ values between 0.1 µM and 3 µM include those of Examples 2, 7, 8, 9, 24, 25, 26, 27, 28, 30.

Determination of $IC_{50}$ Values of Compounds in Cell Based Assays of PI3K Activity Chemicals and Assay Materials 96-well collagen treated clear bottom/black sided Costar plates were purchased from CORNING LIFE SCIENCES (Corning, N.Y.; at.#3904). Gibco RPMI medium (Cat.#11875), Biosource anti-phospho-AKT(Ser 473) antibody (Cat.#44-621G) and recombinant IGF-1 (Cat.# PHG0074) were purchased from INVITROGEN (Carlsbad, Calif.). The secondary donkey anti-rabbit IgG horse radish peroxidase conjugate (Cat. # NA934V) and ECL chemiluminesence reagent (Cat.# RPN2209) were purchased from AMERSHAM (Buckinghamshire, UK). Cell culture tested bovine serum albumin solution (35% in DPBS; Cat.# A7979) and all other chemicals were purchased from SIGMA (St. Louis, Mo.). The Wallac Victor2 1420 Multilabel HTS Counter was purchased from PERKINELMER (Wellesley, Mass.)

IGF-1 Induced AKT Phosphorylation Assay

To test inhibition of IGF-1 induced AKT phosphorylation by compounds, A549 cells ($5 \times 10^4$ cells/well) were seeded in 100 µL of 0.1% bovine serum albumin (BSA) in RPMI medium in 96-well collagen treated clear bottom/black sided plates and incubated overnight at 37° C. in a 5% $CO_2$ incubator. 10× compound solution (in 0.1% BSA in RPMI) was added to the plates and incubation at 37° C. was continued for 1 hour. All wells (except no IGF-1 controls) were then treated with 25 ng/ml IGF-1 for 10 minutes at 37° C. in a 5% $CO_2$ incubator. Following removal of the supernatants and washing with the wells with TBS (50 mM Tris pH 8.0 containing 138 mM NaCL and 27 mM KCl), 200 µL of 3.7% formaldehyde in TBS was added to each well, and the plate was incubated at 4° C. for 10 minutes. Supernatants were once again removed and replaced with 50 µL Methanol (−20° C.) and the plate incubated at 4° C. for 5 minutes. 200 µL of 0.1% BSA in TBS was then added to each well and the plate incubated at room temperature for ½ hour. Supernatants were removed and 50 µL of a solution comprising the primary anti-phospho-AKT(Ser 473) antibody diluted 1:250 in TBS containing 0.1% BSA was added to each well (except control/background wells). The plate was then incubated for 1½ hour at room temperature. Supernatants were removed, each well was washed 3 times with 200 µL TBS, and 100 µL of a solution containing the secondary donkey anti-rabbit IgG antibody HRP-conjugate diluted 1:100 in TBS-T (TBS containing 0.1% triton). Plates were then incubated for 1 hour at room temperature. After removing the secondary antibody, each well was washed 6 times with cold TBS-T, 100 µL of ECL was added to each well, and the plate was placed on an orbital shaker for 1 minute. The plates were then read on a Wallac Victor2 1420 Multilabel HTS Counter using the luminometry window (maximum light detection is measured at 428 nM). $IC_{50}$ values were determined from the inhibition curve.

Determination of In Vivo Efficacy Using Xenograft Models

Mouse

To evaluate the in vivo anti-tumor effect of PI3K inhibitors, efficacy studies were conducted in the NCr athymic female mice (Taconic, N.Y.). Human carcinoma cells of various histological types were harvested from mid-log phase cultures using Trypsin-EDTA (Gibco). Cells were pelleted, rinsed twice, and resuspended in sterile HBSS (Hank's Balanced Salt Solution) to final concentration of $2.5 \times 10^6$ cells/ml. Cells were implanted subcutaneously (s.c.) in a 0.2 ml volume ($5 \times 10^6$ cells) into the right flank. When tumors reached an average size of ~100-125 mg, the mice were randomized, and treatment initiated. Each experimental group consisted of 10 mice and the dosing volume was 10 ml/kg body weight. Compounds were dissolved in a compatible vehicle for both intravenous and oral administration. For intravenous administration, mice are placed under a heat lamp to warm for 5 minutes, then placed in a restraining device and the tail vein injected with a sterile 27 gauge ½ inch needle. Oral dosing utilizes sterile disposable feeding needles (20 gauge/1½ inches) from Popper and Sons, New Hyde Park, N.Y. Tumor growth was measured with electronic calipers 2-3 times a week and tumor weight (mg) calculated according to the following formula: [length (mm)×width (mm)2]/2. Percent inhibition or tumor growth inhibition (TGI) is calculated on days of measurement using the following formula: (100−mean tumor value of treated (T)/mean tumor of control value (C)×100)=% T/C. Of note: the control used in the calculations is either the "untreated control" or "vehicle", whichever provides the most conservative representation of the data.

Rat

To evaluate the in vivo anti-tumor effect of PI3K inhibitors, efficacy studies were conducted in the HSD athymic female rats (Harlan, Id.). Human carcinoma cells of various histological types were harvested from mid-log phase cultures using Trypsin-EDTA (Gibco). Cells were pelleted, rinsed twice, and resuspended in sterile HBSS (Hank's Balanced Salt Solution) to final concentration of $2.5 \times 10^6$ cells/ml. Cells were implanted subcutaneously (s.c.) in a 0.2 ml volume ($5 \times 10^6$ cells) into the right flank. When tumors reached an average size of ~200-400 mg, the rats were randomized, and treatment initiated. Each experimental group consisted of 10 nude rats. Compounds were dissolved in a compatible vehicle for both intravenous and oral administration. For intravenous administration of compound, rats were warmed under a heating lamp for 5 minutes, then placed in a restraining device, and injected intravenously via the tail vein using a dosing volume ranging from 2 mL/kg to 5 mL/kg with a sterile 25 gauge needle. Oral dosing utilizes sterile disposable feeding needles (18 gauge/2 inch) from Popper and Sons, New Hyde Park, N.Y. Tumor growth was measured with electronic calipers 2-3 times a week and tumor weight (mg) calculated according to the following formula: [length (mm)×width (mm)2]/2. Percent inhibition or tumor growth inhibition (TGI) is calculated on days of measurement using the following formula: (100−mean tumor value of treated (T)/mean tumor of control value (C)×100)=% T/C. Of note: the control used in the calculations is either the "untreated control" or "vehicle", whichever provides the most conservative representation of the data.

It is believed that one skilled in the art, using the preceeding information and information available in the art, can utilize the present invention to its fullest extent. Those skilled in the art will recognize that the invention may be practiced with variations on the disclosed structures, materials, compositions and methods without departing from the spirit or scope of the invention as it is set forth herein and such variations are regarded as within the ambit of the invention. The compounds described in the examples are intended to be representative of the invention, and it will be understood that the scope of the invention is not limited by the scope of the examples. The topic headings set forth above are meant as guidance where certain information can be found in the application, but are not intended to be the only source in the application where information on such topics can be found. All publications and patents cited above are incorporated herein by reference.

REFERENCES

1. Abbosh, P. H.; Nephew, K. P. Multiple signaling pathways converge on b-catenin in thyroid cancer. Thyroid 2005, 15, 551-561.
2. Ali, I. U.; Schriml, L. M.; Dean, M. Mutational spectra of PTEN/MMAC1 gene: a tumor suppressor with lipid phosphatase activity. J. Natl. Cancer Inst. 1999, 91, 1922-1932.
3. Bachman, K. E.; Argani, P.; Samuels, Y.; Silliman, N.; Ptak, J.; Szabo, S.; Konishi, H.; Karakas, B.; Blair, B. G.; Lin, C.; Peters, B. A.; Velculescu, V. E.; Park, B. H. The PIK3CA gene is mutated with high frequency in human breast cancers. Cancer Biol. Therap. 2004, 3, 772-775.
4. Bader, A. G.; Kang, S.; Vogt, P. K. Cancer-specific mutations in PIK3CA are oncogenic in vivo. Proc. Natl. Acad. Sci. U.S.A. 2006, 103, 1475-1479.
5. Barthwal, M. K.; Sathyanarayana, P.; Kundu, C. N.; Rana, B.; Pradeep, A.; Sharma, C.; Woodgett, J. R.; Rana, A. Negative Regulation of Mixed Lineage Kinase 3 by Protein Kinase B/AKT Leads to Cell Survival. J. Biol. Chem. 2003, 278, 3897-3902.
6. Bénistant, C.; Chapuis, H.; Roche, S. A specific function for phosphatidylinositol 3-kinase a (p85a-p110a) in cell survival and for phosphatidylinositol 3-kinase b (p85a-p110b) in de novo DNA synthesis of human colon carcinoma cells. Oncogene 2000, 19, 5083-5090.
7. Broderick, D. K.; Di, C.; Parrett, T. J.; Samuels, Y. R.; Cummins, J. M.; McLendon, R. E.; Fults, D. W.; Velculescu, V. E.; Bigner, D. D.; Yan, H. Mutations of PIK3CA in anaplastic oligodendrogliomas, high-grade astrocytomas, and medulloblastomas. Cancer Res. 2004, 64, 5048-5050.
8. Brown, R. A.; Shepherd, P. R. Growth factor regulation of the novel class II phosphoinositide 3-kinases. Biochem. Soc. Trans. 2001, 29, 535-537.
9. Brunet, A.; Bonni, A.; Zigmond, M. J.; Lin, M. Z.; Juo, P.; Hu, L. S.; Anderson, M. J.; Arden, K. C.; Blenis, J.; Greenberg, M. E. Akt promotes cell survival by phosphorylating and inhibiting a Forkhead transcription factor. Cell 1999, 96, 857-868.
10. Byun, D.-S.; Cho, K.; Ryu, B.-K.; Lee, M.-G.; Park, J.-I.; Chae, K.-S.; Kim, H.-J.; Chi, S.-G. Frequent monoallelic deletion of PTEN and its reciprocal association with PIK3CA amplification in gastric carcinoma. Int. J. Cancer 2003, 104, 318-327.
11. Campbell, I. G.; Russell, S. E.; Choong, D. Y. H.; Montgomery, K. G.; Ciavarella, M. L.; Hooi, C. S. F.; Cristiano, B. E.; Pearson, R. B.; Phillips, W. A. Mutation of the PIK3CA gene in ovarian and breast cancer. Cancer Res. 2004, 64, 7678-7681.
12. Cardone, M. H.; Roy, N.; Stennicke, H. R.; Salvesen, G. S.; Franke, T. F.; Stanbridge, E.; Frisch, S.; Reed, J. C. Regulation of cell death protease caspase-9 by phosphorylation. Science 1998, 282, 1318-1321.
13. Chen, Y. L.; Law, P.-Y.; Loh, H. H. Inhibition of PI3K/Akt signaling: An emerging paradigm for targeted cancer therapy. Curr. Med. Chem. Anticancer Agents 2005, 5, 575-589.
14. Ciechomska, I.; Pyrzynska, B.; Kazmierczak, P.; Kaminska, B. Inhibition of Akt kinase signalling and activation of Forkhead are indispensable for up-regulation of FasL expression in apoptosis of glioma cells. Oncogene 2003, 22, 7617-7627.
15. Cross, D. A. E.; Alessi, D. R.; Cohen, P.; Andjelkovich, M.; Hemmings, B. A. Inhibition of glycogen synthase kinase-3 by insulin mediated by protein kinase B. Nature 1995, 378, 785-9.
16. Cully, M.; You, H.; Levine, A. J.; Mak, T. W. Beyond PTEN mutations: the PI3K pathway as an integrator of multiple inputs during tumorigenesis. Nat. Rev. Cancer 2006, 6, 184-192.
17. Czauderna, F.; Fechtner, M.; Aygun, H.; Arnold, W.; Klippel, A.; Giese, K.; Kaufmann, J. Functional studies of the PI(3)-kinase signalling pathway employing synthetic and expressed siRNA. Nucleic Acids Res. 2003, 31, 670-682.
18. del Peso, L.; González-Garcia, M.; Page, C.; Herrera, R.; Nunez, G. Interleukin-3-induced phosphorylation of BAD through the protein kinase Akt. Science 1997, 278, 687-689.
19. Diehl, J. A.; Cheng, M.; Roussel, M. F.; Sherr, C. J. Glycogen synthase kinase-3b regulates cyclin D1 proteolysis and subcellular localization. Genes Dev. 1998, 12, 3499-3511.
20. Dijkers, P. F.; Medema, R. H.; Lammers, J.-W. J.; Koenderman, L.; Coffer, P. J. Expression of the pro-apoptotic Bcl-2 family member Bim is regulated by the Forkhead transcription factor FKHR-L1. Curr. Biol. 2000, 10, 1201-1204.
21. Domin, J.; Waterfield, M. D. Using structure to define the function of phosphoinositide 3-kinase family members. FEBS Lett. 1997, 410, 91-95.
22. Downes, C. P.; Gray, A.; Lucocq, J. M. Probing phosphoinositide functions in signaling and membrane trafficking. Trends Cell Biol. 2005, 15, 259-268.
23. Figueroa, C.; Tarras, S.; Taylor, J.; Vojtek, A. B. Akt2 negatively regulates assembly of the POSH-MLK-JNK signaling complex. J. Biol. Chem. 2003, 278, 47922-47927.
24. Fleming, I. N.; Gray, A.; Downes, C. P. Regulation of the Rac1-specific exchange factor tiam1 involves both phosphoinositide 3-kinase-dependent and -independent components. Biochem. J. 2000, 351, 173-182.
25. Funaki, M.; Katagiri, H.; Inukai, K.; Kikuchi, M.; Asano, T. Structure and function of phosphatidylinositol-3,4 kinase. Cell. Signal. 2000, 12, 135-142.
26. Gallia, G. L.; Rand, V.; Siu, I. M.; Eberhart, C. G.; James, C. D.; Marie, S. K. N.; Oba-Shinjo, S. M.; Carlotti, C. G.; Caballero, O. L.; Simpson, A. J. G.; Brock, M. V.; Massion, P. P.; Carson, B. S., Sr.; Riggins, G. J. PIK3CA gene mutations in pediatric and adult glioblastoma multiforme. Mol. Cancer. Res. 2006, 4, 709-714.
27. Gershtein, E. S.; Shatskaya, V. A.; Ermilova, V. D.; Kushlinsky, N. E.; Krasil'nikov, M. A. Phosphatidylinositol 3-kinase expression in human breast cancer. Clin. Chim. Acta 1999, 287, 59-67.
28. Gottschalk, A. R.; Doan, A.; Nakamura, J. L.; Stokoe, D.; Haas-Kogan, D. A. Inhibition of phosphatidylinositol-3-kinase causes increased sensitivity to radiation through a PKB-dependent mechanism. Int. J. Radiat. Oncol. Biol. Phys. 2005, 63, 1221-1227.
29. Gupta, A. K.; Cerniglia, G. J.; Mick, R.; Ahmed, M. S.; Bakanauskas, V. J.; Muschel, R. J.; McKenna, W. G. Radiation sensitization of human cancer cells in vivo by inhibiting the activity of PI3K using LY294002. Int. J. Radiat. Oncol. Biol. Phys. 2003, 56, 846-853.
30. Haas-Kogan, D.; Shalev, N.; Wong, M.; Mills, G.; Yount, G.; Stokoe, D. Protein kinase B (PKB/Akt) activity is elevated in glioblastoma cells due to mutation of the tumor suppressor PTEN/MMAC. Curr. Biol. 1998, 8, 1195-1198.
31. Hartmann, C.; Bartels, G.; Gehlhaar, C.; Holtkamp, N.; von Deimling, A. PIK3CA mutations in glioblastoma multiforme. Acta Neuropathol. 2005, 109, 639-642.

32. Hennessy, B. T.; Smith, D. L.; Ram, P. T.; Lu, Y.; Mills, G. B. Exploiting the PI3K/AKT Pathway for Cancer Drug Discovery. Nat. Rev. Drug Disc. 2005, 4, 988-1004.

33. Hodgkinson, C. P.; Sale, E. M.; Sale, G. J. Characterization of PDK2 activity against Protein Kinase B gamma. Biochemistry 2002, 41, 10351-10359.

34. Hresko, R. C.; Murata, H.; Mueckler, M. Phosphoinositide-dependent Kinase-2 is a distinct protein kinase enriched in a novel cytoskeletal fraction associated with adipocyte plasma membranes. J. Biol. Chem. 2003, 278, 21615-21622.

35. Huang, C.; Ma, W.-Y.; Dong, Z. Requirement for phosphatidylinositol 3-kinase in epidermal growth factor-induced AP-1 transactivation and transformation in JB6 P+ cells. Mol. Cell. Biol. 1996, 16, 6427-6435.

36. Hupp, T. R.; Lane, D. P.; Ball, K. L. Strategies for manipulating the p53 pathway in the treatment of human cancer. Biochem. J. 2000, 352, 1-17.

37. Ihle, N. T.; Williams, R.; Chow, S.; Chew, W.; Berggren, M. I.; Paine-Murrieta, G.; Minion, D. J.; Halter, R. J.; Wipf, P.; Abraham, R.; Kirkpatrick, L.; Powis, G. Molecular pharmacology and antitumor activity of PX-866, a novel inhibitor of phosphoinositide-3-kinase signaling. Mol. Cancer. Therap. 2004, 3, 763-772.

38. Ikenoue, T.; Kanai, F.; Hikiba, Y.; Obata, T.; Tanaka, Y.; Imamura, J.; Ohta, M.; Jazag, A.; Guleng, B.; Tateishi, K.; Asaoka, Y.; Matsumura, M.; Kawabe, T.; Omata, M. Functional analysis of PIK3CA gene mutations in human colorectal cancer. Cancer Res. 2005, 65, 4562-4567.

39. Ishii, N.; Maier, D.; Merlo, A.; Tada, M.; Sawamura, Y.; Diserens, A.-C.; Van Meir, E. G. Frequent co-alterations of TP53, p16/CDKN2A, p14ARF, PTEN tumor suppressor genes in human glioma cell lines. Brain Pathol. 1999, 9, 469-479.

40. Itoh, T.; Takenawa, T. Phosphoinositide-binding domains. Functional units for temporal and spatial regulation of intracellular signalling. Cell. Signal. 2002, 14, 733-743.

41. Janssen, J. W. G.; Schleithoff, L.; Bartram, C. R.; Schulz, A. S. An oncogenic fusion product of the phosphatidylinositol 3-kinase p85b subunit and HUMORF8, a putative deubiquitinating enzyme. Oncogene 1998, 16, 1767-1772.

42. Jimenez, C.; Jones, D. R.; Rodriguez-Viciana, P.; Gonzalez-Garcia, A.; Leonardo, E.; Wennstrom, S.; Von Kobbe, C.; Toran, J. L.; R.-Borlado, L.; Calvo, V.; Copin, S. G.; Albar, J. P.; Gaspar, M. L.; Diez, E.; Marcos, M. A. R.; Downward, J.; Martinez-A, C.; Merida, I.; Carrera, A. C. Identification and characterization of a new oncogene derived from the regulatory subunit of phosphoinositide 3-kinase. EMBO J. 1998, 17, 743-753.

43. Jucker, M.; Sudel, K.; Horn, S.; Sickel, M.; Wegner, W.; Fiedler, W.; Feldman, R. A. Expression of a mutated form of the p85a regulatory subunit of phosphatidylinositol 3-kinase in a Hodgkin's lymphoma-derived cell line (CO). Leukemia 2002, 16, 894-901.

44. Kang, S.; Bader, A. G.; Vogt, P. K. Phosphatidylinositol 3-kinase mutations identified in human cancer are oncogenic. Proc. Natl. Acad. Sci. U.S.A. 2005, 102, 802-807.

45. Kang, S.; Denley, A.; Vanhaesebroeck, B.; Vogt, P. K. Oncogenic transformation induced by the p110b, -g, and -d isoforms of class I phosphoinositide 3-kinase. Proc. Natl. Acad. Sci. U.S.A. 2006, 103, 1289-1294.

46. Katso, R.; Okkenhaug, K.; Ahmadi, K.; White, S.; Timms, J.; Waterfield, M. D. Cellular function of phosphoinositide 3-kinases: implications for development, immunity, homeostasis, and cancer. Annu. Rev. Cell Dev. Biol. 2001, 17, 615-675.

47. Kim, A. H.; Khursigara, G.; Sun, X.; Franke, T. F.; Chao, M. V. Akt phosphorylates and negatively regulates apoptosis signal-regulating kinase 1. Mol. Cell. Biol. 2001, 21, 893-901.

48. Kim, D.; Dan, H. C.; Park, S.; Yang, L.; Liu, Q.; Kaneko, S.; Ning, J.; He, L.; Yang, H.; Sun, M.; Nicosia, S. V.; Cheng, J. Q. AKT/PKB signaling mechanisms in cancer and chemoresistance. Front. Biosci. 2005, 10, 975-987.

49. Klippel, A.; Kavanaugh, W. M.; Pot, D.; Williams, L. T. A specific product of phosphatidylinositol 3-kinase directly activates the protein kinase Akt through its pleckstrin homology domain. Mol. Cell. Biol. 1997, 17, 338-44.

50. Kodaki, T.; Woscholski, R.; Hallberg, B.; Rodriguez-Viciana, P.; Downward, J.; Parker, P. J. The activation of phosphatidylinositol 3-kinase by Ras. Curr. Biol. 1994, 4, 798-806.

51. Kops, G. J. P. L.; De Ruiter, N. D.; De Vries-Smits, A. M. M.; Powell, D. R.; Bos, J. L.; Burgering, B. M. T. Direct control of the Forkhead transcription factor AFX by protein kinase B. Nature 1999, 398, 630-634.

52. Lee, J. T., Jr.; Steelman, L. S.; McCubrey, J. A. Phosphatidylinositol 3'-Kinase Activation Leads to Multidrug Resistance Protein-1 Expression and Subsequent Chemoresistance in Advanced Prostate Cancer Cells. Cancer Res. 2004, 64, 8397-8404.

53. Lee, J. W.; Soung, Y. H.; Kim, S. Y.; Lee, H. W.; Park, W. S.; Nam, S. W.; Kim, S. H.; Lee, J. Y.; Yoo, N. J.; Lee, S. H. PIK3CA gene is frequently mutated in breast carcinomas and hepatocellular carcinomas. Oncogene 2005, 24, 1477-1480.

54. Lemmon, M. A. Phosphoinositide recognition domains. Traffic 2003, 4, 201-213.

55. Levine, D. A.; Bogomolniy, F.; Yee, C. J.; Lash, A.; Barakat, R. R.; Borgen, P. I.; Boyd, J. Frequent Mutation of the PIK3CA Gene in Ovarian and Breast Cancers. Clin. Cancer Res. 2005, 11, 2875-2878.

56. Li, J.; Yen, C.; Liaw, D.; Podsypanina, K.; Bose, S.; Wang, S. I.; Puc, J.; Miliaresis, C.; Rodgers, L.; McCombie, R.; Bigner, S. H.; Giovanella, B. C.; Ittmann, M.; Tycko, B.; Hibshoosh, H.; Wigler, M. H.; Parsons, R. PTEN, a putative protein tyrosine phosphatase gene mutated in human brain, breast, and prostate cancer. Science 1997, 275, 1943-1947.

57. Li, V. S. W.; Wong, C. W.; Chan, T. L.; Chan, A. S. W.; Zhao, W.; Chu, K.-M.; So, S.; Chen, X.; Yuen, S. T.; Leung, S. Y. Mutations of PIK3CA in gastric adenocarcinoma. BMC Cancer 2005, 5, 29.

58. Liao, Y.; Hung, M.-C. Regulation of the activity of p38 mitogen-activated protein kinase by Akt in cancer and adenoviral protein E1A-mediated sensitization to apoptosis. Mol. Cell. Biol. 2003, 23, 6836-6848.

59. Lopez-Ilasaca, M.; Li, W.; Uren, A.; Yu, J.-c.; Kazlauskas, A.; Gutkind, J. S.; Heidaran, M. A. Requirement of phosphatidylinositol-3 kinase for activation of JNK/SAPKs by PDGF. Biochem. Biophys. Res. Commun. 1997, 232, 273-277.

60. Ma, Y.-Y.; Wei, S.-J.; Lin, Y.-C.; Lung, J.-C.; Chang, T.-C.; Whang-Peng, J.; Liu, J. M.; Yang, D.-M.; Yang, W. K.; Shen, C.-Y. PIK3CA as an oncogene in cervical cancer. Oncogene 2000, 19, 2739-2744.

61. Mayo, L. D.; Dixon, J. E.; Durden, D. L.; Tonks, N. K.; Donner, D. B. PTEN protects p53 from Mdm2 and sensitizes cancer cells to chemotherapy. J. Biol. Chem. 2002, 277, 5484-5489.

62. Momand, J.; Wu, H.-H.; Dasgupta, G. MDM2—master regulator of the p53 tumor suppressor protein. Gene 2000, 242, 15-29.

63. Motti, M. L.; De Marco, C.; Califano, D.; Fusco, A.; Viglietto, G. Akt-dependent T198 phosphorylation of cyclin-dependent kinase inhibitor p27kip1 in breast cancer. Cell Cycle 2004, 3, 1074-1080.
64. Myers, M. P.; Pass, I.; Batty, I. H.; Van Der Kaay, J.; Stolarov, J. P.; Hemmings, B. A.; Wigler, M. H.; Downes, C. P.; Tonks, N. K. The lipid phosphatase activity of PTEN is critical for its tumor suppressor function. Proc. Natl. Acad. Sci. U.S. A. 1998, 95, 13513-13518.
65. Nagata, Y.; Lan, K.-H.; Zhou, X.; Tan, M.; Esteva, F. J.; Sahin, A. A.; Klos, K. S.; Li, P.; Monia, B. P.; Nguyen, N. T.; Hortobagyi, G. N.; Hung, M.-C.; Yu, D. PTEN activation contributes to tumor inhibition by trastuzumab, and loss of PTEN predicts trastuzumab resistance in patients. Cancer Cell 2004, 6, 117-127.
66. Naito, A. T.; Akazawa, H.; Takano, H.; Minamino, T.; Nagai, T.; Aburatani, H.; Komuro, I. Phosphatidylinositol 3-Kinase-Akt Pathway Plays a Critical Role in Early Cardiomyogenesis by Regulating Canonical Wnt Signaling. Circ. Res. 2005, 97, 144-151.
67. Oda, K.; Stokoe, D.; Taketani, Y.; McCormick, F. High Frequency of Coexistent Mutations of PIK3CA and PTEN Genes in Endometrial Carcinoma. Cancer Res. 2005, 65, 10669-10673.
68. Ogawara, Y.; Kishishita, S.; Obata, T.; Isazawa, Y.; Suzuki, T.; Tanaka, K.; Masuyama, N.; Gotoh, Y. Akt enhances Mdm2-mediated ubiquitination and degradation of p53. J. Biol. Chem. 2002, 277, 21843-21850.
69. Olson, J. M.; Hallahan, A. R. p38 MAP kinase: a convergence point in cancer therapy. Trends Mol. Med. 2004, 10, 125-129.
70. Osaki, M.; Oshimura, M.; Ito, H. PI3K-Akt pathway: Its functions and alterations in human cancer. Apoptosis 2004, 9, 667-676.
71. Pastorino, J. G.; Tafani, M.; Farber, J. L. Tumor necrosis factor induces phosphorylation and translocation of BAD through a phosphatidylinositide-3-OH kinase-dependent pathway. J. Biol. Chem. 1999, 274, 19411-19416.
72. Pendaries, C.; Tronchere, H.; Plantavid, M.; Payrastre, B. Phosphoinositide signaling disorders in human diseases. FEBS Lett. 2003, 546, 25-31.
73. Phillips, W. A.; St. Clair, F.; Munday, A. D.; Thomas, R. J. S.; Mitchell, C. A. Increased levels of phosphatidylinositol 3-kinase activity in colorectal tumors. Cancer 1998, 83, 41-47.
74. Philp, A. J.; Campbell, I. G.; Leet, C.; Vincan, E.; Rockman, S. P.; Whitehead, R. H.; Thomas, R. J. S.; Phillips, W. A. The phosphatidylinositol 3'-kinase p85a gene is an oncogene in human ovarian and colon tumors. Cancer Res. 2001, 61, 7426-7429.
75. Powis, G.; Bonjouklian, R.; Berggren, M. M.; Gallegos, A.; Abraham, R.; Ashendel, C.; Zalkow, L.; Matter, W. F.; Dodge, J. Wortmannin, a potent and selective inhibitor of phosphatidylinositol-3-kinase. Cancer Res. 1994, 54, 2419-23.
76. Pu, P.; Kang, C.; Zhang, Z.; Liu, X.; Jiang, H. Downregulation of PIK3CB by siRNA suppresses malignant glioma cell growth in vitro and in vivo. Technol. Cancer Res. Treat. 2006, 5, 271-280.
77. Rahimi, N.; Tremblay, E.; Elliott, B. Phosphatidylinositol 3-kinase activity is required for hepatocyte growth factor-induced mitogenic signals in epithelial cells. J. Biol. Chem. 1996, 271, 24850-24855.
78. Roche, S.; Downward, J.; Raynal, P.; Courtneidge, S. A. A function for phosphatidylinositol 3-kinase b (p85a-p110b) in fibroblasts during mitogenesis: requirement for insulin- and lysophosphatidic acid-mediated signal transduction. Mol. Cell. Biol. 1998, 18, 7119-7129.
79. Roche, S.; Koegl, M.; Courtneidge, S. A. The phosphatidylinositol 3-kinase a is required for DNA synthesis induced by some, but not all, growth factors. Proc. Natl. Acad. Sci. U.S.A. 1994, 91, 9185-9.
80. Romashkova, J. A.; Makarov, S. S, Nf-kB is a target of Akt in anti-apoptotic PDGF signalling. Nature 1999, 401, 86-90.
81. Saal, L. H.; Holm, K.; Maurer, M.; Memeo, L.; Su, T.; Wang, X.; Yu, J. S.; Malmstroem, P.-O.; Mansukhani, M.; Enoksson, J.; Hibshoosh, H.; Borg, A.; Parsons, R. PIK3CA mutations correlate with hormone receptors, node metastasis, and ERBB2, and are mutually exclusive with PTEN loss in human breast carcinoma. Cancer Res. 2005, 65, 2554-2559.
82. Samuels, Y.; Diaz, L. A., Jr.; Schmidt-Kittler, O.; Cummins, J. M.; DeLong, L.; Cheong, I.; Rago, C.; Huso, D. L.; Lengauer, C.; Kinzler, K. W.; Vogelstein, B.; Velculescu, V. E. Mutant PIK3CA promotes cell growth and invasion of human cancer cells. Cancer Cell 2005, 7, 561-573.
83. Samuels, Y.; Ericson, K. Oncogenic PI3K and its role in cancer. Curr. Opin. Oncol. 2006, 18, 77-82.
84. Samuels, Y.; Wang, Z.; Bardelli, A.; Silliman, N.; Ptak, J.; Szabo, S.; Yan, H.; Gazdar, A.; Powell, S. M.; Riggins, G. J.; Willson, J. K. V.; Markowitz, S.; Kinzler, K. W.; Vogelstein, B.; Velculescu, V. E. Brevia: High frequency of mutations of the PIK3Ca gene in human cancers. Science 2004, 304, 554.
85. Scheid, M. P.; Marignani, P. A.; Woodgett, J. R. Multiple phosphoinositide 3-kinase-dependent steps in activation of protein kinase B. Mol. Cell. Biol. 2002, 22, 6247-6260.
86. Schultz, R. M.; Merriman, R. L.; Andis, S. L.; Bonjouklian, R.; Grindey, G. B.; Rutherford, P. G.; Gallegos, A.; Massey, K.; Powis, G. In vitro and in vivo antitumor activity of the phosphatidylinositol-3-kinase inhibitor, wortmannin. Anticancer Res. 1995, 15, 1135-9.
87. Segrelles, C.; Moral, M.; Lara, M. F.; Ruiz, S.; Santos, M.; Leis, H.; Garcia-Escudero, R.; Martinez-Cruz, A. B.; Martinez-Palacio, J.; Hernandez, P.; Ballestin, C.; Paramio, J. M. Molecular determinants of Akt-induced keratinocyte transformation. Oncogene 2006, 25, 1174-1185.
88. Sekimoto, T.; Fukumoto, M.; Yoneda, Y. 14-3-3 suppresses the nuclear localization of threonine 157-phosphorylated p27Kip1. EMBO J. 2004, 23, 1934-1942.
89. Semba, S.; Itoh, N.; Ito, M.; Youssef, E. M.; Harada, M.; Moriya, T.; Kimura, W.; Yamakawa, M. Down-regulation of PIK3CG catalytic subunit of phosphatidylinositol 3-OH kinase by CpG hypermethylation in human colorectal carcinoma. Clin. Cancer Res. 2002, 8, 3824-3831.
90. Shayesteh, L.; Lu, Y.; Kuo, W.-L.; Baldocchi, R.; Godfrey, T.; Collins, C.; Pinkel, D.; Powell, B.; Mills, G. B.; Gray, J. W. PIK3CA is implicated as an oncogene in ovarian cancer. Nat. Genet. 1999, 21, 99-102.
91. Shekar, S. C.; Wu, H.; Fu, Z.; Yip, S.-C.; Nagajyothi; Cahill, S. M.; Girvin, M. E.; Backer, J. M. Mechanism of Constitutive Phosphoinositide 3-Kinase Activation by Oncogenic Mutants of the p85 Regulatory Subunit. J. Biol. Chem. 2005, 280, 27850-27855.
92. Stahl, J. M.; Cheung, M.; Sharma, A.; Trivedi, N. R.; Shanmugam, S.; Robertson, G. P. Loss of PTEN Promotes Tumor Development in Malignant Melanoma. Cancer Res. 2003, 63, 2881-2890.
93. Stambolic, V.; Suzuki, A.; De La Pompa, J. L.; Brothers, G. M.; Mirtsos, C.; Sasaki, T.; Ruland, J.; Penninger, J. M.; Siderovski, D. P.; Mak, T. W. Negative regulation of PKB/

Akt-Dependent cell survival by the tumor suppressor PTEN. Cell 1998, 95, 29-39.
94. Stauffer, F.; Holzer, P.; Garcia-Echeverria, C. Blocking the PI3K/PKB pathway in tumor cells. Curr. Med. Chem. Anticancer Agents 2005, 5, 449-462.
95. Steck, P. A.; Pershouse, M. A.; Jasser, S. A.; Yung, W. K. A.; Lin, H.; Ligon, A. H.; Langford, L. A.; Baumgard, M. L.; Nattier, T.; Davis, T.; Frye, C.; Hu, R.; Swedlund, B.; Teng, D. H. F.; Tavtigian, S. V. Identification of a candidate tumor suppressor gene, MMAC1, at chromosome 10q23.3 that is mutated in multiple advanced cancers. Nat. Genet. 1997, 15, 356-362.
96. Stein, R. C.; Waterfield, M. D. PI3-kinase inhibition: a target for drug development? Mol. Med. Today 2000, 6, 347-358.
97. Stephens, L.; Williams, R.; Hawkins, P. Phosphoinositide 3-kinases as drug targets in cancer. Curr. Opin. Pharmacol. 2005, 5, 357-365.
98. Su, J. D.; Mayo, L. D.; Donner, D. B.; Durden, D. L. PTEN and Phosphatidylinositol 3'-Kinase Inhibitors Up-Regulate p53 and Block Tumor-induced Angiogenesis: Evidence for an Effect on the Tumor and Endothelial Compartment. Cancer Res. 2003, 63, 3585-3592.
99. Tanaka, M.; Grossman, H. B. In vivo gene therapy of human bladder cancer with PTEN suppresses tumor growth, downregulates phosphorylated Akt, and increases sensitivity to doxorubicin. Gene Ther. 2003, 10, 1636-1642.
100. Tang, E. D.; Nunez, G.; Barr, F. G.; Guan, K.-L. Negative regulation of the forkhead transcription factor FKHR by Akt. J. Biol. Chem. 1999, 274, 16741-16746.
101. Taylor, V.; Wong, M.; Brandts, C.; Reilly, L.; Dean, N. M.; Cowsert, L. M.; Moodie, S.; Stokoe, D. 5' Phospholipid phosphatase SHIP-2 causes protein kinase B inactivation and cell cycle arrest in glioblastoma cells. Mol. Cell. Biol. 2000, 20, 6860-6871.
102. Toker, A. Phosphoinositides and signal transduction. Cell. Mol. Life. Sci. 2002, 59, 761-779.
103. Traer, C. J.; Foster, F. M.; Abraham, S. M.; Fry, M. J. Are class II phosphoinositide 3-kinases potential targets for anticancer therapies? Bull. Cancer (Paris). 2006, 93, E53-8.
104. Vanhaesebroeck, B.; Leevers, S. J.; Ahmadi, K.; Timms, J.; Katso, R.; Driscoll, P. C.; Woscholski, R.; Parker, P. J.; Waterfield, M. D. Synthesis and function of 3-phosphory-lated inositol lipids. Annu. Rev. Biochem. 2001, 70, 535-602.
105. Vanhaesebroeck, B.; Waterfield, M. D. Signaling by Distinct Classes of Phosphoinositide 3-Kinases. Exp. Cell Res. 1999, 253, 239-254.
106. Vivanco, I.; Sawyers, C. L. The phosphatidylinositol 3-Kinase-AKT pathway in human cancer. Nat. Rev. Cancer 2002, 2, 489-501.
107. Wang, Y.; Helland, A.; Holm, R.; Kristensen Gunnar, B.; Borresen-Dale, A.-L. PIK3CA mutations in advanced ovarian carcinomas. Hum. Mutat. 2005, 25, 322.
108. West, K. A.; Castillo, S. S.; Dennis, P. A. Activation of the PI3K/Akt pathway and chemotherapeutic resistance. Drug Resist. Update. 2002, 5, 234-48.
109. Whyte, D. B.; Holbeck, S. L. Correlation of PIK3Ca mutations with gene expression and drug sensitivity in NCI-60 cell lines. Biochem. Biophys. Res. Commun. 2006, 340, 469-475.
110. Wilker, E.; Lu, J.; Rho, O.; Carbajal, S.; Beltran, L.; DiGiovanni, J. Role of PI3K/Akt signaling in insulin-like growth factor-1 (IGF-1) skin tumor promotion. Mol. Carcinog. 2005, 44, 137-145.
111. Workman, P. Inhibiting the phosphoinositide 3-kinase pathway for cancer treatment. Biochem. Soc. Trans. 2004, 32, 393-396.
112. Wu, G.; Xing, M.; Mambo, E.; Huang, X.; Liu, J.; Guo, Z.; Chatterjee, A.; Goldenberg, D.; Gollin, S. M.; Sukumar, S.; Trink, B.; Sidransky, D. Somatic mutation and gain of copy number of PIK3CA in human breast cancer. Breast Cancer Res. 2005, 7, R609-R616.
113. Wymann, M. P.; Sozzani, S.; Altruda, F.; Mantovani, A.; Hirsch, E. Lipids on the move: phosphoinositide 3-kinases in leukocyte function. Immunol. Today 2000, 21, 260-264.
114. Yap, D. B.; Hsieh, J. K.; Lu, X. Mdm2 inhibits the apoptotic function of p53 mainly by targeting it for degradation. J. Biol. Chem. 2000, 275, 37296-302.
115. Yuan, Z.-q.; Feldman, R. I.; Sussman, G. E.; Coppola, D.; Nicosia, S. V.; Cheng, J. Q. AKT2 Inhibition of Cisplatin-induced JNK/p38 and Bax Activation by Phosphorylation of ASK1: Implication of AKT2 in Chemoresistance. J. Biol. Chem. 2003, 278, 23432-23440.
116. Zhao, H.; Dupont, J.; Yakar, S.; Karas, M.; LeRoith, D. PTEN inhibits cell proliferation and induces apoptosis by downregulating cell surface IGF-IR expression in prostate cancer cells. Oncogene 2004, 23, 786-794.
117. Zhao, J. J.; Cheng, H.; Jia, S.; Wang, L.; Gjoerup, O. V.; Mikami, A.; Roberts, T. M. The p110α isoform of PI3K is essential for proper growth factor signaling and oncogenic transformation. Proc. Natl. Acad. Sci. U.S.A. 2006, 103, 16296-300.
118. Zhou, B. P.; Liao, Y.; Xia, W.; Spohn, B.; Lee, M.-H.; Hung, M.-C. Cytoplasmic localization of p21Cip1/WAF1 by Akt-induced phosphorylation in HER-2/neu-overexpressing cells. Nat. Cell Biol. 2001, 3, 245-252.

What is claimed is:

1. A compound having the formula:

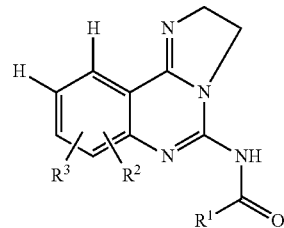

or a physiologically acceptable salt thereof, wherein:
$R^1$ is a heteroaryl optionally substituted with 1, 2 or 3 $R^4$ groups;
$R^2$ is hydrogen, alkoxy, heterocyclylalkyl, heterocyclylalkoxy or $R^3$;
each occurrence of $R^3$ is independently

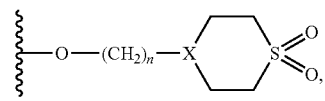

—Y—SO$_q$—Z or —Y—N(R$^5$)—SO$_q$—Z;
each occurrence of X is independently —C(R$^5$)— or —N—;
each occurrence of Y is independently a bond, alkoxy, alkoxyalkoxy or arylalkoxy;
each occurrence of Z is independently alkyl, —N(R$^6$)(R$^{6'}$), or -heterocyclylalkyl optionally substituted with 1, 2 or 3 R$^4$ groups;

each occurrence of R⁴ may be the same or different and is independently amino, halogen, amino, alkylamino, alkyl, alkenyl, alkynyl, cycloalkyl, cycloalkylalklyl, aryl, arylalkyl, heteroaryl, heteroarylalkyl, heterocyclyl or heterocyclylalkyl;

each occurrence of R⁵ is independently hydrogen or alkyl;

each occurrence of R⁶ and R⁶′ may be the same or different and is independently hydrogen, alkyl, alkenyl, alkynyl, cycloalkyl, cycloalkylalklyl, cycloalkenyl, aryl, arylalkyl, heteroaryl, heterocyclyl, or heterocyclylalkyl, wherein R⁶ and R⁶′ may be attached to each other to form a heterocyclic ring through a bond or through one or more O, C, N, S, SO$_q$ or carbonyl, and wherein at least one N is part of the heterocyclic ring; and each occurrence of n is independently an integer from 1-4; and each occurrence of p is independently an integer from 0-2.

2. The compound of claim 1, wherein R² is alkoxy.

3. The compound of claim 2, wherein R² is methoxy.

4. The compound of claim 1, wherein R¹ is pyridine, pyrimidine or thiazole, optionally substituted with 1, 2 or 3 R⁴ groups.

5. The compound of claim 4, wherein R¹ is pyridine, pyrimidine or thiazole, optionally substituted with 1 or 2 amino or methyl groups.

6. The compound of claim 5, wherein R¹ is pyridin-3-yl.

7. The compound of claim 1, wherein R² is N-morpholino-alkoxy.

8. The compound of claim 1, wherein R³—Y—SO₂—Z or —Y—NH—SO₂—Z.

9. The compound of claim 8, wherein Z is N-morpholino, methyl, or alkylamino.

10. The compound of claim 1, wherein:
R¹ is a heteroaryl optionally substituted with 1 R⁴ group;
R² is alkoxy or heterocyclylalkoxy;
R³ is independently

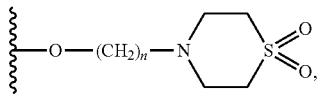

—Y—SO₂—Z or —Y—NH—SO₂—Z;

each occurrence of Y is independently alkoxy, alkoxyalkoxy, or arylalkoxy;

each occurrence of Z is independently alkyl, —N(R⁶)(R⁶′), or -heterocyclylalkyl;

each occurrence of R⁴ may be the same or different and is independently amino, halogen, amino, alkylamino, alkyl, alkenyl, alkynyl, cycloalkyl, cycloalkylalklyl, aryl, arylalkyl, heteroaryl, heteroarylalkyl, heterocycloalkyl or heterocycloalkylalkyl;

each occurence of R⁶ and R⁶′ may be the same or different and is independently hydrogen or alkyl; and each occurrence of n is independently an integer from 1-4.

11. The compound of claim 10, wherein:
R¹ is pyridine, pyrimidine, or thiazole optionally substituted with one amino or methyl group;
R² is methoxy or 3-morpholin-4-ylpropoxy;

R³ is independently

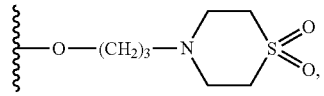

—Y—SO₂—Z or —Y—NH—SO₂—Z;

each occurrence of Y is independently alkoxy, alkoxyalkoxy, or arylalkoxy; and each occurrence of Z is independently methyl, morpholin-4-yl, or dimethylamino.

12. A compound having the formula:
N-(8-{3-[(ethylsulfonyl)amino]propoxy}-7-methoxy-2,3-dihydroimidazo[1,2-c]quinazolin-5-yl)nicotinamide;
N-[7-methoxy-8-(2-{2-[(propylsulfonyl)amino]ethoxy}ethoxy)-2,3-dihydroimidazo[1,2-c]quinazolin-5-yl]nicotinamide;
N-[7-methoxy-8-(2-{2-[(phenylsulfonyl)amino]ethoxy}ethoxy)-2,3-dihydroimidazo[1,2-c]quinazolin-5-yl]nicotinamide;
N-[7-methoxy-8-(2-{2-[(methylsulfonyl)amino]ethoxy}ethoxy)-2,3-dihydroimidazo[1,2-c]quinazolin-5-yl]nicotinamide;
N-{7-methoxy-8-[2-(2-{[(4-methylphenyl)sulfonyl]amino}ethoxy)ethoxy]-2,3-dihydroimidazo[1,2-c]quinazolin-5-yl}nicotinamide;
N-{8-[3-(morpholin-4-ylsulfonyl)propoxy]-2,3-dihydroimidazo[1,2-c]quinazolin-5-yl}nicotinamide;
N-(8-{3-[(4-methylpiperazin-1-yl)sulfonyl]propoxy}-2,3-dihydroimidazo[1,2-c]quinazolin-5-yl)nicotinamide;
N-(8-{[4-(methylsulfonyl)benzyl]oxy}-2,3-dihydroimidazo[1,2-c]quinazolin-5-yl)nicotinamide;
2,4-dimethyl-N-(8-{[4-(methylsulfonyl)benzyl]oxy}-2,3-dihydroimidazo[1,2-c]quinazolin-5-yl)-1,3-thiazole-5-carboxamide;
N-{8-[3-(morpholin-4-ylsulfonyl)propoxy]-2,3-dihydroimidazo[1,2-c]quinazolin-5-yl}pyrimidine-5-carboxamide;
2-amino-N-{8-[3-(morpholin-4-ylsulfonyl)propoxy]-2,3-dihydroimidazo[1,2-c]quinazolin-5-yl}pyrimidine-5-carboxamide;
6-amino-N-{8-[3-(morpholin-4-ylsulfonyl)propoxy]-2,3-dihydroimidazo[1,2-c]quinazolin-5-yl}nicotinamide;
N-(7-methoxy-8-{3-[(4-methylpiperazin-1-yl)sulfonyl]propoxy}-2,3-dihydroimidazo[1,2-c]quinazolin-5-yl)nicotinamide;
N-(7-methoxy-8-{[4-(methylsulfonyl)benzyl]oxy}-2,3-dihydroimidazo[1,2-c]quinazolin-5-yl)nicotinamide;
N-{7-methoxy-8-[3-(morpholin-4-ylsulfonyl)propoxy]-2,3-dihydroimidazo[1,2-c]quinazolin-5-yl}nicotinamide;
N-{8-[3-(1,1-dioxidothiomorpholin-4-yl)propoxy]-7-methoxy-2,3-dihydroimidazo[1,2-c]quinazolin-5-yl}nicotinamide;
N-(8-{3-[(diethylamino)sulfonyl]propoxy}-7-methoxy-2,3-dihydroimidazo[1,2-c]quinazolin-5-yl)nicotinamide;
N-(8-{3-[(dimethylamino)sulfonyl]propoxy}-7-methoxy-2,3-dihydroimidazo[1,2-c]quinazolin-5-yl)nicotinamide;
N-{7-[3-(morpholin-4-ylsulfonyl)propoxy]-2,3-dihydroimidazo[1,2-c]quinazolin-5-yl}nicotinamide;
N-(7-{3-[(4-methylpiperazin-1-yl)sulfonyl]propoxy}-2,3-dihydroimidazo[1,2-c]quinazolin-5-yl)nicotinamide;
N-{7-[3-(1,1-dioxidothiomorpholin-4-yl)propoxy]-2,3-dihydroimidazo[1,2-c]quinazolin-5-yl}nicotinamide;

N-(7-{[4-(methylsulfonyl)benzyl]oxy}-2,3-dihydroimidazo[1,2-c]quinazolin-5-yl)nicotinamide;
N-(7-{3-[(dimethylamino)sulfonyl]propoxy}-2,3-dihydroimidazo[1,2-c]quinazolin-5-yl)nicotinamide;
N-{8-(3-morpholin-4-ylpropoxy)-7-[3-(morpholin-4-ylsulfonyl)propoxy]-2,3-dihydroimidazo[1,2-c]quinazolin-5-yl}nicotinamide;
N-[7-{3-[(4-methylpiperazin-1-yl)sulfonyl]propoxy}-8-(3-morpholin-4-ylpropoxy)-2,3-dihydroimidazo[1,2-c]quinazolin-5-yl]nicotinamide;
N-[7-{3-[(diethylamino)sulfonyl]propoxy}-8-(3-morpholin-4-ylpropoxy)-2,3-dihydroimidazo[1,2-c]quinazolin-5-yl]nicotinamide;
N-[7-{3-[(dimethylamino)sulfonyl]propoxy}-8-(3-morpholin-4-ylpropoxy)-2,3-dihydroimidazo[1,2-c]quinazolin-5-yl]nicotinamide;
2-amino-N-(7-methoxy-8-{[4-(methylsulfonyl)benzyl]oxy}-2,3-dihydroimidazo[1,2-c]quinazolin-5-yl)pyrimidine-5-carboxamide;
2-amino-N-(8-{3-[(dimethylamino)sulfonyl]propoxy}-7-methoxy-2,3-dihydroimidazo[1,2-c]quinazolin-5-yl)pyrimidine-5-carboxamide;
6-amino-N-(8-{3-[(dimethylamino)sulfonyl]propoxy}-7-methoxy-2,3-dihydroimidazo[1,2-c]quinazolin-5-yl)nicotinamide;
6-amino-N-{8-[3-(1,1-dioxidothiomorpholin-4-yl)propoxy]-7-methoxy-2,3-dihydroimidazo[1,2-c]quinazolin-5-yl}nicotinamide;
6-amino-N-(7-methoxy-8-{[4-(methylsulfonyl)benzyl]oxy}-2,3-dihydroimidazo[1,2-c]quinazolin-5-yl)nicotinamide;
2-amino-N-{8-[3-(1,1-dioxidothiomorpholin-4-yl)propoxy]-7-methoxy-2,3-dihydroimidazo[1,2-c]quinazolin-5-yl}pyrimidine-5-carboxamide;
6-amino-N-{7-methoxy-8-[3-(morpholin-4-ylsulfonyl)propoxy]-2,3-dihydroimidazo[1,2-c]quinazolin-5-yl}nicotinamide;
2-amino-N-{7-methoxy-8-[3-(morpholin-4-ylsulfonyl)propoxy]-2,3-dihydroimidazo[1,2-c]quinazolin-5-yl}pyrimidine-5-carboxamide;
N-[7-{[4-(methylsulfonyl)benzyl]oxy}-8-(3-morpholin-4-ylpropoxy)-2,3-dihydroimidazo[1,2-c]quinazolin-5-yl]nicotinamide;
8-(3-morpholin-4-ylpropoxy)-5-[(pyridin-3-ylcarbonyl)amino]-2,3-dihydroimidazo[1,2-c]quinazolin-7-yl methanesulfonate;
or a physiologically acceptable salt thereof.

13. The compound of claim 10 having the formula:
N-{7-methoxy-8-[3-(morpholin-4-ylsulfonyl)propoxy]-2,3-dihydroimidazo[1,2-c]quinazolin-5-yl}nicotinamide;
N-{8-[3-(1,1-dioxidothiomorpholin-4-yl)propoxy]-7-methoxy-2,3-dihydroimidazo[1,2-c]quinazolin-5-yl}nicotinamide;
N-(8-{3-[(dimethylamino)sulfonyl]propoxy}-7-methoxy-2,3-dihydroimidazo[1,2-c]quinazolin-5-yl)nicotinamide;
N-{8-(3-morpholin-4-ylpropoxy)-7-[3-(morpholin-4-ylsulfonyl)propoxy]-2,3-dihydroimidazo[1,2-c]quinazolin-5-yl}nicotinamide;
N-[7-{3-[(dimethylamino)sulfonyl]propoxy}-8-(3-morpholin-4-ylpropoxy)-2,3-dihydroimidazo[1,2-c]quinazolin-5-yl]nicotinamide;
2-amino-N-(8-{3-[(dimethylamino)sulfonyl]propoxy}-7-methoxy-2,3-dihydroimidazo[1,2-c]quinazolin-5-yl)pyrimidine-5-carboxamide;
2-amino-N-{8-[3-(1,1-dioxidothiomorpholin-4-yl)propoxy]-7-methoxy-2,3-dihydroimidazo[1,2-c]quinazolin-5-yl}pyrimidine-5-carboxamide;
N-[7-methoxy-8-(2-{2-[(methylsulfonyl)amino]ethoxy}ethoxy)-2,3-dihydroimidazo[1,2-c]quinazolin-5-yl]nicotinamide;
N-[7-{[4-(methylsulfonyl)benzyl]oxy}-8-(3-morpholin-4-ylpropoxy)-2,3-dihydroimidazo[1,2-c]quinazolin-5-yl]nicotinamide
or a physiologically acceptable salt thereof.

14. A pharmaceutical composition comprising a therapeutically effective amount of a compound according to claim 1 and a pharmaceutically acceptable diluent or carrier.

15. The pharmaceutical composition of claim 14, further comprising an anti-hyper-proliferative, anti-inflammatory, analgesic, immunoregulatory, diuretic, anti-arrhythmic, anti-hypercholesterolemic, anti-diabetic, anti-dyslipidemia, anti-diabetic or antiviral agent.

16. The pharmaceutical composition of claim 15, wherein the further active compound is gemcitabine, paclitaxel, cisplatin, carboplatin, sodium butyrate, 5-FU, doxirubicin, tamoxifen, etoposide, trastumazab, gefitinib, intron A, rapamycin, 17-AAG, U0126, insulin, an insulin derivative, a PPAR ligand, a sulfonylurea drug, an α-glucosidase inhibitor, a biguanide, a PTP-1B inhibitor, a DPP-IV inhibitor, a 11-beta-HSD inhibitor, GLP-1, a GLP-1 derivative, GIP, a GIP derivative, PACAP, a PACAP derivative, secretin, secretin derivative, aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidine, chlorambucil, cisplatin, cladribine, cladribine, clodronic acid, cyclophosphamide, cytarabine, dacarbazine, dactinomycin, DaunoXome, decadron, decadron phosphate, delestrogen, denileukin diftitox, depo-medrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin alfa, epogen, eptaplatin, ergamisol, estrace, estradiol, estramustine phosphate sodium, ethinyl estradiol, ethyol, etidronic acid, etopophos, etoposide, fadrozole, farston, filgrastim, finasteride, fligrastim, floxuridine, fluconazole, fludarabine, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, goserelin, granisetron HCl, histrelin, hycamtin, hydrocortone, eyrthro-hydroxynonyladenine, hydroxyurea, ibritumomab tiuxetan, idarubicin, ifosfamide, interferon alpha, interferon-alpha 2, interferon alfa-2A, interferon alfa-2B, interferon alfa-n1, interferon alfa-n3, interferon beta, interferon gamma-1a, interleukin-2, intron A, iressa, irinotecan, kytril, lentinan sulphate, letrozole, leucovorin, leuprolide, leuprolide acetate, levamisole, levofolinic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, Mesna, methotrexate, metvix, miltefosine, minocycline, mitomycin C, mitotane, mitoxantrone, Modrenal, Myocet, nedaplatin, neulasta, neumega, neupogen, nilutamide, nolvadex, NSC-631570, OCT-43, octreotide, ondansetron HCl, orapred, oxaliplatin, paclitaxel, pediapred, pegaspargase, Pegasys, pentostatin, picibanil, pilocarpine HCl, pirarubicin, plicamycin, porfimer sodium, prednimustine, prednisolone, prednisone, premarin, procarbazine, procrit, raltitrexed, rebif, rhenium-186 etidronate, rituximab, roferon-A, romurtide, salagen, sandostatin, sargramostim, semustine, sizofiran, sobuzoxane, solumedrol, sparfosic acid, stem-cell therapy, streptozocin, strontium-89 chloride, synthroid, tamoxifen, tamsulosin, tasonermin, tastolactone, taxotere, teceleukin, temozolomide, teniposide, testosterone propionate, testred, thioguanine, thiotepa, thyrotropin, tiludronic acid, topotecan, toremifene, tositumomab, trastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, zofran, ABI-007, acolbifene, actimmune, affinitak, aminopterin, arzoxifene, asoprisnil, atamestane, atrasentan, sorafenib, avastin, CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon gamma, intron-PEG, ixabepilone, keyhole limpet hemocyanin, L-651582, lanreotide, lasofoxifene, libra, lonafarnib, miproxifene, minodronate, MS-209, liposomal MTP-PE, MX-6, nafarelin, nemorubicin, neovastat, nolatrexed, oblimersen, onco-TCS, osidem, paclitaxel polyglutamate, pamidronate disodium, PN-401, QS-21, quazepam, R-1549, raloxifene, ranpirnase, 13-cis-retinoic acid, satraplatin, seocalcitol, T-138067, tarceva, taxoprexin, thymosin alpha 1, tiazofurine, tipifarnib, tirapazamine, TLK-286, toremifene, TransMID-107R, valspodar, vapreotide, vatalanib, verteporfin, vinflunine, Z-100, zoledronic acid or combinations thereof.

\* \* \* \* \*